United States Patent [19]

Bagley et al.

[11] Patent Number: 5,401,745
[45] Date of Patent: Mar. 28, 1995

[54] QUINAZOLINONES SUBSTITUTED WITH PHENOXYPHENYLACETIC ACID DERIVATIVES

[75] Inventors: Scott W. Bagley, Rahway; Prasun K. Chakravarty, Edison; Anna Chen, Rahway; Daljit S. Dhanoa, Tinton Falls; Kenneth J. Fitch, Cranford; William J. Greenlee, Teaneck; Elizabeth M. Naylor, Scotch Plains; James R. Tata; Thomas F. Walsh, both of Westfield, all of N.J.; David L. Williams, Jr., Telford, Pa.

[73] Assignee: Merck & Co., Inc., Rahway, N.J.

[21] Appl. No.: 33,595

[22] Filed: Mar. 19, 1993

[51] Int. Cl.⁶ .............. A61K 31/505; A61K 31/54; C07D 239/95; C07D 239/86
[52] U.S. Cl. .................. 514/259; 544/249; 544/250; 544/287; 544/293; 544/289; 544/284; 544/244; 544/279; 544/116; 544/117; 544/105; 544/52; 544/51; 544/291; 544/285; 544/286; 514/80; 514/224.2; 514/230.5; 514/234.2; 514/234.5; 514/234.8; 514/249; 514/258; 514/260; 514/267
[58] Field of Search ............... 514/269, 256, 275, 80, 514/234.2, 249, 267; 544/315, 316, 318, 330, 331, 332, 333, 335, 296, 242, 287, 284, 289, 279, 105, 249, 285

[56] References Cited

U.S. PATENT DOCUMENTS

| 5,082,838 | 1/1992 | Naka et al. ............... 514/211 |
| 5,100,897 | 3/1992 | Allen et al. ............... 544/243 |
| 5,114,918 | 5/1992 | Ishikawa et al. ........... 514/11 |
| 5,177,095 | 1/1993 | Greenlee et al. ........... 514/384 |
| 5,183,810 | 2/1993 | Greenlee et al. ........... 514/63 |
| 5,187,195 | 2/1993 | Oohata et al. ............. 514/510 |

FOREIGN PATENT DOCUMENTS

| 0457195A2 | 5/1990 | European Pat. Off. . |
| 0460679A2 | 6/1990 | European Pat. Off. . |
| 0496452A1 | 1/1991 | European Pat. Off. . |
| 0526642A1 | 1/1991 | European Pat. Off. . |
| 0510526A1 | 4/1991 | European Pat. Off. . |
| 0526708A1 | 6/1991 | European Pat. Off. . |
| 2259450A | 3/1993 | United Kingdom . |
| WO92/15321 | 3/1991 | WIPO . |
| WO92/20706 | 5/1991 | WIPO . |
| WO/91/12001 | 8/1991 | WIPO . |

OTHER PUBLICATIONS

Ries et al, Chemical Abstracts, vol. 119, Entry 8825u (1993).
Greenlee et al, Chemical Abstracts, vol 115, Entry 256214v (1991).

*Primary Examiner*—John M. Ford
*Attorney, Agent, or Firm*—Valerie J. Camara; Mark R. Daniel; Joseph F. DiPrima

[57] ABSTRACT

Phenoxyphenylacetic acids and derivatives of general structural formula I

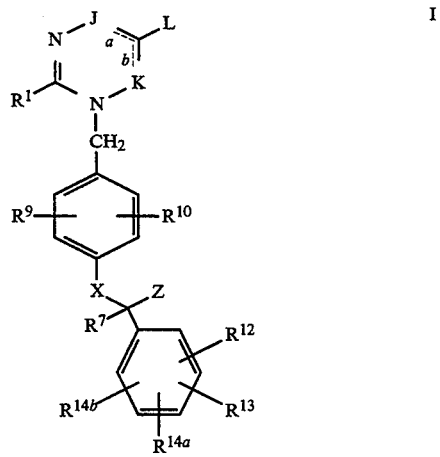

have endothelin antagonist activity and are therefore useful in treating cardiovascular disorders, such as hypertension, postischemic renal failure, vasospasm, cerebal and cardiac ischemia, myocardial infarction, inflammatory diseases, Raynaud's disease, and endotoxic shock, and asthma.

10 Claims, No Drawings

QUINAZOLINONES SUBSTITUTED WITH PHENOXYPHENYLACETIC ACID DERIVATIVES

SUMMARY OF THE INVENTION

This invention is concerned with non-peptidic endothelin receptor antagonists and their method of use. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells. [1-3]

Endothelin-1 (ET-1) is one of three recently identified potent vasoconstricting peptides which also includes endothelin-2 (ET-2) and endothelin-3 (ET-3) which differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14], prostacyclin, norepinephrine, angiotensin II and substance P.[11-16] Further, endothelin causes contraction of the smooth muscle of the gastrointestinal tract and the uterine smooth muscle.[1-7-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Substances which specifically inhibit the binding of endothelin to its receptor are believed to block the pathophysiological effects of endothelin and would be a useful method of treatment for a person in need of such therapy. The present invention discloses potent non-peptidic endothelin antagonists.

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction.

The novel compounds of the present invention are useful as non-peptidic endothelin antagonists, and have not been disclosed in any issued patents or patent applications. Fujisawa in European Patent Application EP 457,195, Banyu in EP 436,189 and 460,679, and Takeda in Patent Cooperation Treaty International Publication No. WO 91/13089 have applications disclosing linear and cyclic peptidic compounds as endothelin antagonists. Fujisawa has also disclosed anthraquinone derivatives produced by a fermentation process using *Streptomyces* sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin II antagonists. A patent from Hoffmann-La Roche (EP 510,526) has also appeared claiming the endothelin antagonist properties of a series of N-(4-pyrimidinyl)benzenesulfonamides.

REFERENCES

1 Nature, 332, 411–415 (1988).
2 FEBS Letters, 231, 440–444 (1988).
3 Biochem. Biophys. Res. Commun. 154, 868–875 (1988).
4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. USA, 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).

18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION

This invention relates to compounds of the general Formula I useful in this novel method of treatment:

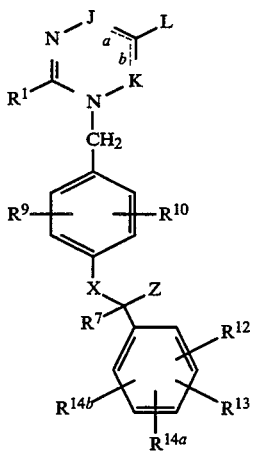

or a pharmaceutically acceptable salt thereof, wherein:
$R^1$ is:
(a) H,
(b) $(C_1-C_6)$-alkyl, $(C_2-C_6)$-alkenyl or $(C_2-C_6)$-alkynyl each of which is unsubstituted or substituted with a substituent selected from the group consisting of:
  i) aryl as defined below,
  ii) $(C_3-C_7)$-cycloalkyl,
  iii) Cl, Br, I, F,
  iv) OH,
  v) $NH_2$,
  vi) $NH(C_1-C_4)$-alkyl,
  vii) $N[(C_1-C_4)$-alkyl$]_2$,
  viii) $NHSO_2R^2$,
  ix) $CF_3$,
  x) $COOR^2$, or
  xi) $SO_2NHR^3$; and
(c) aryl, wherein aryl is defined as phenyl or naphthyl unsubstituted or substituted with 1 or 2 substituents selected from the group consisting of:
  i) Br, I, Cl, F,
  ii) $(C_1-C_4)$-alkyl,
  iii) $(C_1-C_4)$-alkoxy,
  iv) $NO_2$
  v) $CF_3$
  vi) $SO_2NR^3R^3$,
  vii) $(C_1-C_4)$-alkylthio,
  viii) hydroxy,
  ix) amino,
  x) $(C_3-C_7)$-cycloalkyl,
  xi) $(C_3-C_{10})$-alkenyl; and (d) heteroaryl, wherein heteroaryl is defined as a 5- or 6-membered heteroaromatic moiety selected from the group consisting of thiophene, furan, thiazole, oxazole, pyridine or pyrimidine, which is unsubstituted, mono- or disubstituted with substituents selected from the group consisting of:
  i) Cl, Br, I, or F,
  ii) OH,
  iii) SH,
  iv) $NO_2$,
  v) $(C_1-C_4)$-alkyl,
  vi) $(C_2-C_4)$-alkenyl,
  vii) $(C_2-C_4)$-alkynyl,
  viii) $(C_1-C_4)$-alkoxy, or
  ix) $CF_3$,
(e) $(C_1-C_4)$-perfluoroalkyl,
(f) $-O-(C_1-C_6)$-alkyl,
(g) $-S(O)_n-(C_1-C_9)$-alkyl,
(h) $-CONR^3R^3$, or
(i) $-NR^3CO-O-(C_1-C_4)$-alkyl; and
n is: 0 to 2; and
J is: (a) $-C(=M)-$, (b) J and L are connected together to form a 6-membered aromatic ring substituted with $R^{5a}$, $R^{5b}$, $R^{6a}$ and $R^{6b}$ or (c) J and L are connected together to form a 6-membered aromatic ring containing one nitrogen atom, substituted with $R^{5a}$, $R^{5b}$ and $R^{6b}$; and K is: (a) $-C(=M)-$, (b) K and L are connected together to form a 6-membered aromatic ring substituted with $R^{5a}$, $R^{5b}$, $R^{6a}$ and $R^{6b}$, or (c) K and L are connected together to form a 6-membered aromatic ring containing one nitrogen atom, substituted on the carbon atoms with $R^{5a}$, $R^{5b}$ and $R^{6b}$; and one of a or b is a double bond in Formula I provided that when J is $-C(=M)-$ then b is a double bond and when K is $-C(=M)-$ then a is a double bond;

L is the point of attachment of the 6-membered fused aromatic ring optionally containing one nitrogen atom; and M is: O, S or $NR^{11}$; and
$R^2$ is:
(a) H, or
(b) $(C_1-C_6)$-alkyl; and
$R^3$ is:
(a) $R^2$,
(b) $CH_2$-aryl,
(c) aryl, or
(d) $(C_3-C_7)$-cycloalkyl; and
$R^4$ groups are independently:
(a) H,
(b) $(C_1-C_6)$-alkyl or $(C_2-C_6)$-alkenyl each of which is unsubstituted or substituted with one of the following substituents,
  i) $-OH$,
  ii) $-O-(C_1-C_4)$-alkyl,
  iii) $-S(O)_n-(C_1-C_4)$-alkyl,
  iv) $-NR^3-(C_1-C_4)$-alkyl,
  v) $-NHR^3$,
  vi) $-COOR^3$,
  vii) $-CONHR^3$,
  ix) $-CONR^3R^{11}$, or
  x) $(C_3-C_7)$-cycloalkyl,
(c) $(C_3-C_7)$-cycloalkyl,
(d) F, Cl, Br, I,
(e) $CF_3$,
(f) $-COOR^3$,
(g) $-CONR^3R^{11}$,
(h) $-NR^3R^{11}$, (i) —NR³CONR³R¹¹,
(j) —NR³COOR¹¹,
(k) —SO₂NR³R¹¹,
(l) —O—(C₁–C₄)-alkyl,
(m) —S(O)ₙ—(C₁–C₄)-alkyl, or
(n) —NHSO₂R¹¹; and R⁵ᵃ and R⁵ᵇ are independently:
(a) H,
(b) (C₁–C₆)-alkyl, (C₂–C₆)-alkenyl or (C₂–C₆)-alkynyl,
(c) Cl, Br, I, F,
(d) CF₃, or
(e) when R⁵ᵃ and R⁵ᵇ are bonded to adjacent carbon atoms, they can be joined to form a phenyl ring;

R⁶ᵃ and R⁶ᵇ are independently:
(a) H,
(b) aryl-(C₁–C₄)-alkyl,
(c) heteroaryl-(C₁–C₄)-alkyl,
(d) (C₁–C₆)-alkyl, which is unsubstituted or substituted with a substituent selected from the group consisting of: —CON(R³)₂, -heteroaryl, —S(O)ₙ—R¹⁵, -tetrazol-5-yl, —CONHSO₂R¹⁵, —SO₂NH-heteroaryl, —SO₂NHCOR¹⁵, —PO(OR²)₂, —PO(OR³)₂, —SO₂NH—CN, —NR²COOR¹⁵, —OH, —NH₂, guanidino, (C₁–C₄)-alkoxy, (C₁–C₄)-alkylthio, C₁–C₄-alkylamino, (C₁–C₄)-dialkylamino, —COOR³, —CONHR³, —CONHR³, —O—COR³, or aryl,
(e) —CO-aryl,
(f) (C₃–C₇)-cycloalkyl,
(g) Cl, Br, I, F,
(h) —OR¹¹,
(i) —SH,
(j) —S(O)ₙ—(C₁–C₄)-alkyl,
(k) —COR³,
(l) —CO₂H,
(m) —CO₂—(C₁–C₄)-alkyl,
(n) —SO₃H,
(o) —NR²R¹⁵,
(p) —NR²COR¹⁵,
(q) —NR²COOR¹⁵,
(r) —SO₂NHR³,
(s) —SO₂NR²R³,
(t) —NO₂,
(u) —NHSO₂CF₃,
(v) —CONR³R³,
(w) —(C₁–C₄)-perfluoroalkyl,
(x) —COOR²,
(y) —SO₃H,
(z) —N(R²)SO₂R¹⁵,
(aa) —NR²CONR³R¹⁵,
(bb) —OC(=O)NR¹⁵R³,
(cc) -aryl, wherein aryl is phenyl or naphthyl, which is unsubstituted or substituted as defined in R¹(c),
(dd) —NHSO₂CF₃,
(ee) —SO₂NH-heteroaryl, wherein heteroaryl is unsubstituted or substituted as defined in R¹(d),
(ff) —SO₂NHCOR¹⁵,
(gg) —CONHSO₂R¹⁵,
(hh) —PO(OR²)₂,
(ii) -tetrazol-5-yl,
(jj) —CONH(tetrazol-5-yl), or
(kk) —SO₂NHCN; and R⁷ is:
(a) H,
(b) (C₁–C₆)-alkyl, unsubstituted or substituted with:
(i) -aryl,
(ii) —(C₃–C₇)-cycloalkyl,
(iii) —NR³R¹¹,
(iv) -morpholin-4-yl,
(v) —OH,
(vi) —CO₂R³, or
(vii) —CON(R³)₂,
(c) aryl, unsubstituted or substituted with a substituent selected from the group consisting of:
i) (C₁–C₄)-alkyl,
ii) —O—(C₁–C₄)-alkyl,
iii) —CONR³R¹¹,
iv) F, Cl, Br or I, or
v) —COOR³;

R⁸ is:
(a) H,
(b) (C₁–C₄)-alkyl, wherein alkyl is unsubstituted or substituted with one or two substituents selected from the group consisting of:
i) —OH,
ii) —NR³R¹¹,
iii) —COOR³,
iv) —CONHR³, or
v) —CONR³R¹¹;

R⁹ and R¹⁰ are independently:
(a) H,
(b) (C₁–C₆)-alkyl, unsubstituted or substituted with (C₃–C₇)-cycloalkyl,
(c) (C₂–C₆)-alkenyl,
(d) (C₂–C₆)-alkynyl,
(e) Cl, Br, F, I,
(f) (C₁–C₆)-alkoxy,
(g) when R⁹ and R¹⁰ are on adjacent carbons, they can be joined to form a phenyl ring,
(h) perfluoro-(C₁–C₆)-alkyl,
(i) (C₃–C₇)-cycloalkyl, unsubstituted or substituted with (C₁–C₆)-alkyl,
(j) aryl,
(k) (C₁–C₆)-alkyl-S(O)ₙ—(CH₂)ₙ—,
(l) hydroxy-(C₁–C₆)-alkyl or dihydroxy-(C₁–C₆)-alkyl,
(m) —CF₃,
(n) —CO₂R³,
(o) —OH,
(p) —NR³R¹¹,
(q) —[(C₁–C₆)-alkyl]NR³R¹¹,
(r) —NO₂,
(s) —(CH₂)ₙ—SO₂—N(R³)₂,
(t) —NR³CO—(C₁–C₄)-alkyl, or
(u) —CON(R³)₂;

R¹¹ is:
(a) H,
(b) (C₁–C₆)-alkyl,
(c) allyl,
(d) (C₃–C₆)-cycloalkyl,
(e) (C₁–C₄)-acyl,
(f) benzyl, or
(g) phenyl; and R¹², R¹³, R¹⁴ᵃ and R¹⁴ᵇ are independently:
(a) H,
(b) F, Cl, Br, or I,
(c) —NO₂,
(d) —NH₂,
(e) —NH(C₁–C₄)-alkyl,
(f) —N[(C₁–C₄)-alkyl]₂,
(g) —SO₂NHR³,
(h) —CF₃,
(i) (C₁–C₄)-alkyl,
(j) —OR³,
(k) —S(O)ₙ—(C₁–C₄)-alkyl, (l) —NHCO—($C_1$-$C_4$)-alkyl,
(m) —NHCO—O($C_1$-$C_4$)-alkyl,
(n) —$CH_2$O—($C_1$-$C_4$)-alkyl,
(o) —O—($CH_2$)m—$OR^3$,
(p) —$CONR^3R^{11}$, or
(q) —$COOR^3$ and
m is 2, 3, or 4; and
$R^{12}$ and $R^{13}$ on adjacent carbon atoms can be joined together to form a ring structure:

A represents:
a) —Y—$C(R^4)$=$C(R^4)$—,
b) —Y—$C(R^4)$=N—,
c) —Y—N=$C(R^4)$—,
d) —Y—[$C(R^8)(R^8)$]s —Y—,
e) —Y—$C(R^8)(R^8)$—$C(R^8)(R^8)$—,
f) —$C(R^4)$=$C(R^4)$—Y—,
g) —N=$C(R^4)$—Y—,
h) —$C(R^8)(R^8)$—$C(R^8)(R^8)$—Y—, or
i) —$C(R^4)$=$C(R^4)$—$C(R^4)$=$C(R^4)$—; and
s is 1 or 2; and
Y is —O—, —S(O)$_n$— and $NR^3$; and
X is:
(a) —O—,
(b) —S(O)$_n$—,
(c) —$NR^3$—
(d) —$CH_2$O—,
(e) —$CH_2$S(O)$_n$—,
(f) —$CH_2NR^3$—,
(g) —$OCH_2$—,
(h) —$NR^3CH_2$—,
(i) —S(O)$_n$$CH_2$—, or
(j) single bond; and
$R^{15}$ is:
(a) aryl, or
(b) ($C_1$-$C_4$)-alkyl, is unsubstituted or substituted with:
  i) $NH_2$,
  ii) NH[($C_1$-$C_4$)-alkyl],
  iii) N[($C_1$-$C_4$)-alkyl]$_2$,
  iv) $CO_2H$,
  v) $CO_2$($C_1$-$C_4$)-alkyl,
  vi) OH,
  vii) $SO_3H$, or
  viii) $SO_2NH_2$; and
Z is:
(a) —$CO_2H$,
(b) —$CO_2R^{16}$,
(c) -tetrazol-5-yl,
(d) —CONH(tetrazol-5-yl)
(e) —$CONHSO_2$-aryl, wherein aryl is phenyl or naphthyl, which is unsubstituted or substituted as defined in $R^1$(c),
(f) —$CONHSO_2$—($C_1$-$C_8$)-alkyl, wherein the alkyl group is unsubstituted or substituted with a substituent selected from the group consisting of: —OH, —SH, —($C_1$-$C_4$)-alkyl, —S—($C_1$-$C_4$)-alkyl, —$CF_3$, Cl, Br, F, I, —$NO_2$, —$CO_2H$, —$CO_2$—($C_1$-$C_4$)-alkyl, —$NH_2$, —NH[($C_1$-$C_4$)-alkyl], —N[($C_1$-$C_4$)-alkyl]$_2$; and
(g) —$CONHSO_2$—($C_1$-$C_4$)-perfluoroalkyl,
(h) —$CONHSO_2$-heteroaryl, wherein heteroaryl is unsubstituted or substituted as defined in $R^1$(d),
(i) —$CONHSO_2NR^3R^3$,
(j) —$SO_2NHCO$-aryl, wherein aryl is phenyl or naphthyl, which is unsubstituted or substituted as defined in $R^1$(c),
(k) —$SO_2NHCO$—($C_1$-$C_8$)-alkyl, wherein the alkyl group is unsubstituted or substituted with a substituent selected from the group consisting of: —OH, —SH, —O($C_1$-$C_4$)-alkyl, —S—($C_1$-$C_4$)-alkyl, —$CF_3$, Cl, Br, F, I, —$NO_2$, —$CO_2H$, —$CO_2$—($C_1$-$C_4$)-alkyl, —$NH_2$, —NH[($C_1$-$C_4$)-alkyl], —N[($C_1$-$C_4$)-alkyl]$_2$,
(l) —$SO_2NHCO$—($C_1$-$C_4$)-perfluoroalkyl,
(m) —$SO_2NHCO$-heteroaryl, wherein heteroaryl is unsubstituted or substituted as defined in $R^1$(d),
(n) —$SO_2NHCONR^3R^3$,
(o) —$PO(OH)_2$,
(p) —$PO(OR^2)_2$, or
(q) —$PO(OH)(OR^2)$; and
$R^{16}$ is:
(a) ($C_1$-$C_4$)-alkyl,
(b) $CHR^{17}$—O—$COR^{18}$,
(c) $CH_2CH_2$—N[($C_1$-$C_2$)-alkyl]$_2$,
(d) $CH_2CH_2$—N[$CH_2CH_2$]$_2$O,
(e) ($CH_2CH_2O)_y$—O—[($C_1$-$C_4$)-alkyl], wherein y is 1 or 2,
(f) aryl or $CH_2$-aryl, where aryl is as defined above or optionally substituted with $CO_2$($C_1$-$C_4$)-alkyl,

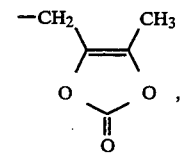 (g)

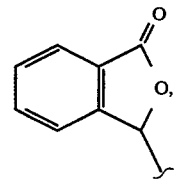 (h)

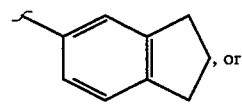 (i)

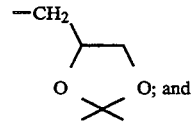 (j)

$R^{17}$ and $R^{18}$ independently are: ($C_1$-$C_6$)-alkyl or phenyl.

An embodiment of the invention is when:
$R^1$ is:
(a) H,
(b) ($C_1$-$C_6$)-alkyl, ($C_2$-$C_6$)-alkenyl or ($C_2$-$C_6$)-alkynyl each of which is unsubstituted or substituted with a substituent selected from the group consisting of:
  i) ($C_3$-$C_7$)-cycloalkyl,
  ii) $CF_3$,
  iii) ($C_1$-$C_4$)-alkylthio,
  iv) ($C_1$-$C_4$)-alkoxy,
(c) ($C_1$-$C_4$)-perfluoroalkyl,
(d) —O—($C_1$-$C_6$)-alkyl, (e) —S(O)$_n$—(C$_1$-C$_9$)-alkyl,
(f) —CONR$^3$R$^3$, or
(g) —NR$^3$CO—O—(C$_1$-C$_4$)-alkyl; and
n is: 0, 1, or 2; and J is: (a) —C(=M)—, (b) J and L are connected together to form a 6-membered aromatic ring substituted with R$^{5a}$, R$^{5b}$, R$^{6a}$ and R$^{6b}$ or (c) J and L are connected together to form a 6-membered aromatic ring containing one nitrogen atom, substituted with R$^{5a}$, R$^{5b}$ and R$^{6b}$; and K is: (a) —C(=M)—, or (b) K and L are connected together to form a 6-membered aromatic ring substituted with R$^{5a}$, R$^{5b}$, R$^{6a}$ and R$^{6b}$, or (c) K and L are connected together to form a six-membered aromatic ring containing one nitrogen atom substituted with R$^{5a}$, R$^{5b}$ and R$^{6b}$ provided that one and only one of J and K is —C(=M)—; and one of a or b is a double bond in Formula I provided that when J is —C(=M)—, then b is a double bond and when K is —C(=M)—, then a is a double bond;

L is: the point of attachment of the 6-membered fused aromatic ring optionally containing one nitrogen atom; and M is: O, S or NR$^{11}$; and
R$^2$ is:
(a) H,
(b) (C$_1$-C$_6$)-alkyl; and
R$^3$ is:
(a) R$^2$,
(b) —CH$_2$-aryl, or
(c) aryl; and
R$^4$ groups are independently:
(a) H,
(b) (C$_1$-C$_6$)-alkyl or (C$_2$-C$_6$)-alkenyl each of which is unsubstituted or substituted with one of the following substituents,
 i) —OH,
 ii) —O—(C$_1$-C$_4$)-alkyl,
 iii) —S(O)$_n$—(C$_1$-C$_4$)-alkyl,
 iv) —NR$^3$—(C$_1$-C$_4$)-alkyl,
 v) —NHR$^3$,
 vi) —COOR$^3$,
 vii) —CONHR$^3$,
 ix) —CONR$^3$R$^{11}$, or
 x) (C$_3$-C$_7$)-cycloalkyl,
(c) (C$_3$-C$_7$)-cycloalkyl,
(d) F, Cl, Br, I,
(e) CF$_3$,
(f) —COOR$^3$,
(g) —CONR$^3$R$^{11}$,
(h) —NR$^3$R$^{11}$,
(i) —NR$^3$CONR$^3$R$^{11}$,
(j) —NR$^3$COOR$^{11}$,
(k) —SO$_2$NR$^3$R$^{11}$,
(l) —O—(C$_1$-C$_4$)-alkyl,
(m) —S(O)$_n$—(C$_1$-C$_4$)-alkyl, or
(n) —NHSO$_2$R$^{11}$; and
R$^{5a}$ and R$^{5b}$ are independently:
(a) H,
(b) (C$_1$-C$_6$)-alkyl, (C$_2$-C$_6$)-alkenyl or (C$_2$-C$_6$)-alkynyl,
(c) Cl, Br, I, F,
(d) CF$_3$, or
(e) when R$^{5a}$ and R$^{5b}$ are bonded to adjacent carbon atoms, they can be joined to form a phenyl ring;
R$^{6a}$ and R$^{6b}$ are independently:
(a) H,
(b) aryl-(C$_1$-C$_4$)-alkyl,
(c) heteroaryl-(C$_1$-C$_4$)-alkyl,
(d) (C$_1$-C$_6$)-alkyl, is unsubstituted or substituted with a substituent selected from the group consisting of: —CON(R$^3$)$_2$, -heteroaryl, —S(O)$_n$—R$^{15}$, -tetrazol-5-yl, —CONHSO$_2$R$^{15}$, —SO$_2$NH-heteroaryl, —SO$_2$NHCOR$^{15}$, —PO(OR$^2$)$_2$, —PO(OR$^3$)$_2$, —SO$_2$NH—CN, —NR$^2$COOR$^{15}$, —OH, —NH$_2$, guanidino, (C$_1$-C$_4$)-alkoxy, (C$_1$-C$_4$)-alkylthio, (C$_1$-C$_4$)-alkylamino, (C$_1$-C$_4$)-dialkylamino, —COOR$^3$, —CONHR$^3$, —O—COR$^3$, or aryl,
(e) —CO-aryl,
(f) (C$_3$-C$_7$)-cycloalkyl,
(g) Cl, Br, I, F,
(h) —OR$^{11}$,
(i) —SH,
(j) —S(O)$_n$—(C$_1$-C$_4$)-alkyl,
(k) —COR$^3$,
(l) —CO$_2$H,
(m) —CO$_2$—(C$_1$-C$_4$)-alkyl,
(n) —SO$_3$H,
(o) —NR$^2$R$^{15}$,
(p) —NR$^2$COR$^{15}$,
(q) —NR$^2$COOR$^{15}$,
(r) —SO$_2$NHR$^3$,
(s) —SO$_2$NR$^2$R$^3$,
(t) —NO$_2$,
(u) —NHSO$_2$CF$_3$,
(v) —CONR$^3$R$^3$,
(w) —(C$_1$-C$_4$)-perfluoroalkyl,
(x) —COOR$^2$,
(y) —SO$_3$H,
(z) —N(R$^2$)SO$_2$R$^{15}$,
(aa) —NR$^2$CONR$^3$R$^{15}$,
(bb) —OC(=O)NR$^{15}$R$^3$,
(cc) -aryl, wherein aryl is phenyl or naphthyl, which is unsubstituted or substituted as defined in R$^1$(c),
(dd) —NHSO$_2$CF$_3$,
(ee) —SO$_2$NH-heteroaryl, wherein heteroaryl is unsubstituted or substituted as defined in R$^1$(d),
(ff) —SO$_2$NHCOR$^{15}$,
(gg) —CONHSO$_2$R$^{15}$,
(hh) —PO(OR$^2$)$_2$,
(ii) -tetrazol-5-yl,
(jj) —CONH(tetrazol-5-yl), or
(kk) —SO$_2$NHCN; and
R$^7$ is:
(a) H,
(b) (C$_1$-C$_6$)-alkyl, unsubstituted or substituted with:
 (i) -aryl,
 (ii) —(C$_3$-C$_7$)-cycloalkyl,
 (iii) —NR$^3$R$^{11}$,
 (iv) -morpholin-4-yl,
 (v) —OH,
 (vi) —CO$_2$R$^3$, or
 (vii) —CON(R$^3$)$_2$,
(c) aryl, unsubstituted or substituted with a substituent selected from the group consisting of:
 i) (C$_1$-C$_4$)-alkyl,
 ii) —O—(C$_1$-C$_4$)-alkyl,
 iii) —CONR$^3$R$^{11}$,
 iv) F, Cl, Br or I, or
 v) —COOR$^3$;
R$^9$ and R$^{10}$ are independently:
(a) H,
(b) (C$_1$-C$_6$)-alkyl, unsubstituted or substituted with (C$_3$-C$_7$)-cycloalkyl,
(c) (C$_2$-C$_6$)-alkenyl,
(d) (C$_2$-C$_6$)-alkynyl, (e) Cl, Br, F, I,
(f) $(C_1-C_6)$-alkoxy,
(g) when $R^9$ and $R^{10}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) aryl,
(k) $(C_1-C_6)$-alkyl-$S(O)_n$—$(CH_2)_n13$,
(l) hydroxy-$(C_1-C_6)$-alkyl or dihydroxy-$(C_1-C_6)$-alkyl,
(m) —$CF_3$,
(n) —$CO_2R^3$,
(o) —OH,
(p) —$NR^3R^{11}$,
(q) —$[(C_1-C_6)$-alkyl$]NR^3R^{11}$,
(r) —$NO_2$,
(s) —$(CH_2)_n$—$SO_2$—$N(R^3)_2$,
(t) —$NR^3CO$—$(C_1-C_4)$-alkyl, or
(u) —$CON(R^3)_2$;

$R^{12}$, $R^{13}$, $R^{14a}$ and $R^{14b}$ are independently:
(a) H,
(b) F, Cl, Br, or I,
(c) —$NO_2$,
(d) —$NH_2$,
(e) —$NH(C_1-C_4)$-alkyl,
(f) —$N[(C_1-C_4)$-alkyl$]_2$,
(g) —$SO_2NHR^3$,
(h) —$CF_3$,
(i) $(C_1-C_4)$-alkyl,
(j) —$OR^3$,
(k) —$S(O)_n$—$(C_1-C_4)$-alkyl,
(l) —NHCO—$(C_1-C_4)$-alkyl,
(m) —NHCO—$O(C_1-C_4)$-alkyl,
(n) —$CH_2O$—$(C_1-C_4)$-alkyl,
(o) —O—$(CH_2)m$—$OR^3$,
(p) —$CONR^3R^{11}$, or
(q) —$COOR^3$ and
m is 2, 3, or 4; and
$R^{12}$ and $R^{13}$ on adjacent carbon atoms can be joined together to form a ring structure:

A represents:
a) —Y—$C(R^4)=C(R^4)$—,
b) —Y—$C(R^4)=N$—,
c) —Y—$N=C(R^4)$—,
d) —Y—$[C(R^8)(R^8)]s$ —Y—,
e) —Y—$C(R^8)(R^8)$—$C(R^8)(R^8)$—,
f) —$C(R^4)=C(R^4)$—Y—,
g) —$N=C(R^4)$—Y—,
h) —$C(R^8)(R^8)$—$C(R^8)(R^8)$—Y—, or
i) —$C(R^4)=C(R^4)$—$C(R^4)=C(R^4)$—; and
s is 1 or 2; and
Y is —O—, —$S(O)_n$— and $NR^3$; and
X is:
(a) —O—,
(b) —$S(O)_n$—,
(c) —$NR^3$—,
(d) —$CH_2O$—,
(e) —$CH_2S(O)_n$—,
(f) —$CH_2NR^3$—,
(g) —$OCH_2$—,
(h) —$NR^3CH_2$—,
(i) —$S(O)_nCH_2$—, or
(j) single bond; and $R^{15}$ is:
(a) aryl, or
(b) $(C_1-C_4)$-alkyl, is unsubstituted or substituted with:
  i) $NH_2$,
  ii) $NH[(C_1-C_4)$-alkyl$]$,
  iii) $N[(C_1-C_4)$-alkyl$]_2$,
  iv) $CO_2H$,
  v) $CO_2(C_1-C_4)$-alkyl,
  vi) OH,
  vii) $SO_3H$, or
  viii) $SO_2NH_2$; and Z is:
(a) —$CO_2H$,
(b) —$CO_2R^{16}$,
(c) -tetrazol-5-yl,
(d) —CONH(tetrazol-5-yl),
(e) —$CONHSO_2$-aryl, wherein aryl is phenyl or naphthyl, which is unsubstituted or substituted as defined in $R^1(c)$,
(f) —$CONHSO_2$—$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —$NH[(C_1-C_4)$-alkyl$]$, —$N[(C_1-C_4)$-alkyl$]_2$; and
(g) —$CONHSO_2$—$(C_1-C_4)$-perfluoroalkyl,
(h) —$CONHSO_2$-heteroaryl, wherein heteroaryl is unsubstituted or substituted as defined in $R^1(d)$,
(i) —$CONHSO_2NR^3R^3$,
(j) —$SO_2NHCO$-aryl, wherein aryl is phenyl or naphthyl, which is unsubstituted or substituted as defined in $R^1(c)$,
(k) —$SO_2NHCO$—$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —$NH[(C_1-C_4)$-alkyl$]$, —$N[(C_1-C_4)$-alkyl$]_2$; and
(l) —$SO_2NHCO$—$(C_1-C_4)$-perfluoroalkyl,
(m) —$SO_2NHCO$-heteroaryl, wherein heteroaryl is unsubstituted or substituted as defined in $R^1(d)$, or
(n) —$SO_2NHCONR^3R^3$; and $R^{16}$ is:
(a) $(C_1-C_4)$-alkyl,
(b) $CHR^{17}$—O—$COR^{18}$,
(c) $CH_2CH_2$—$N[(C_1-C_2)$-alkyl$]_2$,
(d) $CH_2CH_2$—$N[CH_2CH_2]_2O$,
(e) $(CH_2CH_2O)_y$—O—$[(C_1-C_4)$-alkyl$]$, wherein y is 1 or 2,
(f) aryl or $CH_2$-aryl, where aryl is as defined above or optionally substituted with $CO_2(C_1-C_4)$-alkyl,

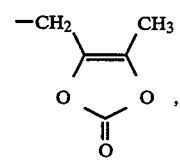

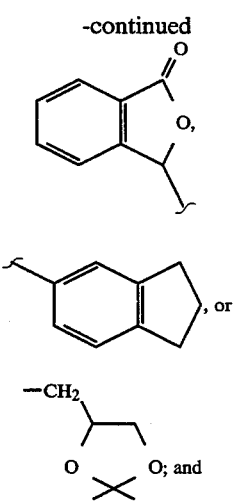

$R^{17}$ and $R^{18}$ independently are: $(C_1-C_6)$-alkyl or phenyl.

A class of this embodiment of the invention is when:
$R^1$ is:
(a) H,
(b) $(C_1-C_6)$-alkyl, $(C_2-C_6)$-alkenyl or $(C_2-C_6)$-alkynyl each of which is unsubstituted or substituted with a substituent selected from the group consisting of:
  i) $(C_3-C_7)$-cycloalkyl,
  ii) $CF_3$,
  iii) $(C_1-C_4)$-alkylthio,
  iv) $(C_1-C_4)$-alkoxy,
(c) $(C_1-C_4)$-perfluoroalkyl,
(d) —$CONR^3R^3$, or
(e) —$NR^3CO$—O—$(C_1-C_4)$-alkyl; and
n is: 0, 1, or 2; and J is: (a) —C(=M)—, or (b) J and L are connected together to form a 6-membered aromatic ring substituted with $R^{5a}$, $R^{5b}$, $R^{6a}$ and $R^{6b}$;

K is: (a) —C(=M)—, or (b) K and L are connected together to form a 6-membered aromatic ring substituted with $R^{5a}$, $R^{5b}$, $R^{6a}$ and $R^{6b}$, provided that one and only one of J and K is —C(=M)—; and one of a or b is a double bond in Formula I provided that when J is —C(=M)—, then b is a double bond and when K is —C(=M)—, then a is a double bond;

L is: the point of attachment of the 6-membered fused aromatic ring optionally containing one nitrogen atom; and M is: O, S or $NR^{11}$; and
$R^2$ is:
(a) H,
(b) $(C_1-C_6)$-alkyl; and
$R^3$ is:
(a) $R^2$,
(b) —$CH_2$-aryl, or
(c) aryl; and
$R^4$ groups are independently:
(a) H,
(b) $(C_1-C_6)$-alkyl or $(C_2-C_6)$-alkenyl each of which is unsubstituted or substituted with one of the following substituents,
  i) —OH,
  ii) —O—$(C_1-C_4)$-alkyl,
  iii) —$S(O)_n$—$(C_1-C_4)$-alkyl,
  iv) —$NR^3$—$(C_1-C_4)$-alkyl,
  v) —$NHR^3$,
  vi) —$COOR^3$,
  vii) —$CONHR^3$,
  ix) —$CONR^3R^{11}$, or
  x) $(C_3-C_7)$-cycloalkyl,
(c) $(C_3-C_7)$-cycloalkyl,
(d) F, Cl, Br, I,
(e) $CF_3$,
(f) —$COOR^3$,
(g) —$CONR^3R^{11}$,
(h) —$NR^3R^{11}$,
(i) —$NR^3CONR^3R^{11}$,
(j) —$NR^3COOR^{11}$,
(k) —$SO_2NR^3R^{11}$,
(l) —O—$(C_1-C_4)$-alkyl,
(m) —$S(O)_n$—$(C_1-C_4)$-alkyl, or
(n) —$NHSO_2R^{11}$; and
$R^{5a}$ and $R^{5b}$ are independently:
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{5a}$ and $R^{5b}$ are bonded to adjacent carbon atoms, they can be joined to form a phenyl ring;
$R^{6a}$ and $R^{6b}$ are independently:
(a) H,
(b) aryl-$(C_1-C_4)$-alkyl,
(c) heteroaryl-$(C_1-C_4)$-alkyl,
(d) $(C_1-C_6)$-alkyl, is unsubstituted or substituted with a substituent selected from the group consisting of: —$CON(R^3)_2$, -heteroaryl, —$S(O)_n$—$R^{15}$, -tetrazol-5-yl, —$CONHSO_2R^{15}$, —$SO_2NH$-heteroaryl, —$SO_2NHCOR^{15}$, —$PO(OR^2)_2$, —$PO(OR^3)_2$, —$SO_2NH$—CN, —$NR^2COOR^{15}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^3$, —$CONHR^3$, —O—$COR^3$, or aryl,
(e) —CO-aryl,
(f) $(C_3-C_7)$-cycloalkyl,
(g) Cl, Br, I, F,
(h) —$OR^{11}$,
(i) —SH,
(j) —$S(O)_n$—$(C_1-C_4)$-alkyl,
(k) —$COR^3$,
(l) —$CO_2H$,
(m) —$CO_2$—$(C_1-C_4)$-alkyl,
(n) —$SO_3H$,
(o) —$NR^2R^{15}$,
(p) —$NR^2COR^{15}$,
(q) —$NR^2COOR^{15}$,
(r) —$SO_2NHR^3$,
(s) —$SO_2NR^2R^3$,
(t) —$NO_2$,
(u) —$NHSO_2CF_3$,
(v) —$CONR^3R^3$,
(w) —$(C_1-C_4)$-perfluoroalkyl,
(x) —$COOR^2$,
(y) —$SO_3H$,
(z) —$N(R^2)SO_2R^{15}$,
(aa) —$NR^2CONR^3R^{15}$,
(bb) —$OC(=O)NR^{15}R^3$,
(cc) -aryl, wherein aryl is phenyl or naphthyl, which is unsubstituted or substituted as defined in $R^1$(c),
(dd) —$NHSO_2CF_3$,
(ee) —$SO_2NH$-heteroaryl, wherein heteroaryl is unsubstituted or substituted as defined in $R^1$(d),
(ff) —$SO_2NHCOR^{15}$,
(gg) —$CONHSO_2R^{15}$, (hh) —PO(OR$^2$)$_2$,
(ii) -tetrazol-5-yl,
(jj) —CONH(tetrazol-5-yl), or
(kk) —SO$_2$NHCN; and R$^7$ is:
(a) H,
(b) (C$_1$-C$_6$)-alkyl, unsubstituted or substituted with:
  (i) -aryl,
  (ii) —(C$_3$-C$_7$)-cycloalkyl,
  (iii) —NR$^3$R$^{11}$,
  (iv) -morpholin-4-yl,
  (v) —OH,
  (vi) —CO$_2$R$^3$, or
  (vii) —CON(R$^3$)$_2$,
(c) aryl, unsubstituted or substituted with a substituent selected from the group consisting of:
  i) (C$_1$-C$_4$)-alkyl,
  ii) —O—(C$_1$-C$_4$)-alkyl,
  iii) —CONR$^3$R$^{11}$,
  iv) F, Cl, Br or I, or
  v) —COOR$^3$;

R$^9$ and R$^{10}$ are independently:
(a) H,
(b) (C$_1$-C$_6$)-alkyl, unsubstituted or substituted with (C$_3$-C$_7$)-cycloalkyl,
(c) Cl, Br, F, I,
(d) (C$_1$-C$_6$)-alkoxy, or
(e) hydroxy-(C$_1$-C$_6$)-alkyl or dihydroxy-(C$_1$-C$_6$)-alkyl;

R$^{12}$, R$^{13}$, R$^{14a}$, and R$^{14b}$ are independently:
(a) H,
(b) F, Cl, Br, or I,
(c) —NO$_2$,
(d) (C$_1$-C$_4$)-alkyl,
(e) —OR$^3$,
(f) —S(O)$_n$—(C$_1$-C$_4$)-alkyl,
(g) —NHCO—(C$_1$-C$_4$)-alkyl,
(h) —NHCO—O(C$_1$-C$_4$)-alkyl,
(i) —O—(CH$_2$)$_m$—OR$^3$,
(j) —CONR$^3$R$^{11}$, or
(k) —COOR$^3$ and
m is 2, 3, or 4; and R$^{12}$ and R$^{13}$ on adjacent carbon atoms can be joined together to form a ring structure:

A represents:
a) —O—C(R$^4$)=C(R$^4$)—,
b) —O—C(R$^4$)=N—,
c) —O—[C(R$^8$)(R$^8$)]$_s$—O—,
d) —C(R$^4$)=C(R$^4$)—O—,
e) —N=C(R$^4$)—O—, or
f) —C(R$^4$)=C(R$^4$)—C(R$^4$)=C(R$^4$)—; and
s is 1 or 2; and X is:
(a) —O—,
(b) —S(O)$_n$—, or
(c) —NR$^3$—; and R$^{15}$ is:
(a) aryl, or
(b) (C$_1$-C$_4$)-alkyl, is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$; and Z is:
(a) —CO$_2$H,
(b) -tetrazol-5-yl,
(c) —CONH(tetrazol-5-yl),
(d) —CONHSO$_2$-phenyl or —CONHSO$_2$-naphthyl, wherein phenyl or naphthyl is unsubstituted or substituted as defined in R$^1$(c), or
(e) —CONHSO$_2$-heteroaryl, wherein heteroaryl is unsubstituted or substituted as defined in R$^1$(d).

Another class of this embodiment of the invention is a compound of Formula II

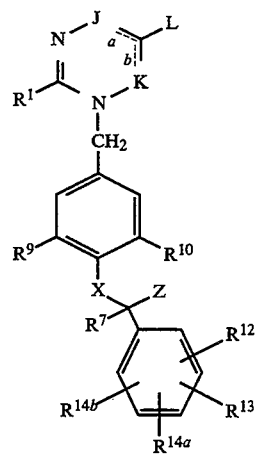

wherein:
R$^1$ is:
(a) H,
(b) (C$_1$-C$_6$)-alkyl, (C$_2$-C$_6$)-alkenyl or (C$_2$-C$_6$)-alkynyl each of which is unsubstituted or substituted with a substituent selected from the group consisting of:
  i) (C$_3$-C$_7$)-cycloalkyl,
  ii) CF$_3$,
  iii) (C$_1$-C$_4$)-alkylthio,
  iv) (C$_1$-C$_4$)-alkoxy,
(c) (C$_1$-C$_4$)-perfluoroalkyl,
(d) —CONR$^3$R$^3$, or
(e) —NR$^3$CO—O—(C$_1$-C$_4$)-alkyl; and
n is: 0, 1, or 2; and J is: (a) —C(=M)—, or (b) J and L are connected together to form a 6-membered aromatic ring substituted with R$^{5a}$, R$^{5b}$, R$^{6a}$ and R$^{6b}$;

K is: (a) —C(=M)—, or (b) K and L are connected together to form a 6-membered aromatic ring substituted with R$^{5a}$, R$^{5b}$, R$^{6a}$ and R$^{6b}$, provided that one and only one of J and K is —C(=M)—; and one of a or b is a double bond in Formula I provided that when J is —C(=M)—, then b is a double bond and when K is —C(=M)—, then a is a double bond;

L is: the point of attachment of the 6-membered fused aromatic ring optionally containing one nitrogen atom; and M is: O, S or NR$^{11}$; and R$^2$ is:
(a) H,
(b) (C$_1$-C$_6$)-alkyl; and $R^3$ is:
(a) $R^2$,
(b) —$CH_2$-aryl, or
(c) aryl; and $R^4$ groups are independently:
(a) H,
(b) ($C_1$-$C_6$)-alkyl or ($C_2$-$C_6$)-alkenyl each of which is unsubstituted or substituted with one of the following substituents,
  i) —OH,
  ii) —O—($C_1$-$C_4$)-alkyl,
  iii) —S(O)$_n$—($C_1$-$C_4$)-alkyl,
  iv) —$NR^3$—($C_1$-$C_4$)-alkyl,
  v) —$NHR^3$,
  vi) —$COOR^3$,
  vii) —$CONHR^3$,
  ix) —$CONR^3R^{11}$, or
  x) ($C_3$-$C_7$)-cycloalkyl,
(c) ($C_3$-$C_7$)-cycloalkyl,
(d) F, Cl, Br, I,
(e) $CF_3$,
(f) —$COOR^3$,
(g) —$CONR^3R^{11}$,
(h) —$NR^3R^{11}$,
(i) —$NR^3CONR^3R^{11}$,
(j) —$NR^3COOR^{11}$,
(k) —$SO_2NR^3R^{11}$,
(l) —O—($C_1$-$C_4$)-alkyl,
(m) —S(O)$_n$—($C_1$-$C_4$)-alkyl, or
(n) —$NHSO_2R^{11}$; and $R^{5a}$ and $R^{5b}$ are independently:
(a) H,
(b) ($C_1$-$C_6$)-alkyl, ($C_2$-$C_6$)-alkenyl or ($C_2$-$C_6$)-alkynyl,
(c) Cl, Br, I, F,
(d) $CF_3$, or
(e) when $R^{5a}$ and $R^{5b}$ are bonded to adjacent carbon atoms, they can be joined to form a phenyl ring;

$R^{6a}$ and $R^{6b}$ are independently:
(a) H,
(b) aryl-($C_1$-$C_4$)-alkyl,
(c) heteroaryl-($C_1$-$C_4$)-alkyl,
(d) ($C_1$-$C_6$)-alkyl, is unsubstituted or substituted with a substituent selected from the group consisting of: —CON($R^3$)$_2$, -heteroaryl, —S(O)$_n$—$R^{15}$, -tetrazol-5-yl, —$CONHSO_2R^{15}$, —$SO_2NH$-heteroaryl, —$SO_2NHCOR^{15}$, —PO(O$R^2$)$_2$, —PO(O$R^3$)$_2$, —$SO_2NH$—CN, —$NR^2COOR^{15}$, —OH, —$NH_2$, guanidino, ($C_1$-$C_4$)-alkoxy, $C_1$-$C_4$)-alkylthio, ($C_1$-$C_4$)-alkylamino, ($C_1$-$C_4$)-dialkylamino, —$COOR^3$, —$CONHR^3$, —O—$COR^3$, or aryl,
(e) —CO-aryl,
(f) ($C_3$-$C_7$)-cycloalkyl,
(g) Cl, Br, I, F,
(h) —$OR^{11}$,
(i) —SH,
(j) —S(O)$_n$—($C_1$-$C_4$)-alkyl,
(k) —$COR^3$,
(l) —$CO_2H$,
(m) —$CO_2$—($C_1$-$C_4$)-alkyl,
(n) —$SO_3H$,
(o) —$NR^2R^{15}$,
(p) —$NR^2COR^{15}$,
(q) —$NR^2COOR^{15}$,
(r) —$SO_2NHR^3$,
(s) —$SO_2NR^2R^3$,
(t) —$NO_2$,
(u) —$NHSO_2CF_3$,
(v) —$CONR^3R^3$,
(w) —($C_1$-$C_4$)-perfluoroalkyl,
(x) —$COOR^2$,
(y) —$SO_3H$,
(z) —$N(R^2)SO_2R^{15}$,
(aa) —$NR^2CONR^3R^{15}$,
(bb) —OC(=O)$NR^{15}R^3$,
(cc) -aryl, wherein aryl is phenyl or naphthyl, which is unsubstituted or substituted as defined in $R^1$(c),
(dd) —$NHSO_2CF_3$,
(ee) —$SO_2NH$-heteroaryl, wherein heteroaryl is unsubstituted or substituted as defined in $R^1$(d),
(ff) —$SO_2NHCOR^{15}$,
(gg) —$CONHSO_2R^{15}$,
(hh) —PO(O$R^2$)$_2$,
(ii) -tetrazol-5-yl,
(jj) —CONH(tetrazol-5-yl), or
(kk) —$SO_2NHCN$; and $R^7$ is:
(a) H,
(b) ($C_1$-$C_6$)-alkyl, unsubstituted or substituted with:
  (i) -aryl,
  (ii) —($C_3$-$C_7$)-cycloalkyl,
  (iii) —$NR^3R^{11}$,
  (iv) -morpholin-4-yl,
  (v) —OH,
  (vi) —$CO_2R^3$, or
  (vii) —CON($R^3$)$_2$,
(c) aryl, unsubstituted or substituted with a substituent selected from the group consisting of:
  i) ($C_1$-$C_4$)-alkyl,
  ii) —O—($C_1$-$C_4$)-alkyl,
  iii) —$CONR^3R^{11}$,
  iv) F, Cl, Br or I, or
  v) —$COOR^3$;

$R^9$ and $R^{10}$ are independently:
(a) H,
(b) ($C_1$-$C_6$)-alkyl, unsubstituted or substituted with ($C_3$-$C_7$)-cycloalkyl,
(c) Cl, Br, F, I,
(d) ($C_1$-$C_6$)-alkoxy, or
(e) hydroxy-($C_1$-$C_6$)-alkyl or dihydroxy-($C_1$-$C_6$)-alkyl;

$R^{12}$, $R^{13}$, $R^{14a}$ and $R^{14b}$ are independently:
(a) H,
(b) F, Cl, Br, or I,
(c) —$NO_2$,
(d) ($C_1$-$C_4$)-alkyl,
(e) —$OR^3$,
(f) —S(O)$_n$—($C_1$-$C_4$)-alkyl,
(g) —NHCO—($C_1$-$C_4$)-alkyl,
(h) —NHCO—O($C_1$-$C_4$)-alkyl,
(i) —O—($CH_2$)$_m$—$OR^3$,
(j) —$CONR^3R^{11}$, or
(k) —$COOR^3$ and
m is 2, 3, or 4; and $R^{12}$ and $R^{13}$ on adjacent carbon atoms can be joined together to form a ring structure:

A represents:
a) —O—C($R^4$)=C($R^4$)—,
b) —O—C($R^4$)=N—,
c) —O—[C($R^8$)($R^8$)]s—O—, d) —C(R$^4$)═C(R$^4$)—O—,
e) —N═C(R$^4$)—O—, or
f) —C(R$^4$)═C(R$^4$)—C(R$^4$)═C(R$^4$)—; and
s is 1 or 2; and
X is:
(a) —O—,
(b) —S(O)$_n$—, or
(c) —NR$^3$—; and
R$^{15}$ is:
(a) aryl, or
(b) (C$_1$–C$_4$)-alkyl, is unsubstituted or substituted with:
  i) NH$_2$,
  ii) NH[(C$_1$–C$_4$)-alkyl],
  iii) N[(C$_1$–C$_4$)-alkyl]$_2$,
  iv) CO$_2$H,
  v) CO$_2$(C$_1$–C$_4$)-alkyl,
  vi) OH,
  vii) SO$_3$H, or
  viii) SO$_2$NH$_2$; and
Z is:
(a) —CO$_2$H,
(b) -tetrazol-5-yl,
(c) —CONH(tetrazol-5-yl),
(d) —CONHSO$_2$-phenyl or —CONHSO$_2$-naphthyl, wherein phenyl or naphthyl is unsubstituted or substituted as defined in R$^1$(c), or
(e) —CONHSO$_2$-heteroaryl, wherein heteroaryl is unsubstituted or substituted as defined in R$^1$(d).

Another class of this embodiment of the invention is a compound of Formula III:

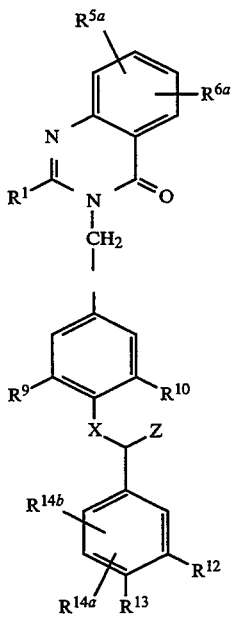

III

R$^1$ is:
(a) H,
(b) (C$_1$–C$_6$)-alkyl, (C$_2$–C$_6$)-alkenyl or (C$_2$–C$_6$)-alkynyl each of which is unsubstituted or substituted with a substituent selected from the group consisting of:
  i) (C$_3$–C$_7$)-cycloalkyl,
  ii) CF$_3$,
  iii) (C$_1$–C$_4$)-alkylthio,
  iv) (C$_1$–C$_4$)-alkoxy,
(c) (C$_1$–C$_4$)-perfluoroalkyl,
(d) —CONR$^3$R$^3$, or
(e) —NR$^3$CO—O—(C$_1$–C$_4$)-alkyl; and
n is: 0, 1, or 2; and
R$^2$ is:
(a) H,
(b) (C$_1$–C$_6$)-alkyl; and
R$^3$ is:
(a) R$^2$,
(b) —CH$_2$-aryl, or
(c) aryl; and
R$^4$ groups are independently:
(a) H,
(b) (C$_1$–C$_6$)-alkyl or (C$_2$–C$_6$)-alkenyl each of which is unsubstituted or substituted with one of the following substituents,
  i) —OH,
  ii) —O—(C$_1$–C$_4$)-alkyl,
  iii) —S(O)$_n$—(C$_1$–C$_4$)-alkyl,
  iv) —NR$^3$—(C$_1$–C$_4$)-alkyl,
  v) —NHR$^3$,
  vi) —COOR$^3$,
  vii) —CONHR$^3$,
  ix) —CONR$^3$R$^{11}$, or
  x) (C$_3$–C$_7$)-cycloalkyl,
(c) (C$_3$–C$_7$)-cycloalkyl,
(d) F, Cl, Br, I,
(e) CF$_3$,
(f) —COOR$^3$,
(g) —CONR$^3$R$^{11}$,
(h) —NR$^3$R$^{11}$,
(i) —NR$^3$CONR$^3$R$^{11}$,
(j) —NR$^3$COOR$^{11}$,
(k) —SO$_2$NR$^3$R$^{11}$,
(l) —O—(C$_1$–C$_4$)-alkyl,
(m) —S(O)$_n$—(C$_1$–C$_4$)-alkyl, or
(n) —NHSO$_2$R$^{11}$; and
R$^{5a}$ is:
(a) H,
(b) (C$_1$–C$_6$)-alkyl, (C$_2$–C$_6$)-alkenyl or (C$_2$–C$_6$)-alkynyl,
(c) Cl, Br, I, F,
(d) CF$_3$, or
(e) when R$^{5a}$ and R$^{5b}$ are bonded to adjacent carbon atoms, they can be joined to form a phenyl ring;
R$^{6a}$ is:
(a) H,
(b) aryl-(C$_1$–C$_4$)-alkyl,
(c) heteroaryl-(C$_1$–C$_4$)-alkyl,
(d) (C$_1$–C$_6$)-alkyl, is unsubstituted or substituted with a substituent selected from the group consisting of: —CON(R$^3$)$_2$, -heteroaryl, —S(O)$_n$—R$^{15}$, -tetrazol-5-yl, —CONHSO$_2$R$^{15}$, —SO$_2$NH-heteroaryl, —SO$_2$NHCOR$^{15}$, —PO(OR$^2$)$_2$, —PO(OR$^3$)$_2$, —SO$_2$NH—CN, —NR$^2$COOR$^{15}$, —OH, —NH$_2$, guanidino, (C$_1$–C$_4$)-alkoxy, (C$_1$–C$_4$)-alkylthio, (C$_1$–C$_4$)-alkylamino, (C$_1$–C$_4$)-dialkylamino, —COOR$^3$, —CONHR$^3$, —O—COR$^3$, or aryl,
(e) —CO-aryl,
(f) (C$_3$–C$_7$)-cycloalkyl,
(g) Cl, Br, I, F,
(h) —OR$^{11}$,
(i) —SH,
(j) —S(O)$_n$—(C$_1$–C$_4$)-alkyl,
(k) —COR$^3$,
(l) —CO$_2$H,
(m) —CO$_2$—(C$_1$–C$_4$)-alkyl,
(n) —SO$_3$H,
(o) —NR$^2$R$^{15}$,
(p) —NR$^2$COR$^{15}$, (q) —NR²COOR¹⁵,
(r) —SO₂NHR³,
(s) —SO₂NR²R³,
(t) —NO₂,
(u) —NHSO₂CF₃,
(v) —CONR³R³,
(w) —(C₁-C₄)-perfluoroalkyl,
(x) —COOR²,
(y) —SO₃H,
(z) —N(R²)SO₂R¹⁵,
(aa) —NR²CONR³R¹⁵,
(bb) —OC(=O)NR¹⁵R³,
(cc) -aryl, wherein aryl is phenyl or naphthyl, which is unsubstituted or substituted as defined in R¹(c),
(dd) —NHSO₂CF₃,
(ee) —SO₂NH-heteroaryl, wherein heteroaryl is unsubstituted or substituted as defined in R¹(d),
(ff) —SO₂NHCOR¹⁵,
(gg) —CONHSO₂R¹⁵,
(hh) —PO(OR²)₂,
(ii) -tetrazol-5-yl,
(jj) —CONH(tetrazol-5-yl), or
(kk) —SO₂NHCN; and
R⁹ and R¹⁰ are independently:
(a) H,
(b) (C₁-C₆)-alkyl, unsubstituted or substituted with (C₃-C₇)-cycloalkyl,
(c) Cl, Br, F, I,
(d) (C₁-C₆)-alkoxy, or
(e) hydroxy-(C₁-C₆)-alkyl or dihydroxy-(C₁-C₆)-alkyl;
R¹², R¹³, R¹⁴ᵃ and R¹⁴ᵇ are independently:
(a) H,
(b) F, Cl, Br, or I,
(c) —NO₂,
(d) (C₁-C₄)-alkyl,
(e) —OR³,
(f) —S(O)ₙ—(C₁-C₄)-alkyl,
(g) —NHCO—(C₁-C₄)-alkyl,
(h) —NHCO—O(C₁-C₄)-alkyl,
(i) —O—(CH₂)m—OR³,
(j) —CONR³R¹¹, or
(k) —COOR³ and
m is 2, 3, or 4; and
R¹² and R¹³ on adjacent carbon atoms can be joined together to form a ring structure:

A represents:
a) —O—C(R⁴)=C(R⁴)—,
b) —O—C(R⁴)=N—,
c) —O—[C(R⁸)(R⁸)]s —O—,
d) —C(R⁴)=C(R⁴)—O—,
e) —N=C(R⁴)—O—, or
f) —C(R⁴)=C(R⁴)—C(R⁴)=C(R⁴)—; and
s is 1 or 2; and
X is:
(a) —O—,
(b) —S(O)ₙ—, or
(c) —NR³—; and
R¹⁵ is:
(a) aryl, or
(b) (C₁-C₄)-alkyl, is unsubstituted or substituted with:
  i) NH₂,
  ii) NH[(C₁-C₄)-alkyl],
  iii) N[(C₁-C₄)-alkyl]₂,
  iv) CO₂H,
  v) CO₂(C₁-C₄)-alkyl,
  vi) OH,
  vii) SO₃H, or
  viii) SO₂NH₂; and
Z is:
(a) —CO₂H,
(b) -tetrazol-5-yl,
(c) —CONH(tetrazol-5-yl),
(d) —CONHSO₂-phenyl or —CONHSO₂-naphthyl, wherein phenyl or naphthyl is unsubstituted or substituted as defined in R¹(c), or
(e) —CONHSO₂-heteroaryl, wherein heteroaryl is as defined in R¹(d).

The following Table further exemplifies the scope of the invention wherein the structural formula is:

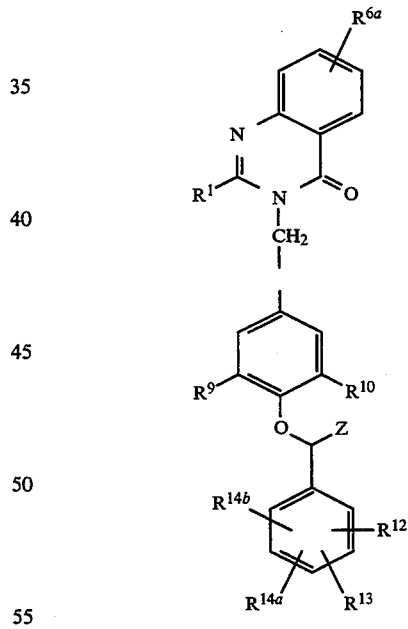

and the substituents are as defined in the table below:

| R¹ | R⁶ᵃ | R⁹ | R¹⁰ | R¹²,R¹³,R¹⁴ᵃ,R¹⁴ᵇ | Z |
|---|---|---|---|---|---|
| Bu | 6-Me | H | Allyl | H, H, H, H | COOH |
| Bu | 6-Me | H | Pr | H, H, H, H | COOH |
| Bu | 6-Me | H | ci | H, H, H, H | COOH |
| Pr | 6-N(Me)COOiBu | OMe | Cl | H, H, H, H | COOH |
| Pr | 6-N(Me)COOiBu | H | Pr | H, H, H, H | COOH |
| Pr | 6-Me | Pr | Pr | 2-Br, 5-Br, 3-OMe, 4-OMe | COOH |
| H | 8-Me | Pr | Pr | 2-Br, 5-Br, 3-OMe, 4-OMe | COOH |
| Me | 8-Me | Me | Me | 3-OMe, 5-OMe | COOH |
| H | 8-Me | H | Pr | 3-OMe, 5-OMe | COOH |
| H | 8-Me | Pr | Pr | 3-OMe, 5-OMe | COOH |

-continued

| R$^1$ | R$^{6a}$ | R$^9$ | R$^{10}$ | R$^{12}$,R$^{13}$,R$^{14a}$,R$^{14b}$ | Z |
|---|---|---|---|---|---|
| H | 8-Me | H | Pr | 3-OMe, 5-OMe | CONHSO$_2$Ph |
| H | 8-Me | Pr | Pr | 3-OMe, 5-OMe | CONHSO$_2$Me |
| H | 8-Me | H | Pr | 3-OMe, 5-OMe | CONHSO$_2$Ph(4-iPr) |
| i-Pr | 8-Br | H | Pr | 3-OMe, 5-OMe | CONHSO$_2$Ph(4-iPr) |
| H | 6-PhCONH | Bu | H | 3-OMe | COOH |
| Me | 8-Me | Pr | H | 3-OMe | COOH |
| Me | 8-Me | Pr | H | 3-OMe | CONHSO$_2$Ph(4-iPr) |
| Me | 8-Me | Pr | Pr | 3-OMe | COOH |
| H | 8-Me | ci | ci | 3-OMe | COOH |
| Me | 8-Me | Br | Br | 3-OMe | COOH |
| Ph | 8-Me | ci | ci | 3-OMe | COOH |
| H | 8-Me | Pr | Pr | 4-OMe | COOH |
| Me | 6-Me | Pr | Pr | 4-OMe | COOH |
| i-Pr | 8-Me | Pr | H | 4-OMe | COOH |
| Bu | 6-Me | ci | ci | 4-OMe | COOH |
| Me | 8-Me | Br | Br | 4-OMe | COOH |
| H | 8-Me | Pr | Pr | 2-OMe | COOH |
| Me | 6-Me | Pr | Pr | 2-OMe, 3-OMe | COOH |
| i-Pr | 8-Me | Pr | H | 2-OMe | COOH |
| Bu | 6-Me | ci | ci | 2-OMe | COOH |
| Me | 8-Me | Br | Br | 2-OMe | COOH |
| H | 8-Me | H | Pr | 3-OMe, 4-OMe | COOH |
| H | 8-Me | Pr | Pr | 3-OMe, 4-OMe | COOH |
| H | 8-Me | H | Pr | 3-OMe, 4-OMe | CONHSO$_2$Ph |
| H | 8-Me | Pr | Pr | 3-OMe, 4-OMe | CONHSO$_2$Me |
| H | 8-Me | H | Pr | 3-OMe, 4-OMe | CONHSO$_2$Ph(4-iPr) |
| i-Pr | 8-Br | H | Pr | 3-OMe, 4-OMe | CONHSO$_2$Ph(4-iPr) |
| H | 6-PhCONH | Bu | H | 2-OMe, 3-OMe | COOH |
| Me | 8-Me | Pr | H | 2-OMe, 3-OMe | COOH |
| Me | 8-Me | Pr | H | 2-OMe, 3-OMe | CONHSO$_2$Ph(4-!Pr) |
| Me | 8-Me | Pr | Pr | 2-OMe, 3-OMe | COOH |
| H | 8-Me | ci | ci | 2-OMe, 3-OMe | COOH |
| Me | 8-Me | Br | Br | 2-OMe, 3-OMe | COOH |
| H | 8-Me | H | Pr | 3,4-methylenedioxy | COOH |
| H | 8-Me | Pr | Pr | 3,4-methylenedioxy | COOH |
| H | 8-Me | H | Pr | 3,4-methylenedioxy | CONHSO$_2$Ph |
| H | 8-Me | Pr | Pr | 3,4-methylenedioxy | CONHSO$_2$Me |
| i-Pr | 8-Me | Pr | Pr | 3,4-methylenedioxy | COOH |
| i-Pr | 8-Br | Pr | Pr | 3,4-methylenedioxy | COOH |
| Ph | 8-Me | Pr | Pr | 3,4-methylenedioxy | COOH |
| (2-Et)Pr | 8-Me | Pr | Pr | 3,4-methylenedioxy | COOH |
| H | 8-Me | H | Pr | 3,4-methylenedioxy | CONHSO$_2$Ph(4-iPr) |
| i-Pr | 8-Br | H | Pr | 3,4-methylenedioxy | CONHSO$_2$Ph(4-iPr) |
| H | 6-PhCONH | Bu | H | 3,4-methylenedioxy | COOH |
| Me | 8-Me | Pr | H | 3,4-methylenedioxy | COOH |
| Me | 8-Me | Pr | H | 3,4-methylenedioxy | CONHSO$_2$Ph(4-iPr) |
| Me | 8-Me | Pr | Pr | 3,4-methylenedioxy | COOH |
| H | 8-Me | Cl | Cl | 3,4-methylenedioxy | COOH |
| Me | 8-Me | Br | Br | 3,4-methylenedioxy | COOH |
| H | 8-Me | H | Pr | 5-Br; 3,4-methylenedioxy | COOH |
| H | 8-Me | Pr | Pr | 5-Br; 3,4-methylenedioxy | COOH |
| H | 8-Me | H | Pr | 5-Br; 3,4-methylenedioxy | CONHSO$_2$Ph(4-iPr) |

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, furyl, pyrrolyl, thienyl, isothiazolyl, imidazolyl, pyrazinyl, pyrimidyl, pyrazolyl, purinyl, carbazolyl, isoxazolyl, thiazolyl, and oxazolyl.

The reaction schemes described below are reasonably general, it will be understood by those skilled in the art of organic synthesis that one or more functional groups present in a given compound of Formula I may render the molecule incompatible with a particular synthetic sequence. In such a case an alternative synthetic route, an altered order of steps, or a strategy of protection and deprotection may be employed. In all cases the particular reaction conditions, including reagents, solvent, temperature and time, should be chosen so that they are consistent with the nature of the functionality present in the molecule.

The compounds of Formula I, and more specifically compounds where R$^7$ is hydrogen, can be synthesized using the reactions and techniques described for the synthesis of the non-heterocyclic components in the patent application WO91/12001 (Merck & Co.; published on Aug. 22, 1991 under the Patent Cooperation Treaty) and also U.S. Pat. No. 5,177,095 (Merck & Co.; Jan. 5, 1993).

The reaction schemes described below have been generalized for simplicity. It is further to be understood that in the generalized schemes below, unless specified more narrowly in the text, the alkyl and aryl groups represent unfunctionalized or functionalized derivatives as described before. The leaving group Q present in the alkylating agents is either chloro, bromo, iodo, methanesufonate, p-toluenesulfonate or triflate.

ing ester either by refluxing the acid in an appropriate alcohol in the presence of a catalytic amount of conc. sulfuric acid, or using other conventional methods of esterification. The resulting ester is then refluxed in carbon tetrachloride with N-Bromosuccinimide and a catalytic amount of a radical initiator (e.g., AIBN or

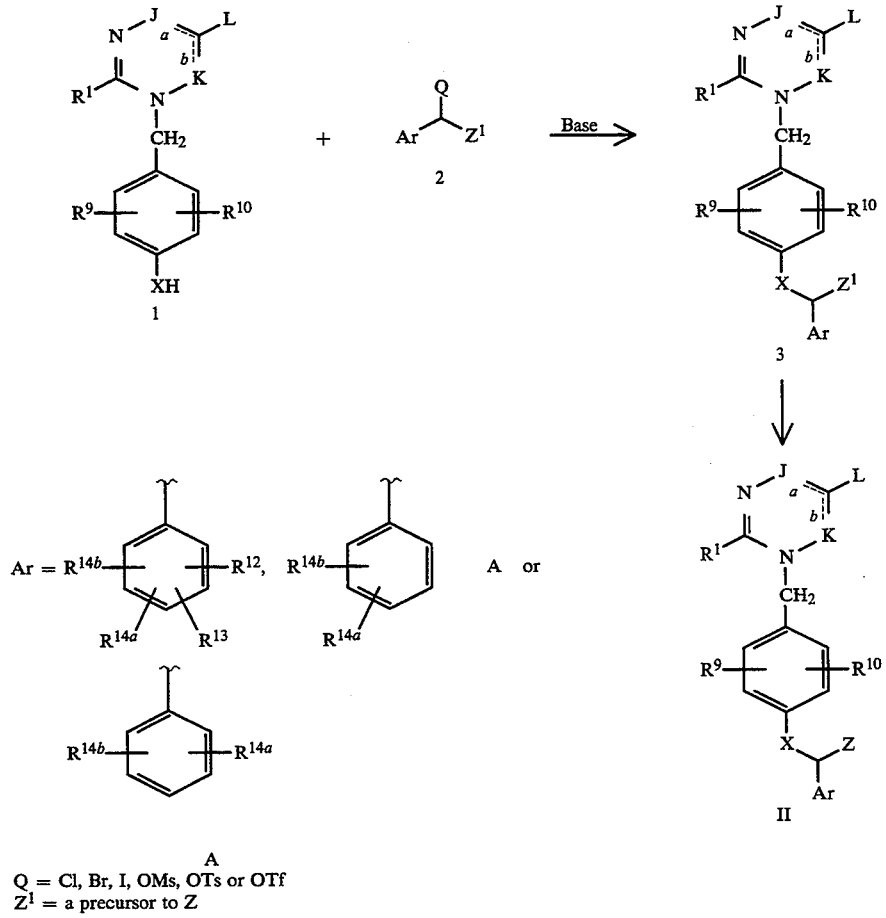

More specifically, the compounds of Formulae II (where X is oxygen, sulphur or appropriately substituted nitrogen and $R^7$ is H) can be synthesized as outlined in Scheme 1. The substituted compound 1 may be reacted with the alkylating agent 2 in an appropriate solvent such as alcohols (methanol, ethanol, isopropanol and like), dimethylformamide (DMF), dimethylsulfoxide (DMSO), tetrahydrofuran (THF) and acetone in the presence of an alkali metal salt such as alkoxides, carbonates, hydroxides and hydrides, or an organic base such as trialkylamines and alkyl lithiums to provide compound 3. The $Z^1$ group present in compound 3 may then be further transformed to provide desired compounds of Formula II.

In general, the alkylating agent 2 can be prepared using methods and techniques outlined in U.S. Pat. No. 5,177,095. More specifically, compound 2 (where $Z^1$ is COOR and Q is Br) can be synthesized from the substituted arylacetic acids 4 as outlined in Scheme 2. Substituted arylacetic acid 4 is converted to the correspondbenzoylperoxide) to provide the 2-bromoarylacetic acid ester 5.

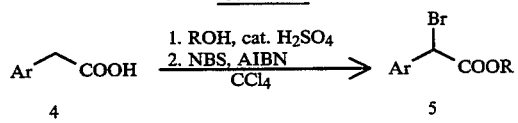

Alternatively, the ester 5 may also be prepared from appropriate aryl aldehydes (Scheme 3). The aldehyde 15 can be reacted with trimethylsilyl cyanide and catalytic amounts of KCN and 18-crown-6 to provide the corresponding trimethylsilyl cyanohydrin 7, which upon further treatment with the gaseous HCl and alcohol can afford the 2-hydroxy ester 8. The ester 8 is treated with triphenylphosphine and carbon tetrabromide in methylene chloride to give the 2-bromoarylacetate derivatives 5.

Scheme 3

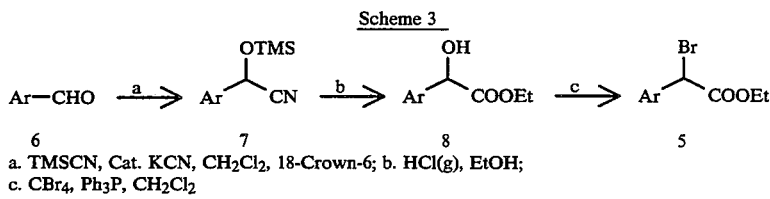

a. TMSCN, Cat. KCN, CH$_2$Cl$_2$, 18-Crown-6; b. HCl(g), EtOH;
c. CBr$_4$, Ph$_3$P, CH$_2$Cl$_2$ Scheme 4 illustrates a typical synthesis of an alkylating agent 12 (where Ar represents substituted indoles). The appropriately substituted cyanoindole 9 (for a general synthesis of substituted indoles refer to, R. K. Brown, *Indoles, Part One*, Ed. W. J. Houlihan, Vol. 25, Chapter II, Wiley-Interscience, New York, 1972) is reduced with DIBALH to provide the corresponding aldehyde, which is then converted into the N-Boc derivative 10. Reaction of 10 with the trichloromethide anion [genererated from KOH and CHCl$_3$; J. M. Wyvratt et. al., *J. Org. Chem.*, 52, 944–945 (1987)] followed by treatment with aqueous NaOH in DMF provides the alcohol 11. Treatment of 11 with diazomethane followed by the reaction with CBr$_4$/Ph$_3$P yields the alkylating agent 12.

A typical synthesis of alkylating agents bearing a substituted benzoxazole or benzthiazole ring is outlined in Scheme 5. The substituted benzoxazole 14 is prepared from the corresponding o-aminophenol 13 by the reaction of an appropriate orthoester under refluxing conditions (for other methods of synthesis of benzoxazoles see, S. A. Lang and Y. Lin, *Comprehensive Heterocyclic Chemistry*, Vol. 6, 1–130, Ed. C. W. Rees; and references cited therein). Reduction of 14 with NaBH$_4$ provides the alcohol 15 which is then subjected to pyridiniumdichromate oxidation (PDC) to yield the corresponding aldehyde 16. Further elaboration of 16 as outlined provides the key intermediate 17. Similarly, the benzothiazole 19 can also be prepared form the appropriately substituted o-aminothiophenol 18.

Scheme 4

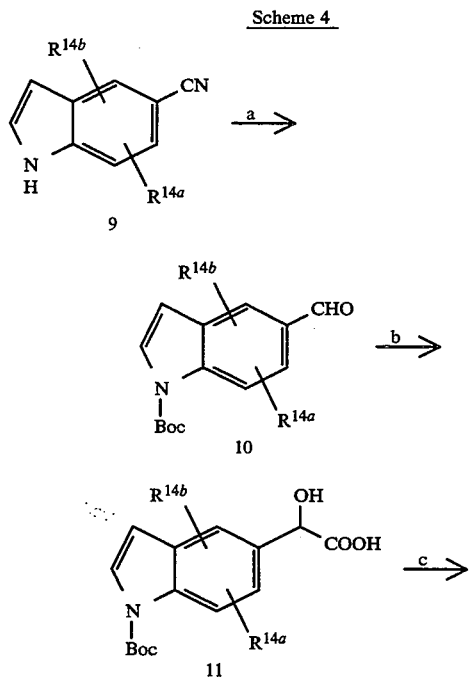

-continued
Scheme 4

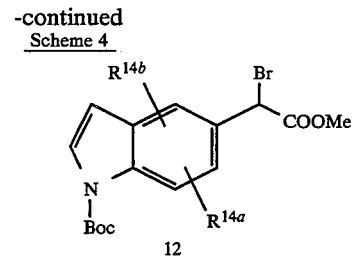

a. (i) DIBALH, Toluene; (ii) Boc$_2$O, DMAP, CH$_2$Cl$_2$
b. (i) CHCl$_3$, KOH, DMF, 0° C.; (ii) NaOH, DME/H$_2$O
c. (i) CH$_2$N$_2$; (ii) CBr$_4$/Ph$_3$P, CH$_2$Cl$_2$ Scheme 5

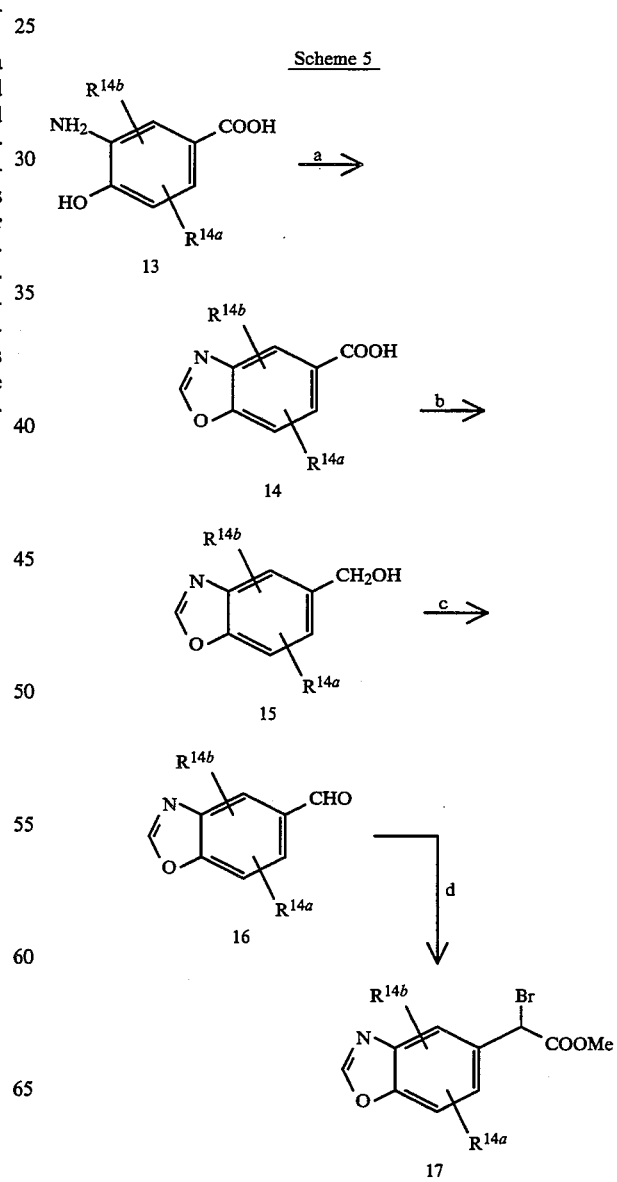

-continued
Scheme 5 a. CH(OEt)$_3$, EtOH, reflux
b. (i) ClCOOEt, Et$_3$N, THF; (ii) NaBH$_4$, THF-H$_2$O
c. Pyridiniumdichromate, CH$_2$Cl$_2$
d. (i) CHCl$_3$, KOH, DMF, 0° C.; (ii) NaOH, DME/H$_2$O; (iii) HCl/MeOH; (iv) CBr$_4$/Ph$_3$P, CH$_2$Cl$_2$

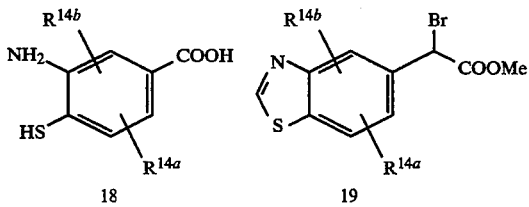

Scheme 6 illustrates the synthesis of benzofuran and dihydrobenzofuran alkylating agents 23 and 25. The benzofuran 21 can be prepared from the α-phenoxy carbonyl compound 20 via a ring closure reaction [Stoermer and Wehln, Chem. Ber., 35, 3549 (1902)] (for general methods of synthesis of benzofurans and dihydrobenzofurans see, R. C. Elderfield and V. B. Meyer, Heterocyclic Compounds, Vol. 2, Chapter 1, Ed. R. C. Elderfield, Wiley; and references cited therein). The ester 21 is reduced to provide the aldehyde 22 which is then transformed into the corresponding alkylating agent 23. The dihydrobenzofuran ester 24, obtained by catalytic reduction of 21, can also be transformed into the corresponding alkylating agent 25 using the sequence of reactions outlined in Scheme 6.

Benzothiophene 26 may be synthesized from the corresponding aldehyde 26b in a manner similar to that outlined in Scheme 6 for benzofuran 23. Benzothiophene 26b can be prepared by the oxidative cyclization (using an alkaline solution of potassium ferricyanide) of appropriately substituted o-mercaptocinnamic acid 26a [C. Chmelewsky and P. Friedlander, Chem. Ber., 46, 1903 (1913)]. (For general methods of synthesis of benzothiophene, See, E. Champaigne in Comprehensive Heterocyclic Chemistry, vol. 4, Chapter 3-15; Eds. A. Katritzky and C. W. Rees.)

Scheme 7 outlines a typical synthesis of α-bromoarylacetates, 30 and 32, bearing appropriately substituted methylenedioxy or 1,4-dioxane rings. The substituted catechol derivative 27 is treated with an appropriate dibromide (where m is 1 or 2) in the presence of cesium carbonate in dimethylformamide to provide 28. Treatment of 28 with DIBALH yields the aldehyde 29 which is then transformed into the desired alkyl bromide as described.

Scheme 6

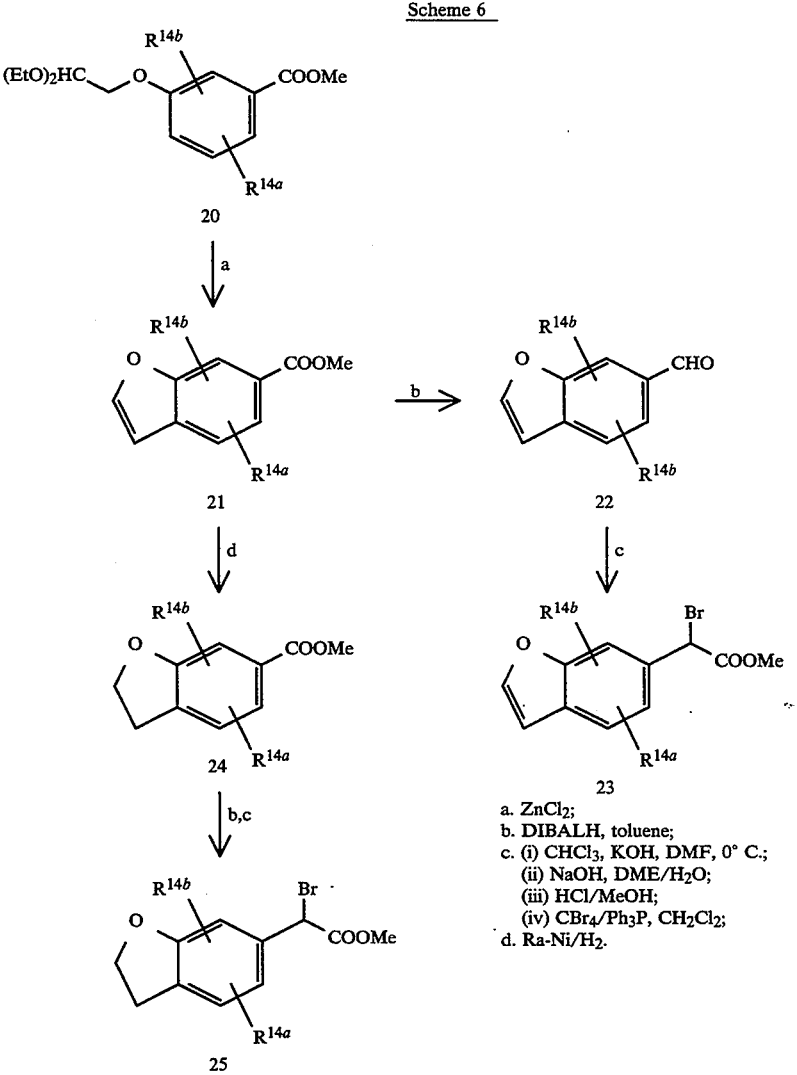

a. ZnCl$_2$;
b. DIBALH, toluene;
c. (i) CHCl$_3$, KOH, DMF, 0° C.;
   (ii) NaOH, DME/H$_2$O;
   (iii) HCl/MeOH;
   (iv) CBr$_4$/Ph$_3$P, CH$_2$Cl$_2$;
d. Ra-Ni/H$_2$.

-continued
Scheme 6

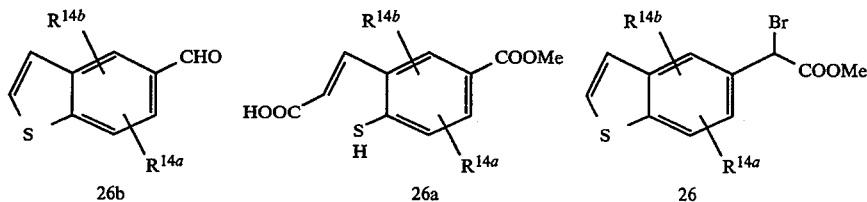

Scheme 7

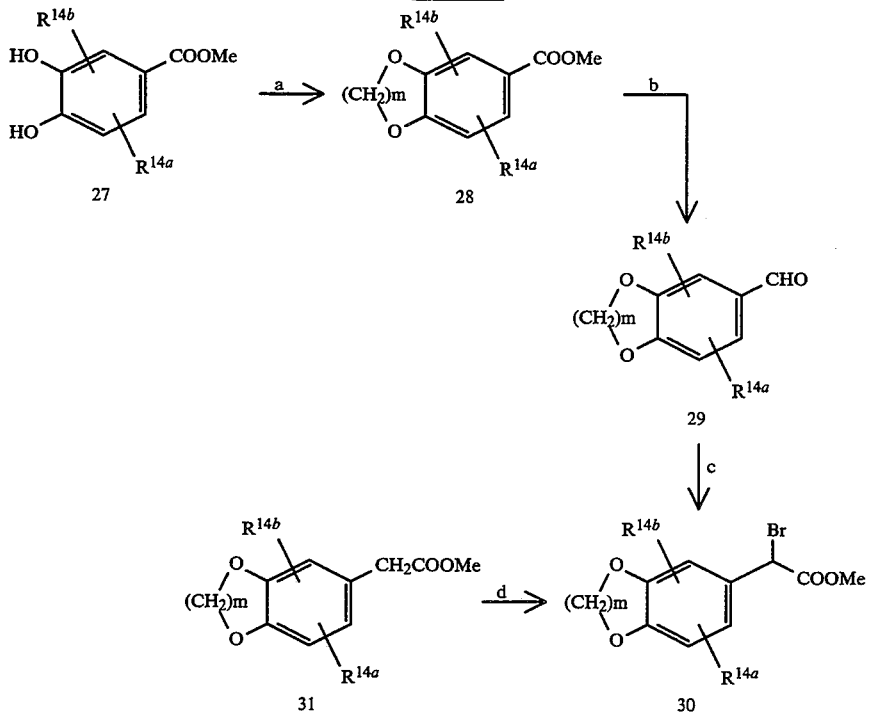

a. Br—(CH2)$_m$—Br, Cs2CO3, DMF
b. DIBALH, toluene
c. (i) CHCl3, KOH, DMF, 0° C.; (ii) NaOH, DME/H2O;
   (iii) HCl/MeOH; (iv) CBr4/Ph3P, CH2Cl2;
d. NBS, AIBN, CCl4

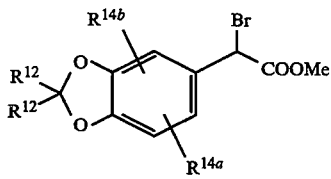

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, H2SO4, H3PO4, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol 10, R. V. Heinzelman, Ed., Academic Press, New York London, 1975, Ch. 31, pp. 306–326), H. Ferres, *Drugs of Today*, Vol 19, 499–538 (1983) and *J. Med. Chem.*, 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

It will be further appreciated that the majority of compounds of general Formula I claimed herein are asymmetric and are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formula I and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formula I, their pharmaceutically acceptable salts and their prodrug forms are also included within the scope of this invention.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in gastrointestinal, kidney, lung, urogenital, uteral and placental tissues.

Endothelin is a potent vasoconstrictor peptide and thus plays an in vivo role in arterial pressure-volume homeostasis. Not only peripheral, but coronary vascular resistance as well, is increased by endothelin. Cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results from myointimal thickening following angioplasty, which is caused by increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compounds of the present invention, which are receptor antagonists of endothelin, have therapeutic usefulness in preventing, decreasing or modulating the various physiological effects of endothelin discussed above, by wholly or partially blocking access of endothelin to its receptor.

Endothelin Receptor Binding Assays

The binding of the novel compound of this invention to the endothelin receptor was determined in accordance with the assay described in detail immediately below. It is similar to the assay described in Ambar et al. (1989) *Biochem. Biophys. Res. Commun.* 158, 195–201; and Kloog et al. (1989) *FEBS Letters*, 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor binding assay using cow aorta membrane preparation:

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 μg/mL leupeptin and 7 μg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The membrane pellet thus obtained was resuspended in the buffer solution described above (including the protease inhibitors), and aliquots were quick-frozen and stored at −70° C. until use. Membranes were diluted into 50 mM KPi, 5 mM EDTA pH 7.5 containing 0.01% human serum albumin. Assays were done in triplicate. Test compounds and 100 pM [$^{125}$I]-endothelin-1 (2000–2200 Ci/μmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration ($IC_{50}$) which gives 50% displacement of the total specifically bound [$^{125}I$]-endothelin-1 was presented as a measure of the potency of such compound as ET antagonist.

Receptor binding assay using rat hippocampal membrane preparation:

Rat hippocampi were obtained from freshly sacrificed male Sprague-Dawley rats and placed in ice cold 0.25M sucrose, 5 mM tris-HCl, pH 7.4 containing 0.5 µg/mL leupeptin, 7 µg/mL pepstatin A. Hippocampi were weighed and placed in a Dounce homogenizer with 25 volumes (wet weight to volume) ice-cold sucrose buffer in the presence of protease inhibitors. Hippocampi were homogenized using the Dounce (glass-glass) homogenizer with type A pestle, with the homogenizer immersed in ice. Tissue homogenate was centrifuged at 750×g for 10 min at 4° C. Supernatant was filtered through dampened cheesecloth, and centrifuged again at 48,000×g for 30 min at 4° C. Membrane pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}I$]-endothelin-1 (2000–2200 Ci/µmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}I$ radioactivity in a gamma counter. Nondisplaceable binding of [$^{125}I$]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration ($IC_{50}$) which gives 50% displacement of the total specifically bound [$^{125}I$]-endothelin- 1 was presented as a measure of the potency of such compounds as endothelin antagonists.

Receptor binding assay using cloned human ET receptors expressed in Chinese Hamster Ovary Cells:

Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM $NaH_2PO_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}I$]-endothelin-1 (2000–2200 Ci/µmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pad and washed with 150 mM NaCl, 0.1% BSA.

The filters were assayed for $^{125}I$ radioactivity in a gamma counter. Nondisplaceable binding of [$^{125}I$]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration ($IC_{50}$) which gives 50% displacement of the total specifically bound [$^{125}I$]-endothelin-1 was presented as a measure of the potency of such compounds as endothelin antagonists.

The binding assays described above were used to evaluate the potency of interaction of the compounds of the invention with endothelin receptors. To determine whether these compounds were endothelin antagonists, assays which measure the ability of the compounds to inhibit endothelin-stimulated phosphatidylinositol hydrolysis were established. Rat uterus contains predominantly one of the known endothelin receptor subtypes ($ET_A$).

Phosphatidylinositol hydrolysis assays using rat uterine slices:

Diethylstilbestrol primed female Sprague-Dawley rats were sacrificed and their uteri were collected, dissected of fat and connective tissue and minced. Minced tissue was added to oxygenated (95% $O_2$, 5% $CO_2$) 127 mM NaCl, 25 mM $NaHCO_3$, 10 mM Glucose, 2.5 mM KCl, 1.2 mM $KH_2PO_4$, 1.2 mM $MgSO_4$, 1.8 mM $CaCl_2$. To the tissue mince, 1.2 µM myo-[$^3H$]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to a final concentration of 3 nM to start the assay. Assays were done in quadruplicate. Samples were incubated at 37° C. under blowing $O_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 µL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Sarafotoxin S6c is a member of the endothelin family which binds preferentially to one of the known endothelin receptor subtypes ($ET_B$).

Phosphatidylinositol hydrolysis assays using rat lung slices:

Male Sprague-Dawley rats were sacrificed and their lungs were collected, dissected of fat and connective tissue and minced. Minced tissue was added to oxygenated (95% $O_2$, 5% $CO_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 $\mu$M myo-[$^3$H]-inositol was added. The mince was incubated 60 min at 37° C., with constant oxygenation. After incubation, loaded tissue mince was washed five tinges with the same oxygenated buffer to remove excess radiolabelled inositol. Tissue mince was resuspended in the above buffer, containing 10 mM LiCl, aliquotted into tubes, and sarafotoxin S6c (to a final concentration of 3 nM) with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 $\mu$L aliquot of this solution was assayed for radioactivity in a beta counter. The diluted neutralized sample was applied to Dowex 1×8-formate colunms, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration (IC$_{50}$) is the concentration of test compound required to give a sample activity of 50% of control value.

Phosphatidylinositol hydrolysis assays using cloned human endothelin receptors expressed in Chinese Hamster Ovary cells:

Endothelin receptors of both receptor subtypes were cloned from a human cDNA library and were individually expressed in Chinese Hamster Ovary cells. Cells were loaded overnight by the addition of 1.2 $\mu$M myo-[$^3$H]-inositol to their growth medium. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were washed five times by centrifugation at 250×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and endothelin-1 (to a final concentration of 0.3 nM) with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 $\mu$L aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolunm sample. Control values (100% stimulated) are values in the presence of endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Using the methodology described above, the compounds of the invention were evaluated and found to exhibit IC50 values of at least <50 $\mu$M thereby demonstrating and confirming the utility of the compounds of this invention as an effective endothelin antagonists.

Accordingly the novel compounds of the present invention are useful in human therapy for treating asthma, hypertension, pulmonary hypertension, arterioscelerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 0.5 mg.–1.0 g. per patient per day which can be administered in single or multiple doses. Preferably, the dosage range will be about 0.5–500 mg. per patient per day; more preferably about 0.5–100 rag. per patient per day.

The present invention also relates to pharmaceutical compositions for treating asthma, hypertension, pulmonary hypertension, arterioscelerosis, heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, comprising a therapeutically effective amount of the novel compound of this invention together with a pharmaceutically acceptable carrier thereof.

About 0.5 mg.–1.0 g. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage uniform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formula I and their incorporation into pharmaceutical compositions and as such are not to be considered as limiting the invention set forth in the claims appended hereto.

EXAMPLE 1

2-Butyl-3-[4-((1-carboxy-1-phenyl)methoxy)-3-allyl]-phenyl]methyl-6-methylquinazolin-4(3H)-one Step A: Preparation of 4-(2-propen-1-yloxy)benzyl alcohol To a suspension of NaH (130 mg; 4.33 mmol) in DMF (5 mL) at 0° C. under nitrogen was added a solution of 4-hydroxmethylphenol (512 mg; 4.12 mmol) in DMF (5 mL). After stirring 5 minutes at room temperature, a solution of allyl bromide (375 mL, 4.33 mmol) in DMF (5 mL) was added dropwise. The reaction was stirred for 20 minutes at 0° C., then quenched with water and concentrated in vacuo. The residue was partitioned between water and ethyl acetate. The combined organic layers were washed with 4% HCl, saturated NaHCO3, and then brine, and dried (MgSO4), filtered and concentrated in vacuo to yield 650 mg (97%) of the title compound.

$^1$H NMR (300 MHz, CDCl$_3$, ppm): δ 7.27 (dd, 2H), 6.90 (apparent d, 2H), 6.12-5.98 (m, 1H), 5.41 (apparent dd, 1H), 5.29 (dd, 1H), 4.58 (s, 2H), 4.52 (dd, 2H), 1.93 (br s, 1H).

Step B: Preparation of 4-tert-butyldimethylsilyloxymethylphenyl-(2-propen-1-yl)ether To a solution of the product of Step A (650 mg, 3.96 mmol) in CH$_2$Cl$_2$ (20 mL), cooled to 0° C. under nitrogen, was added triethylamine (612 mL, 4.39 mmol) and a solution of tert-butyldimethylsilyl chloride (631 mg; 4.19 mmol) in CH$_2$Cl$_2$ (2 mL). After stirring at room temperature for 18 hours, the reaction mixture was diluted with ethyl acetate (60 mL), washed with water, and saturated sodium bicarbonate, and then dried (MgSO$_4$). The filtrate was concentrated in vacuo to afford 1.1 g of the title compound which was used crude in the next reaction (R$_f$=0.45, 5% ethyl acetate/hexanes).

$^1$H NMR (300 MHz, CDCl$_3$, ppm): δ 7.24 (d, 2H), 6.89 (d, 2H), 6.15-6.00 (m, 1H), 5.42 (apparent d, 1H), 5.30 (apparent d, 1H), 4.68 (s, 2H), 4.53 (apparent dd, 2H), 0.95 (s, 9H), 0.12 (s, 6H).

Step C: Preparation of 4-tert-butyldimethylsilyloxymethyl-2-allylphenol

The product of Step B (0.51 g, 1.83 mmol) was heated to 200° C. under a nitrogen atmosphere for 5 hours. The crude reaction mixture was dissolved in eluant and chromatographed on silica (MPLC, 5/95 ethyl acetate/hexane) to afford 178 mg (35%) of the title compound (R$_f$=0.11, 5% ethyl acetate/hexanes).

$^1$H NMR (300 MHz, CDCl$_3$, ppm): δ 7.10 (unsymmetrical d, 2H), 6.78 (d, 2H), 6.09-5.94 (m, 2H), 5.21-5.11 (m, 2H), 5.00 (s, 1H), 4.67 (s, 2H), 3.40 (d, 2H), 0.95 (s, 9H), 0.11 (s, 6H).

FAB MS: m/e=277 (M+1).

Step D: Preparation of methyl 2-(4-tert-butyl-dimethylsilyloxymethyl-2-allylphenoxy)-2-phenylacetate To a suspension of KH (1.3 eq) in DMF (1 mL) was added a solution of the product of Step C (157 mg, 0.566 mmol) in DMF (1 mL), followed by 18-crown-6 (30 mg; 0.2 eq). The reaction mixture was stirred for 5 minutes at room temperature. A solution of methyl 2-bromophenylacetate (168 mg, 0.735 mmol) in DMF (1 mL) was added, followed by a catalytic amount of potassium iodide. The reaction was heated to 80° C. for 0.5 hours then stirred at room temperature for 16 hours. After concentration in vacuo, the residue was partitioned between water and ethyl acetate. The combined organic layers were washed with water, brine, then dried (MgSO$_4$). After filtration and concentration in vacuo, the residue was chromatographed on silica (MPLC, ethyl acetate/hexanes (5/95)) to afford 158 mg (66%) of the title compound (R$_f$=0.22, 5% ethyl acetate/hexanes).

$^1$H NMR (300 MHz, CDCl$_3$, ppm): δ 7.64-7.57 (dd, 2H), 7.46-7.35 (m, 3H), 7.17-7.06 (m, 2H), 6.72 (d, 1H), 6.12-5.98 (m, 1H), 5.65 (s, 1H), 5.11-5.04 (m, 2H), 4.66 (s, 2H), 3.72 (s, 3H), 3.53 (d, 2H), 0.95 (s, 9H), 0.10 (s, 6H).

FAB MS: consistent with structure.

Step E: Preparation of methyl 2-(4-bromomethyl-2-allylphenoxy)-2-phenylacetate

To a cooled (0° C.) solution of the product of Step D (156 mg, 0.366 mmol) in CH$_3$CN (2 mL), were added carbon tetrabromide (182 mg, 0.55 mmol) and triphenylphosphine (144 mg, 0.55 mmol). After 30 minutes at 0° C., the reaction mixture was allowed to warm to room temperature, at which point acetone (40 mL, 0.55 mmol) was added. After 16 hours at room temperature, the reaction mixture was filtered, the filtrate was concentrated in vacuo, and the residue was purified on a silica gel flash chromatography column eluted with 5% ethyl acetate/hexanes to afford 86 mg (63%) of the title compound (R$_f$=0.13, 5% ethyl acetate/hexanes).

$^1$H NMR (300 MHz, CDCl$_3$, ppm): δ 7.67-7.57 (dd, 2H), 7.47-7.37 (m, 3H), 7.27-7.13 (m, 2H), 6.72 (d, 1H), 6.16-5.98 (m, 1H), 5.68 (s, 1H), 5.20-5.08 (m, 2H), 4.49 (s, 2H), 3.73 (s, 3H), 3.54 (d, 2H).

FAB MS: consistent with structure.

Step F: Preparation of 2-n-butyl-6-methylquinazolin-4(1H)-one

To a solution of 3.0 g (20 mmol) of 2-amino-5-methyl benzoic acid in 20 mL of dry DMF at 0° C. was added 200 mg of DMAP followed by 6.07 g (60 mmol) of triethylamine and 5.02 g (40 mmol) of valeryl chloride. The resulting mixture was stirred at 0° C. for 30 min. The mixture was heated to 110° C. and monitored by TLC for the formation of the intermediate quinoxazolone ($R_f=0.8$, 40% EtOAc/hexane). Following complete formation of the intermediate 10 g (100 mmol) of $(NH_4)_2CO_3$ was added cautiously. Heating was continued to ensure consumption of the quinoxazolone and formation of the polar ($R_f=0.4$, 40% EtOAc/hexane) quinazolin-4(1H)-one. The reaction mixture was concentrated in vacuo and the residue was taken up in 50 mL of ether and 50 mL of water. The mixture was filtered and the filtrate discarded after washing the residue with 20 mL of ether. The residue was recrystalized from MeOH to give 1.07 g (25%) of the title compound as a white crystalline solid.

$^1$H NMR (300 MHz, CDCl$_3$, ppm): δ 0.94 (t, 3H, J=6.7 Hz), 1.50 (m, 2H), 1.83 (m, 2H), 2.49 (s, 3H), 2.78 (t, 2H), 7.60 (m, 2H), 8.05 (m, 1H).

Anal ($C_{13}H_{16}N_2O$), C, H, N.

Step G: Preparation of 2-Butyl-3-[4-((1-carbomethoxy-1-phenyl)-methoxy)-3-allylphenyl]methyl-6-methylquinazolin-4(3H)-one To a suspension of NaH (0.514 mmol) in DMF (2 mL) was added 92 mg (0.428 mmol) of 2-butyl-6-methylquinazolin-4(3H)-one (Step F of Example 1) and the reaction mixture was stirred for 30 minutes at room temperature. A solution of the product of Step E (177 mg, 0.471 mmol) in DMF (1.5 mL) was added, and the reaction was stirred at room temperature for 18 hours. The reaction mixture was then concentrated in vacuo and partitioned between water and ethyl acetate. The combined organic layers were washed with water then brine, dried (MgSO$_4$), filtered, and concentrated in vacuo. The residue was chromatographed on silica (MPLC, hexanes/ethyl acetate (4/1)) to afford 96 mg (44%) of the title compound.

$^1$H NMR (300 MHz, CDCl$_3$, ppm): δ 8.08 (s, 1H), 7.6-7.49 (br s, 4H), 7.42-7.28 (m, 3H), 7.09-7.01 (br s, 1H), 6.93-6.83 (br dd, 1H), 6.66 (d, 1H), 6.08-5.92 (m, 1H), 5.60 (s, 1H), 5.36-5.22 (br s, 2H), 5.12-4.98 (m, 2H), 3.68 (s, 3H), 3.48 (d, 2H), 3.48 (d, 2H), 2.72 (t, 2H), 2.48 (s, 3H), 1.80-1.65 (m, 2H), 1.40 (q, 2H), 0.90 (t, 3H).

FAB MS: m/e=511 (M+1).

Step H: Preparation of 2-Butyl-3-[4-((1-carboxy-1-phenyl)-methoxy)-3-allylphenyl]methyl-6-methylquinazolin-4(3H)-one To a solution of the product of Step G (20 mg, 0.039 mmol) in MeOH (2 mL), were added 4 drops of water and 2.0N NaOH (22 mL, 0.043 mmol). After stirring for 18 hours at room temperature, the reaction mixture was concentrated in vacuo, dissolved in water/THF, and treated with HCl (0.15 mL, 1.0N) at room temperature for 30 minutes. The reaction mixture was then concentrated in vacuo and chromatographed on a Sephadex LH-20 column eluted with MeOH to afford 19 mg of crude product, which was recrystallized from MeOH to yield 2 mg (10%) of the title compound.

$^1$H NMR (300 MHz, CD$_3$OD, ppm): δ 8.05 (s, 1H), 7.70 (d, 1H), 7.63-7.48 (m, 3H), 7.44-7.28 (m, 3H), 7.08 (s, 1H), 6.99-6.92 (m, 1H), 6.83 (d, 1H), 6.07-5.92 (m, 3H), 5.73 (s, 1H), 5.40 (s, 2H), 5.08-5.88 (m, 2H), 3.46 (br s, 2H), 2.80 (t, 2H), 2.51 (s, 3H), 1.68-1.57 (m, 2H), 1.43-1.28 (m, 2H), 0.88 (t, 3H).

FAB MS: m/e=497 (M+1).

EXAMPLE 2

2-Butyl-3-[4-((1-carboxy-1-phenyl)methoxy)-3-propylphenyl]methyl-6-methylquinazolin-4(3H)-one Step A: Preparation of 2-Butyl-3-[4-((1-carbomethoxy-1-phenyl)-methoxy)-3-propylphenyl]methyl-6-methylquinazolin-4(3H)-one To a solution of the product of Example 1, Step G (20 mg, 0.039 mmol) in CH$_2$Cl$_2$ (2 mL), was added Wilkinson's catalyst (7.6 mg). The reaction mixture was hydrogenated at 40 psi, room temperature for 4.5 hours. After concentration in vacuo, the residue was chromatographed on silica (MPLC, hexanes/ethyl acetate (4/1) to afford 15 mg (78%) of the title compound.

$^1$H NMR (300 MHz, CDCl$_3$, ppm): δ 8.10 (s, 1H), 7.63-7.54 (m, 4H), 7.46-7.36 (m, 3H), 7.02 (apparent s, 1H), 6.89 (dd, 1H), 6.63 (d, 1H), 5.62 (s, 1H), 5.32 (br s, 2H), 3.71 (s, 3H), 2.79-2.63 (m, 4H), 2.50 (s, 3H), 1.80-1.60 (m, 2H), 1.48-1.34 (m, 2H), 1.02-0.87 (m, 6H).

FAB-MS: m/e=513 (M+1).

Step B: Preparation of 2-Butyl-3-[4-((1-carboxy-1-phenyl)-methoxy)-3-propylphenyl]methyl-6-methylquinazolin-4(3H)-one To a solution the product of Step A (11 mg; 0.22 mmol) in MeOH (2 mL) was added NaOH (1.5 eq, 2.0N) and a few drops of water. After stirring for 20 hours at room temperature, the reaction mixture was concentrated in vacuo, dissolved in water/THF, treated with HCl (5 eq) for 30 minutes at room temperature, concentrated in vacuo, and chromatographed on a Sephadex LH-20 column eluting with MeOH to afford 11 mg (99%) of the title compound.

$^1$H NMR (300 MHz, CD$_3$OD, ppm): δ 8.19 (s, 1H), 7.88 (d, 1H), 7,68 (d, 1H), 7.58 (dd, 2H), 7.48-7.33 (m, 3H), 7.18 (s, 1H), 7.08 (d, 1H), 6.84 (d, 1H), 5.70 (s, 1H), 5.48 (s, 2H), 3.15-3.03 (m, 2H), 2.69 (t, 2H), 2.53 (s, 3H), 1.72-1.5 (m, 4H), 1.49-1.34 (m, 2H), 0.98-0.84 (m, 6H).

FAB-MS: m/e=499 (M+1).

EXAMPLE 3

2-Butyl-3-[4-((1-carboxy-1-phenyl)methoxy)-3-chloro-phenyl]methyl-6-methylquinazolin-4(3H)-one Step A: Preparation of methyl 2-(2-chloro-4-methylphenoxy)-2-phenylacetate To a suspension of 0.282 g (7.04 mmol) of a 60% oil dispersion of sodium hydride in DMF was added 1.00 g (7.04 mmol) of 2-chloro-4-methylphenol and the mixture was stirred under an N$_2$ atmosphere at room temperature. After 10 minutes, a solution of 1.94 g (8.45 mmol) of methyl 2-bromophenylacetate dissolved in 10 mL of DMF was added and the reaction was stirred an additional 1.5 hours. The reaction was then diluted into ethyl acetate, washed with water, dried (MgSO$_4$), filtered and evaporated. The residue was purified on a silica gel flash chromatography column eluted with 4% ethyl acetate/hexane to afford 1.70 g (83%) of the title compound.

$^1$H NMR (300 MHz, CDCl$_3$, ppm): δ 2.20 (s, 3H), 3.70 (s, 3H), 5.60 (s, 1H), 6.70–6.80 (d, 1H), 6.85–6.95 (d, 1H), 7.20 (br s, 1H), 7.20–7.30 (m, 3H), 7.55–7.65 (m, 2H).

EI-MS: m/e 290 (M+).

Step B: Preparation of methyl 2-(2-chloro-4-bromomethylphenoxy)-2-phenylacetate

To a solution of 1.70 g (5.86 mmol) of the product from Step A dissolved in 20 mL of CCl$_4$ was added 1.04 g (5.86 mmol) of N-bromosuccinimide and 50 mg (catalytic amount) of AIBN. The reaction mixture was stirred and heated at reflux for 7 hours, then an additional 0.20 g of NBS was added. The reaction was refluxed for 48 hours, then cooled and concentrated in vacuo. The residue was purified on a silica gel flash chromatography column eluted with 10% ethyl acetate/hexane to afford 0.730 g (34%) of the title compound.

$^1$H NMR (300 MHz, CDCl$_3$, ppm): δ 3.70 (s, 3H), 4.40 (s, 2H), 5.65 (s, 1H), 6.75–6.85 (d, 1H), 7.10–7.20 (d, 1H), 7.30–7.45 (m, 4H),7.55–7.65 (m, 2H).

FAB-MS: m/e 369 (M+1).

Step C: Preparation of 2-butyl-3-[4-((1-carbomethoxy- 1-phenylmethoxy)-3-chlorophenyl]methyl-6-methylquinazolin-4(3H)-one To a half suspension of 62 mg (0.287 mmol) of the product of Step F of Example 1 in 1.0 mL of anhydrous DMF was added 12 mg (1.05 eq) of a 60% oil dispersion of sodium hydride and the reaction mixture was stirred under an N$_2$ atmosphere. After stirring 10 minutes at room temperature, a solution of 0.127 g (1.2 eq) of the product of Step B dissolved in 1.0 mL DMF was added to the solution of the anion. The reaction mixture was then stirred overnight, then partitioned between water and ethyl acetate. The organic layer was separated, dried (MgSO$_4$), filtered and evaporated in vacuo. The residual oil was purified on a silica gel flash chromatography column eluted with 30% ethyl acetate/hexane to afford 76 mg (52%) of the title compound.

$^1$H NMR (300 MHz, CDCl$_3$, ppm): δ 0.87–0.94 (t, 3H), 1.32–1.45 (m, 2H), 1.67–1.78 (m, 2H), 2.42 (s, 3H) 2.66–2.72 (t, 2H), 3.70 (s, 3H), 5.30 (br s, 2H), 5.60 (s, 1H), 6.77 (d, 1H), 6.94 (dd, 1H), 7.18 (s, 1H), 7.33–7.42 (m, 3H), 7.53–7.61 (m, 4H), 8.06 (s, 1H).

FAB-MS: m/e 505, 507 (M+1, 3:1 ratio).

Step D: Preparation of 2-butyl-3-[4-((1-carboxy- 1-phenyl)methoxy)-3-chlorophenyl]methyl-6-methylquinazolin-4(3H)-one To a solution of 72 mg of the product of Step C dissolved in 2 mL of methanol, was added 0.25 mL of a 1N solution of NaOH and the reaction mixture was stirred at room temperature for 3 days. The reaction mixture was then adjusted to pH 7 with 1N HCl, concentrated in vacuo, and the residue was applied to a silica gel flash chromatography column and eluted with CHCl$_3$/MeOH/NH$_4$OH (80:15:1). Evaporation of the purified fractions and drying in vacuo afforded 50 mg (71%) of the title compound.

$^1$H NMR (300 MHz, CD$_3$OD, ppm): δ 0.92–0.98 (t, 3H), 1.37–1.48 (m, 2H), 1.66–1.77 (m, 2H), 2.54 (s, 3H), 2.78–2.84 (t, 2H), 5.40 (s, 2H), 5.68 (s, 1H), 7.01–7.10 (m, 2H), 7.31–7.44 (m, 4H), 7.58–7.72 (m, 4H), 8.07 (s, 1H).

FAB-MS: m/e 491, 493 (M+1, 3:1 ratio).

EXAMPLE 4

3-[4-((1-Carboxy-1-phenyl)methoxy)-3-chloro-5-methoxyphenyl]methyl-6-(N-methyl-N-iso-butyloxycarbonyl)amino-2-propylquinazolin-4(3H)-one Step A: Preparation of 2-propyl-6-nitroquinazolin-4(1H)-one To a suspension of 48.94 g (0.3 mol) of 3-nitro-5-aminobenzonitrile in 500 mL of CH$_2$Cl$_2$ was added 63 mL of Et$_3$N, 3 g DMAP and lastly, dropwise, 45.5 g (0.45 mol) of butyryl chloride. A mild exothermic reaction ensued. The mixture was allowed to stir for 2 days (monitored by TLC with 50% EtOAc/hexanes). The solution was washed with 1N HCl (2×100 mL), water (1×100 mL), saturated NaHCO$_3$ (2×100 mL), brine (1×100 mL) and dried over MgSO$_4$. The suspension was filtered and concentrated in vacuo. The residue was suspended in a mixture of 600 mL of MeOH and 200 mL of water in a three neck round bottom flask. To this was added gradually 140 mL of 5N NaOH (0.7 mol) solution followed by the dropwise addition of 80 mL of 30% H$_2$O$_2$ (0.7 mmol) solution (exothermic). The mixture was refluxed overnight, cooled to room temperature and filtered. The filtrate was acidified with 1N HCl cooled to 5° C. and filtered. The quinazolinone was recrystallized from hot MeOH to give 38 g (54%) of the title compound as pale brown fine crystals.

$^1$H NMR (300 MHz, CDCl$_3$, ppm): δ 1.10 (t, 3H, J=7.8 Hz), 1.93 (m, 2H), 2.79 (t, 2H, J=7.3 Hz), 7.81 (d, 1H, J=8.9 Hz), 8.55 (dd, 1H, J=2.4, 8.8 Hz), 9.14 (d, 1H, J=2.4 Hz), 10.72 (br s, 1H).

Step B: Preparation of 3-(4,4'-dimethoxybenzhydryl)-2-propyl-6-nitroquinazolin-4(3H)-one To a suspension of 1.01 g (33.7 mmol) of 80% sodium hydride in 20 mL of dry DMF was added at 0° C. 7.5 g (32 mmol) of the product of Step A as a solid. The reaction mixture was diluted with a further 50 mL of DMF to assist stirring. After hydrogen evolution was complete, a solution of 8.8 g (33.7 mmol) of 4,4'-dimethoxybenzhydryl chloride in 20 mL of dry DMF was added dropwise. The reaction mixture was stirred overnight and then poured into 300 mL of 0.1N NaOH. The precipitate was collected by filtration and dried under vacuum to give 12.1 g (94%) of a yellow solid.

$^1$H-NMR (300 MHz, CDCl$_3$, ppm): δ 0.87 (t, 3H, J=7.3 Hz), 1.58 (br m, 2H), 2.72 (t, 2H, J=7.8 Hz), 3.80 (s, 6H), 6.88 (d, 4H, J=9 Hz), 7.19 (d, 4H, J=9.0 Hz), 7.73 (d, I H, J=8.9 Hz), 8.48 (dd, 1H, J=2.8, 9.0 Hz), 9.08 (d, 1H, J=2.8 Hz).

Step C: Preparation 6-amino-3-(4,4'-dimethoxybenzhydryl)-2-propylquinazolin-4(3H)-one A solution of 12.1 g (26.0 mmol) of the product of Step B dissolved in 250 mL of EtOAc was hydrogenated under atmospheric pressure over three days in the presence of three portions of 1.2 g of 10% Pd/C added daily. The mixture was filtered through celite and concentrated in vacuo to give an oil. The product was purified by flash chromatography over silica gel eluted with 50% EtOAc/hexanes to give 7.8 g (72%) of the amine.

$^1$H-NMR (300 MHz, CDCl$_3$, ppm): δ 0.82 (t, 3H, J=7.2 Hz), 1.49 (br m, 2H), 2.61 (t, 2H, J=7.81 Hz), 3.79 (s, 6H), 3.90 (br s, 2H), 6.85 (d, 4H, J=8.8 Hz), 7.08 (dd, I H, J=2.8, 8.7 Hz), 7.20 (d, 4H, J=8.4 Hz), 7.42 (d, 1H, J=2.7 Hz), 7.47 (d, 1 H, J=8.7 Hz).

Step D: Preparation of 3-(4,4'-dimethoxybenzhydryl)-6-(N-methyl-N-isobutyloxycarbonyl)-amino-2-propyl-quinazolin-4(3H)-one To a suspension of 81.5 mg (2.7 mmol) of 80% NaH in 3 mL of dry DMF at 0° C. under nitrogen was added dropwise a solution of 1.03 g (2.5 mmol) of 6-amino-3-(4,4'-dimethoxybenzhydryl)-2-propylquinazolin-4(3H)-one dissolved in 3 mL of DMF. The resulting mixture was stirred for 30 minutes and then treated with 0.35 mL (2.7 mmol) of neat isobutylchloroformate. The solution was stirred for 30 minutes and then treated with 2.97 mL (2.97 mmol) of a 1M solution of lithium bis(trimethylsilyl)amide in THF. The dark solution was stirred for a further 30 minutes at 0° C. and then was treated with 0.2 mL (3.26 mmol) of neat iodomethane. The mixture was stirred overnight at room temperature, poured into 50 mL of EtOAc and washed consecutively with water (2×10 mL), brine (1×10 mL) and dried over MgSO$_4$. The product was purified by flash chromatography over silica gel eluted with 30% EtOAc/hexanes to give 0.9 g (71%) of the title compound as an oil.

¹H-NMR (300 MHz, CDCl₃, ppm): δ 0.82–0.91 (m, 6H), 0.96 (d, 3H, J=6.8 Hz), 1.52 (m, 2H), 1.88 (m, 1H), 2.67 (br t, 2H), 3.35 (s, 3H), 3.80 (s, 6H), 3.90 (d, 2H, J=6.6 Hz), 6.87 (d, 4H, J=8.8 Hz), 7.20 (d, 4H, J=8.8 Hz), 7.61 (m, 1H), 7.78 (m, 1H), 8.01 (d, 1H, 2H).

Step E: Preparation of 6-(N-methyl-N-isobutyloxycarbonyl)amino-2-propylquinazolin-4(3H)-one The product of Step D (0.9 g, 1.7 mmol) was added to 3.0 mL of a 10:1 mixture of trifluoroacetic acid and anisole. The solution was stirred for 4 hours, concentrated in vacuo and the residue was purified by flash chromatography over silica gel eluted with 50% EtOAc/hexanes to give 0.47 g (88%) of the title compound as a white solid.

¹H-NMR (300 MHz, CDCl₃, ppm): δ 0.89 (d, 6H, J=6.7 Hz), 1.07 (t, 3H, J=7.4 Hz), 1.92 (m, 2H), 2.76 (t, 2H, J=7.8 Hz), 3.40 (s, 3H), 3.93 (d, 2H, J=6.6 Hz), 7.70 (m, 2H), 8.10 (d, 1H, J=2.6 Hz).

Step F: Preparation of methyl 2-(2-chloro-4-hydroxymethyl-6-methoxyphenoxy)-2-phenylacetate To a solution of 0.500 g (2.65 mmol) of 3-chloro-4-hydroxy-5-methoxybenzyl alcohol (Bader) and 0.668 g (1.1 eq) of methyl 2-bromophenylacetate dissolved in 5 mL acetone was added 0.733 g (2 eq) of anhydrous potassium carbonate and the reaction mixture was stirred and refluxed overnight. The reaction mixture was cooled to room temperature, filtered and evaporated in vacuo. The residual oil was purified on a silica gel flash chromatography column eluted with 35% ethyl acetate/hexane to afford 0.570 g (64%) of the title compound.

¹H NMR (300 MHz, CDCl₃, ppm): δ 1.65–1.75 (t, 1H), 3.70 (s, 3H), 3.80 (s, 3H), 4.55 (d, 2H), 5.75 (s, 1H), 6.80 (s, 1H), 6.90 (s, 1H), 7.30–7.40 (m, 3H), 7.50–7.60 (m, 2H).

FAB-MS: m/e 337, 339 (M+1, 3:1 ratio).

Step G: Preparation of 2-(4-bromomethyl-2-chloro-6-methoxyphenoxy)-2-phenylacetate To a stirred and cooled (0° C.) solution of 0.570 g (1.69 mmol) of the product of Step F dissolved in 6 mL of CH₂Cl₂ was added 0.702 g (2.11 mmol) of carbon tetrabromide and 0.555 g (2.11 mmol) of triphenylphosphine. After the addition the reaction mixture was allowed to warm to room temperature and was stirred 4 hours. The mixture was then evaporated in vacuo and purified on a silica gel flash chromatography column eluted with 20% ethyl acetate/hexane to afford 0.580 g (86%) of the title compound.

¹H NMR (300 MHz, CDCl₃, ppm): δ 3.75 (s, 3H), 3.80 (s, 3H), 4.35 (s, 2H), 5.65 (s, 1H), 6.80 (s, 1H), 6.95 (s, 1H), 7.30–7.40 (m, 3H), 7.50–7.60 (m, 2H).

FAB-MS: m/e 398, 400, 402 (M+1).

Step H: Preparation of 3-[4-((1-carbomethoxy-1-phenyl)methoxy)-3-chloro-5-methoxyphenyl]-methyl-6-(N-methyl-N-isobutyloxycarbonyl)-amino-2-propylquinazolin-4(3H)-one To a half suspension of 80 mg (0.252 mmol) of the product of Step E in 0.5 mL of anhydrous DMF was added 10.6 mg (1.05 eq) of a 60% oil dispersion of sodium hydride and the reaction mixture was stirred under an N₂ atmosphere. After stirring 40 minutes at room temperature, a solution of 0.111 g (1.1 eq) of the product of Step G dissolved in 0.5 mL DMF was added to the solution of the anion. The reaction mixture was then stirred overnight, then partitioned between water and ethyl acetate. The organic layer was separated, dried (MgSO₄), filtered and evaporated in vacuo. The residual oil was purified on a silica gel flash chromatography column eluted with 40% ethyl acetate/hexane to afford 100 mg (63%) of the title compound.

¹H NMR (300 MHz, CDCl₃, ppm): δ 0.84–1.01 (m, 9H), 1.58–2.02 (m, 3H), 2.63–2.68 (t, 2H), 3.38 (s, 3H), 3.71 (s, 3H), 3.73 (s, 3H), 3.91 (d, 2H), 5.20–5.30 (br s, 2H), 5.72 (s, 1H), 6.58–6.64 (m, 1H), 6.68 (d, 1H), 7.28–7.34 (m, 3H), 7.48–7.55 (m, 2H), 7.61 (d, 1H), 7.72 (d, 1H), 8.07 (d, 1H).

FAB-MS: m/e 636, 638 (M+1, 3:1 ratio).

Step I: Preparation of 3-[4-((1-carboxy-1-phenyl)methoxy)-3-chloro-5-methoxyphenyl]methyl-6-(N-methyl-N-isobutyloxycarbonyl)amino-2-propylquinazolin-4(3H)-one To a solution of 97 mg (0.15 mmol) of the product of Step H dissolved in 2 mL of methanol, was added 0.25 mL of a 1N solution of NaOH and the reaction mixture was stirred at room temperature for 2.5 hours. The reaction mixture was then adjusted to pH 6 with 1N HCl, concentrated in vacuo, and the residue was applied to a silica gel flash chromatography column and eluted with CHCl₃/MeOH/NH₄OH (80:15:1). Evaporation of the purified fractions and drying in vacuo afforded 60 mg (63%) of the title compound.

¹H NMR (300 MHz, CDCl₃, ppm): δ 0.88–1.06 (m, 9H), 1.68–1.82 (m, 2H), 1.85–2.04 (m, 1H), 2.76 (t, 2H), 3.43 (s, 3H), 3.68 (s, 3H), 3.95 (d, 2H), 5.38 (s, 2H), 5.67 (s, 1H), 6.68 (d, 1H), 6.74 (d, 1H), 7.26–7.33 (m, 3H), 7.48–7.54 (m, 2H), 7.72 (d, 1H), 7.82 (dd, 1H), 8.14 (d, 1H).

EXAMPLE 5

3-[4-((1-Carboxy-1-phenyl)methoxy)-3-propylphenyl]methyl-6-(N-methyl-N-iso-butyloxycarbonyl-)amino-2-propylquinazolin-4(3H)-one Step A: Preparation of methyl 4-(2-propen-1-yl)-oxybenzoate A 2 L flask was equipped with a mechanical stirrer, a reflux condenser and a stopper, then charged with 50.05 g (0.329 mol) of methyl 4-hydroxybenzoate, 960 mL of acetone, 22.50 g (1.625 mol) of anhydrous potassium carbonate, 80.5 mL (112.6 g, 0.932 mol) of allyl bromide and the mixture was stirred and refluxed for 14 hours. The mixture was cooled to room temperature, filtered and concentrated to an oil. The residual oil was purified by distillation (97° C. @0.03 mm Hg) to afford 53.52 g (86%) of the title compound.

¹H NMR (300 MHz, CDCl₃, ppm): δ 3.84 (s, 3H), 4.56 (d, J=7 Hz, 2H), 5.28 (dd, J=3,12 Hz, 1H), 5.40 (dd, J=3,19Hz, 1H), 5.96–6.10 (m, 1H), 6.90 (d, J=10 Hz, 2H), 7.96 (d, J=10 Hz, 2H).

FAB-MS: m/e 193 (M+1).

Step B:. Preparation of methyl 4-hydroxy-3-(2-propen-1-yl)benzoate

A solution of 15.05 g (78.3 mmol) of the product of Step A in 25 mL of 1,2-dichlorobenzene was magnetically stirred and refluxed (183° C.) under an argon atmosphere for 18 hours. At this point, the reaction mixture was cooled to room temperature and applied to a 6 cm diameter by 18 cm silica gel flash chromatography column and eluted with 25% ethyl acetate-hexane to separate the 1,2-dichlorobenzene, then with 40% ethyl acetate-hexane to elute the product. The product fractions were concentrated in vacuo and the residual oil was crystallized from hexane to afford 13.70 g (91%) of the title compound.

¹H NMR (300 MHz, CDCl₃, ppm): δ 3.42 (d, J=8 Hz, 2H), 3.88 (s, 3H), 5.14–5.20 (m, 2H), 5.48 (s, 1H), 5.94–6.06 (m, 1H), 6.82 (d, J=12 Hz, 1H), 7.80–7.85 (m, 2H).

FAB-MS: m/e 193 (M+1).

Step C: Preparation of methyl 4-(tert-butyldimethylsilyloxy)-3-(2-propen-1-yl)benzoate To a solution of 5.168 g (26.9 mmol) of the product of Step B in 50 mL of dichloromethane was added 4.40 mL (2.95 mmol) of triethylamine, 4.46 g (2.95 mmol) of tert-butyldimethylchlorosilane, 0.100 g of 4-dimethylaminopyridine, and the reaction mixture was stirred at room temperature for 2 hours. The mixture was then diluted with 50 mL dichloromethane, washed with 100 mL 1N hydrochloric acid, dried (MgSO₄), filtered and evaporated. The residual oil (7.993 g, 97%) was used in the next step without further purification.

¹H NMR (300 MHz, CDCl₃, ppm): δ 0.24 (s, 6H), 1.02 (s, 9H), 3.36 (d, J=8 Hz, 2H), 3.84 (s, 3H), 4.98–5.08 (m, 2H), 5.88–6.03 (m, 1H), 6.78 (d, J=11 Hz, 1H), 7.76–8.40 (m, 2H).

FAB-MS: m/e 307 (M+1).

Step D: Preparation of 4-(tert-butyldimethylsilyloxy)-3-(2-propen-1-yl)benzyl alcohol To a magnetically stirred solution of 8.523 g (28.0 mmol) of the product from Step C in 35 mL of anhydrous THF was added 15.0 mL of a 1.0M solution of lithium aluminum hydride in THF, and the reaction mixture was stirred under a nitrogen atmosphere for 2 hours. At this point, the reaction was quenched by cautious addition of 10 mL water, the resulting precipitate was dissolved by addition of 1.0N hydrochloric acid and the product was extracted into ethyl acetate. The organic layer was separated, dried (MgSO₄), filtered and evaporated in vacuo to afford 7.258 g (93%) of the title compound.

¹H NMR (300 MHz, CDCl₃, ppm): δ 0.20 (s, 6H), 1.00 (s, 9H), 3.34 (d, J=8 Hz, 2H), 3.84 (s, 1H), 4.57 (s, 2H), 4.97–5.07 (m, 2H), 5.88–6.03 (m, 1H), 6.86 (d, J=10 Hz, 1H), 7.05–7.14 (m, 2H).

FAB-MS: m/e 279, 261 (M+1).

Step E: Preparation of 4-hydroxy-3-(2-propen-1-yl)benzyl alcohol

To a solution of approximately 7.26 g (2.6 mmol) of the crude product of Step D, dissolved in 50 mL of anhydrous THF was added 26 mL (2.6 mmol) of tetra-n-butylammonium fluoride and the reaction mixture was stirred at room temperature for 16 hours. The mixture was then evaporated in vacuo and the residual oil was purified on a silica gel flash chromatography column eluted with 5% methanol/chloroform to afford 3.386 g (79%) of the title compound as a colorless oil.

¹H NMR (300 MHz, CDCl₃, ppm): δ 2.12 (br s, 1H), 3.35 (d, J=8 Hz, 2H), 4.54 (s, 3H), 5.05–5.15 (m, 2H), 5.90 (br s, 1H), 5.90–6.05 (m, 1H), 6.70 (d, J=10 Hz, 1H), 7.02–7.10 (m, 2H).

FAB-MS: m/e 165 (M+1).

Step F: Preparation of 4-hydroxy-3-propylbenzyl alcohol

To a solution of 0.370 g (2.25 mmol) of the product of Step E dissolved in 25 mL of absolute ethanol was added 53 mg of a 5% rhodium on carbon catalyst and the mixture was shaken under a 40 psig pressure of hydrogen on a Parr apparatus. After 30 minutes, the reaction mixture was removed, filtered and evaporated in vacuo. The residue was purified on a silica gel flash chromatography column eluted with 35% ethyl acetate/hexane to afford the title compound.

¹H NMR (300 MHz, CDCl₃, ppm): δ 0.95 (t, J=8 Hz, 3H), 1.55–1.68 (m, 2H), 2.22 (br s, 1H), 2.57 (t, J=8 Hz, 2H), 4.56 (s, 2H), 5.93 (br s, 1H), 6.66 (d, J=10 Hz, 1H), 7.00 (dd, J=2, 10 Hz, 1H), 7.08 (d, J=2 Hz, 1H).

FAB-MS: m/e 167 (M+1).

Step G: Preparation of methyl (4-hydroxymethyl-2-propylphenoxy)-2-phenylacetate

To a solution of 0.484 g (2.91 mmol) of the product of Step F dissolved in 12 mL of acetone were added 0.667 g (2.91 mmol) of methyl 2-bromophenylacetate, 0.804 g (5.82 mmol) of anhydrous K₂CO₃ and the mixture was stirred and heated at reflux for 5 hours. The mixture was then cooled, filtered and evaporated in vacuo. The residual oil was purified on a silica gel flash chromatography column eluted with 30% ethyl acetate/hexane to afford 0.756 g (83%) of the title compound.

¹H NMR (300 MHz, CDCl₃, ppm): δ 0.95 (t, J=8 Hz, 3H), 1.58 (br s, 1H), 1.60–1.75 (m, 2H), 2.70 (t, J=8 Hz, 2H), 3.68 (s, 3H), 4.57 (m, 2H), 5.62 (s, 1H), 6.68 (d, J=10 Hz, 1H), 7.07 (dd, J=2, 10 Hz, 1H), 7.16 (d, J=2 Hz, 1H), 7.32–7.44 (m, 3H), 7.55–7.60 (m, 2H).

FAB-MS: m/e 315 (M+1).

Step H: Preparation of methyl (4-bromomethyl-2-propylphenoxy)-2-phenylacetate

To a stirred (0° C.) solution of 0.750 g (2.31 mmol) of the product of Step G, and 0.949 g (2.86 mmol) of carbon tetrabromide dissolved in 7 mL of methylene chloride was added 0.751 g of triphenylphosphine (2.86 mmol) in portions. After the addition was complete, the reaction mixture was stirred and allowed to warm to room temperature over 1 hour. The reaction mixture was then evaporated in vacuo, and the residue was purified on a silica gel flash chromatography column eluted with 10% ethyl acetate/hexane to afford 0.703 g (78%) of the title compound.

¹H NMR (300 MHz, CDCl₃, ppm): δ 0.95 (t, J=8 Hz, 3H), 1.60–1.75 (m, 2H), 2.70 (t, J=8 Hz, 2H), 3.69 (s, 3H), 4.44 (s, 2H), 5.62 (s, 1H), 6.64 (d, J=10 Hz, 1H), 7.12 (dd, J=2, 10 Hz, 1H), 7.18 (d, J=2 Hz, 1H), 7.34–7.44 (m, 3H), 7.53–7.58 (m, 2H).

Step I: Preparation of 3-[4-((1-carboxmethoxy-1-phenyl)methoxy)-3-propylphenyl]methyl-6-(N-methyl-N-isobutyloxycarbonyl)amino-2-propylquinazolin-4(3H)-one To a solution of 115 mg (0.36 mmol) of the product of Step E from Example 4 in 1.5 mL of anhydrous DMF was added 15.0 mg (0.36 mmol) of a 60% oil dispersion of sodium hydride and the reaction mixture was stirred under an N₂ atmosphere. After stirring 45 minutes at room temperature, a solution of 0.37 g (0.36 mmol) of the product of Step H dissolved in 0.5 mL DMF was added to the solution of the anion. The reaction mixture was then stirred an additional hour at room temperature, then partitioned between water and ethyl acetate. The organic layer was separated, dried (MgSO₄), filtered and evaporated in vacuo. The residual oil was purified on a silica gel flash chromatography column eluted with 35% ethyl acetate/hexane to afford 0.060 g (49%) of the title compound.

¹H NMR (300 MHz, CDCl₃, ppm): δ 0.85 (d, 6H), 0.92 (t, 3H), 0.96 (t, 3H), 1.55–2.00 (m, 5H), 2.60–2.75 (m, 4H), 3.36 (s, 3H), 3.77 (s, 3H), 3.90 (d, 2H), 5.28 (br s, 2H), 5.57 (s, 1H), 6.63 (d, 1H), 6.85 (dd, 1H), 6.99 (d, 1H), 7.30–7.42 (m, 3H), 7.50–7.60 (m, 2H), 7.55 (dd, 1H), 7.60 (d, 1H), 8.08 (d, 1H).

FAB-MS: m/e 614 (M+H).

Step J: Preparation of 3-[4-((1-carboxy-1-phenyl)methoxy)-3-propylphenyl]methyl-6-(N-methyl-N- isobutyloxycarbonyl)-amino-2-propylquinazolin-4(3H)-one

To a solution of 60 mg (0.098 mmol) of the product of Step I dissolved in 2 mL of methanol, was added 0.25 mL of a 1N solution of NaOH and the reaction mixture was stirred at room temperature for 4 hours. The reaction mixture was then adjusted to pH 7 with 1N HCl, concentrated in vacuo, and the residue was applied to a silica gel flash chromatography column and eluted with 10% MeOH/CHCl$_3$. Evaporation of the purified fractions and drying in vacuo afforded 33 mg (57%) of the title compound.

$^1$H NMR (300 MHz, CD$_3$OD, ppm): δ 0.88–1.05 (complex, 12 H), 1.56–1.67 (m, 2H), 1.72–1.84 (m, 2H), 1.87–2.00 (m, 1H), 2.55–2.65 (m, 1H), 2.75–2.86 (m, 3H), 3.42 (s, 3H), 3.95 (d, 2H), 5.38 (br s, 2H), 5.43 (s, 1H), 6.85 (d, 1H), 6.94 (dd, 1H), 7.05 (d, 1H), 7.28–7.38 (m, 3H), 7.62–7.70 (m, 2H), 7.71 (d, 1H), 7.83 (dd, 1H), 8.15 (d, 1H).

FAB-MS: m/e 600 (M+H).

EXAMPLE 6

3-[4-(1-Carboxy-1-(3,4-methylenedioxyphenyl))methoxy-3,5-dipropylphenyl]methyl(8-methyl-2-iso-propyl)quinazolin-4(3H)-one Step A: Preparation of 8-methyl-2-iso-propylquinazolin-4-one and 2-(iso-butyryl)-amino-3-methylbenzamide Dimethylaminopyridine (15 mg) followed by triethylamine (4.14 mL, 0.0279 mol) were added to a stirred solution of 2-amino-3-methylbenzoic acid (1.50 g, 0.0099 mol) in DMF (15 mL) under nitrogen at 0° C. The iso-butyryl chloride (2.07 mL, 0.0198 mol) was added dropwise then the mixture stirred at 0° C. for 30 min. followed by 30 min. at room temperature then at 120° C. for 1 hr. The suspension was then stirred at room temperature for 2 days. Ammonium carbonate (3.5 g) was added in portions and the mixture heated at 120° C. for 3 hr. After cooling to room temperature the mixture was poured into ice/water and extracted with ethyl acetate (3 times). The combined organic phase was washed with water, brine, dried (magnesium sulfate) and the solvent removed in vacuo to leave a cream solid. Recrystallisation (1:1 ethyl acetate/hexane) afforded 2-(iso-butyryl)amino-3-methylbenzamide (739 mg, 34%).

$^1$H-NMR 400 MHz (CD$_3$OD): δ 7.38 (t, 2H), 7.25 (t, 1H), 2.68 (quin, 1H), 2.24 (s, 3H), 1.22 (d, 6H);

FAB-MS: 221 (M+H).

The filtrate was evaporated in vacuo and chromatographed on silica gel (25, 30% ethyl acetate/hexane) to give 8-methyl-2-iso-propylquinazolin-4-one (340 mg, 17%).

$^1$H-NMR (CD$_3$OD): δ 7.99 (dd, 1H), 7.62 (m, 1H), 7.32 (t, 1H), 2.91 (quin, 1H), 2.58 (s, 3H), 1.35 (d, 6H);

FAB-MS: 203 (M+1).

Step B: Preparation of 8-methyl-2-iso-propylquinazolin-4-one

5N Sodium hydroxide solution (0.56 mL, 0.0028 mol) was added to a mixture of 2-(iso-butyryl)amino-3-methylbenzamide (0.62 g, 0.0028 mol) in methanol (6 mL) and water (14 mL) at room temperature. The mixture was heated at reflux for 1 hr. then cooled to room temperature and acidified with 2N hydrochloric acid solution. Saturated sodium dihydrogen orthophosphate solution was added and the mixture extracted with methylene chloride (4 times). The combined organic phase was washed with water, brine, dried (magnesium sulfate) and the solvent removed in vacuo to leave 8-methyl-2-iso-propylquinazolin-4-one (0.43 g, 76%) identical with the material isolated in step A.

Step C: Preparation of methyl 2-bromo-2-(3,4-methylenedioxyphenyl)acetate

A mixture of (3,4-methylenedioxyphenyl)acetic acid (4.64 g, 25.74 mMol) in dry DMF (40 mL), cesium carbonate (9.2 g, 25.74 mMol) and methyl iodide (3.7 g, 26.0 mMol) in dry DMF (40 mL) was stirred at room temperature for 3h. At the end of this period, the reaction mixture was poured into ice water and extracted with ethyl acetate. The organic phase was washed with saturated NaHCO$_3$, water, brine and then dried (MgSO$_4$) and filtered. The filtrate was concentrated in vacuo to provide pure methyl (3,4-methylened ioxyphenyl)acetate as an oil (4.38 g).

N-Bromosuccinimide (3.95 g, 22.2 mMol) and AIBN (0.098 g, 0.06 mMol) were added to a solution of methyl (3,4-methylenedioxyphenyl)acetate (3.9 g, 21.2 mMol) and the mixture was refluxed for 2.5 h. The reaction was cooled and filtered. The filtrate was concentrated in vacuo and the residue obtained was purified by flash chromatography on silica-gel using 10% ethyl acetate-hexane. Yield 2.6 g (oil).

$^1$H-NMR (400 MHz, CDCl$_3$, ppm): δ 7.105 (d, 1H), 6.93 (d, 1H), 6.72 (m, 1H), 5.964 (s, 2H), 5.28 (s, 1H), 3.76 (s, 3H).

Step D: Preparation of 4-(1-carbomethoxy-1-(3,4-methylenedioxyphenyl)methoxy)-3,5-dipropylbenzylalcohol To a solution of (3,5-dipropyl-4-hydroxy)benzyl alcohol (0.19 g, 1.0 mMol) in dry DMF (4 mL) were added cesium carbonate (0.33g, 1.01 mMol) and methyl 2-bromo-2-(3,4-methylenedioxyphenyl)acetate (0.272 g, 1.0 mMol) and the mixture was stirred at room temperature for 3h. At the end of this period, the reaction mixture was poured into ice water and extracted with ethyl acetate. The organic phase was washed with water, brine, dried (MgSO$_4$) and then filtered. The filtrate was concentrated in vacuo to provide an oil, which was then purified by flash chromatography on silica-gel using ethyl acetate-hexane (1:4) to provide the titled product as a thick colorless oil (0.30 g).

$^1$H-NMR (200 MHz, CDCl$_3$, ppm): δ 7.05 (s, 1H), 6.97 (s, 2H), 6.88 (d, 1H), 6.75 (d, 1H), 5.97 (s, 2H), 5.00 (s, 1H), 4.55 (s, 2H), 3.74 (s, 3H), 2.38 (m, 4H), 1.45 (m, 4H), 0.82 (t, 6H).

Step E: Preparation of 4-(1-carbomethoxy-1-(3,4-methylenedioxyphenyl)methoxy)-3,5-dipropylbenzylbromide To a solution of the product of Step D (0.53 g, 1.38 mMol) in dry THF (10 mL) were added Ph$_3$P (0.49 g, 2.06 mMol), CBr$_4$ (0.69 g, 2.06 mMol) and CH$_3$CN (2 mL), and the mixture was stirred at room temperature for 14 h. At the end of this period, the reaction mixture was concentrated in vacuo to provide an oil, which was then purified by flash chromatography on silica-gel using ethyl acetate-hexane (1:9) to provide the titled product as a thick colorless oil (0.57 g).

$^1$H-NMR (400 MHz, CDCl$_3$, ppm): δ 7.04 (d, 1H), 7.00 (s, 2H), 6.87 (dd, 1H), 6.76 (d, 1H), 5.97 (s, 2H), 5.00 (s, 1H), 4.41 (s, 2H), 3.73 (s, 3H), 2.36 (m, 4H), 1.45 (m, 4H), 0.82 (t, 6H).

Step F: Preparation of 3-[4-(1-carbomethoxy-1-(3,4-methylenedioxyphenyl))methoxy-3,5-dipropylphenyl]methyl(8-methyl-2-iso-propyl)quinazolin-4(3H)-one Cesium carbonate (57 mg, 0.175 mmol) was added to 8-methyl-2-iso-propylquinazolin-4-one (17.7 mg, 0.0875 mmol) in DMF (1 mL) at room temperature under nitrogen. After stirring for 15 min., a solution of 4-(1-carbomethoxy-1-(3,4-methylenedioxyphenyl)methoxy)-3,5-dipropyl-benzylbromide (52.7 mg, 0.114 mmol), from step E, in DMF (1 mL) was added and the mixture stirred at room temperature for 12 hr. The solvent was removed in vacuo and the residue chromatographed on silica gel (8, 15% ethyl acetate/hexane) to give 3-[4-(1-carbomethoxy-1-(3,4-methylenedioxyphenyl))methoxy-3,5-dipropylphenyl]methyl(8-methyl-2-iso-propyl)-quinazolin-4(3H)-one (32 mg, 63%).

$^1$H-NMR 400 MHz (CDCl$_3$): δ 8.12 (d, 1H), 7.56 (d, 1H), 7.31 (t, 1H), 7.01 (d, 1H), 6.82 (dd, 1H), 6.73 (m, 3H), 5.95 (s, 2H), 5.32 (br. s, 2H), 4.96 (s, 1H), 3.71 (s, 3H), 3.06 (quin, 1H), 2.60 (s, 3H), 2.30 (m, 4H), 1.53 - 1.30 (m, 4H), 1.22 (d, 3H), 1.21 (d, 3H), 0.77 (t, 6H).

Step G: Preparation of 3-[4-(1-carboxy-1-(3,4-methylenedioxyphenyl))-methoxy-3,5-dipropylphenyl]methyl(8-methyl-2-iso-propyl)-quinazolin-4(3H )-one 5N Sodium hydroxide solution (0.1 mL) was added to a stirred mixture of 3-[4-(1-carbomethoxy-1-(3,4-methylenedioxyphenyl))methoxy-3,5-dipropylphenyl]methyl(8-methyl-2-iso-propyl)quinazolin-4(3H)-one (13.2 mg, 0.0226 mmol) in methanol (1 mL). A few drops of methylene chloride were added to allow stirring then the mixture was stirred at room temperature for 2 hr. The solution volume was reduced to ~10% in vacuo then 5% citric acid solution was added. The mixture was extracted with ethyl acetate (3 times). The combined organic phase was washed with water, brine, dried (magnesium sulfate) and the solvent removed in vacuo to leave 3-[4-(1-carboxy-1-(3,4-methylenedioxyphenyl))methoxy-3,5-dipropyl-phenyl]methyl(8-methyl-2-iso-propyl)quinazolin-4(3H)-one (14.2 mg, 100%).

$^1$H-NMR 400 MHz (CD$_3$OD): δ 5 8.04 (d, 1H), 7.64 (d, 1H), 7.36 (t, 1H), 6.96 (d, 1H), 6.88 - 6.70 (m, 4H), 5.95 (s, 2H), 5.40 (s, 2H), 4.97 (s, 1H), 3.17 (quin, 1H), 2.60 (s, 3H), 2.33 (t, 4H), 1.50 - 1.24 (m, 4H), 1.23 (d, 3H), 1.22 (d, 3H), 0.77 (t, 6H);

FAB-MS 593.7 (M+Na), 571.8 (M+H).

EXAMPLE 7

3-[4-(1-Carboxy-1-(3,4-methylenedioxyphenyl))methoxy-3,5-dipropylphenyl]methyl(8-methyl-2-(pent-3-yl))quinazolin-4(3H)-one The title compound was synthesized in a similar manner to that outlined for Example 6 except that in step A iso-butyryl chloride was replaced by 2-ethylbutyryl chloride.

$^1$H-NMR 400 MHz (CDCl$_3$): δ 8.15 (d, 1H), 7.58 (d, 1H), 7.32 (t, 1H), 6.91 (s, 1H), 6.78 (s, 2H), 6.72 (m, 2H), 5.96 (s, 2H), 5.32 (br. s, 1H), 4.99 (s, 1H), 2.69 (m, 1H), 2.56 (s, 3H), 2.28 (t, 4H), 1.76 (m, 2H), 1.59 (m, 2H), 1.40 (m, 4H), 0.78 (m, 6H), 0.68 (m, 6H);

FAB-MS 621.4 (M+Na), 599.6 (M+H).

EXAMPLE 8

3-[4-(1-Carboxy-1-(3,4-methylenedioxyphenyl))methoxy-3,5-dipropylphenyl]methyl(2,8-dimethyl)-quinazolin-4(3H)-one The title compound was synthesized in a similar manner to that outlined for Example 6 except that in step A iso-butyryl chloride was replaced by acetyl chloride.

$^1$H-NMR 400 MHz (CDCl$_3$): δ 8.15 (d, 1H), 7.58 (d, 1H), 7.32 (t, 1H), 6.91 (s, 1H), 6.81 - 6.72 (m, 4H), 5.98 (s, 2H), 5.28 (br. s, 2H), 5.00 (s, 1H), 2.59 (s, 3H), 2.51 (s, 3H), 2.26 (t, 4H), 1.40 (m, 4H), 0.78 (m, 6H);

FAB-MS 543.9 (M+H).

EXAMPLE 9

3-[4-(1-Carboxy-1-(3,4-methylenedioxyphenyl))methoxy-3,5-dipropylphenyl]methyl(8-methyl)quinazolin-4(3H )-one Step A: Preparation of 8-methylquinazolin-4(3H)-one 2-Amino-3-methylbenzoic acid (1.00 g, 0.0066 mol) and formamide (12 mL) were heated together at 130° C. for 20 hr. under nitrogen. After cooling to room temperature, the solid was filtered off, washed with diethyl ether and dried in vacuo to leave 8-methylquinazolin-4(3H)-one (1.19 g).

$^1$H-NMR 400 MHz (CD$_3$OD): δ 8.06 (m, 2H), 7.68 (d, 1H), 7.41 (t, 1H), 2.59 (s, 3H);

EI-MS 160 (M+).

Step B: Preparation of 3-[4-(1-carboxy-1-(3,4-methylenedioxyphenyl))methoxy-3,5-dipropylphenyl]methyl(8-methyl)-quinazolin-4(3H)-one 3-[4-(1-Carboxy-1-(3,4-methylenedioxyphenyl))methoxy-3,5-dipropylphenyl]methyl(8-methyl)quinazolin-4(3H)-one was synthesized from 8-methylquinazolin-4(3H)-one and 3,5-dipropyl-4-(1-methoxy-carbonyl-1-(3,4-methylenedioxyphenyl)methoxy)benzylbromide in a similar manner to that outlined in steps C and D of Example 6.

$^1$H-NMR 400 MHz (CDCl$_3$): δ 8.16 (d, 1H), 8.12 (s, 1H), 7.60 (d, 1H), 7.38 (t, 1H), 6.95 (m, 3H), 6.82 (d, 1H), 6.73 (d, 1H), 5.98 (s, 2H), 5.10 (s, 2H), 5.00 (s, 1H), 2.59 (s, 3H), 2.28 (t, 4H), 1.42 (m, 4H), 0.79 (m, 6H);

FAB-MS 551.7 (M+Na), 529.7 (M+H).

EXAMPLE 10

3-[4-(1-Carboxy-1-(3,4-methylenedioxyphenyl))methoxy-3,5-dipropylphenyl]methyl(8-bromo-2-iso-propyl)quinazolin-4(3H)-one The title compound was synthesized in a similar manner to that outlined for Example 6 except that in step A 2-amino-3-methylbenzoic acid was replaced by 2-amino-3-bromobenzoic acid.

$^1$H-NMR 400 MHz (CDCl$_3$): δ 8.25 (d, 1H), 8.00 (d, 1H), 7.28 (m, 1H), 6.90 (s, 1H), 6.75 (m, 4H), 5.98 (s, 2H), 5.32 (br. s, 2H), 5.01 (s, 1H), 3.06 (m, 1H), 2.28 (t, 4H), 1.41 (m, 4H), 1.29 (d, 6H), 0.78 (t, 6H);

FAB-MS 635.2 (M+H).

EXAMPLE 11

3-[4-(1-Carboxy-1-(3,4-methylenedioxyphenyl))methoxy-3,5-dipropylphenyl]methyl(8-methyl-2-phenyl)-quinazolin-4(3H )-one The title compound was synthesized in a similar manner to that outlined for Example 6 except that in step A iso-butyryl chloride was replaced by benzoyl chloride.

$^1$H-NMR 400 MHz (CD$_3$OD): δ 8.25 (d, 1H), 7.70 (d, 1H), 7.52- 7.32 (m, 6H), 6.95 (s, 1H, 6.85 - 6.76 (m, 2H), 6.45 (s, 2H), 5.98 (s, 2H), 5.28 (br. s, 2H), 4.99 (s, 1H), 2.59 (s, 3H), 2.28 (t, 4H), 1.38 (m, 4H), 0.76 (t, 6H);

FAB-MS 605.7 (M+H).

What is claimed is:

1. A compound of structural formula I

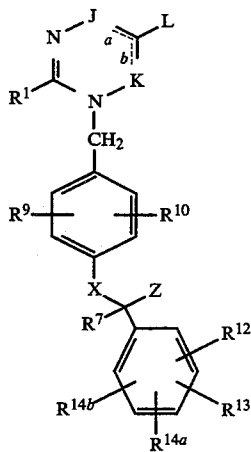

or a pharmaceutically acceptable salt thereof, wherein:
R$^1$ is:
  (a) H,
  (b) (C$_1$–C$_6$)-alkyl, (C$_2$–C$_6$)-alkenyl or (C$_2$–C$_6$)-alkynyl each of which is unsubstituted or substituted with a substituent selected from the group consisting of:
    i) aryl as defined below,
    ii) (C$_3$–C$_7$)-cycloalkyl,
    iii) Cl, Br, I, F,
    iv) OH,
    v) NH$_2$,
    vi) NH(C$_1$–C$_4$)-alkyl,
    vii) N[(C$_1$–C$_4$)-alkyl]$_2$,
    viii) NHSO$_2$R$^2$,
    ix) CF$_3$,
    x) COOR$^2$, or
    xi) SO$_2$NHR$^3$; and
  (c) aryl,
  (d) heteroaryl,
  (e) (C$_1$–C$_4$)-perfluoroalkyl,
  (f) —O—(C$_1$–C$_6$)-alkyl,
  (g) —S(O)$_n$—(C$_1$–C$_9$)-alkyl,
  (h) —CONR$^3$R$^3$, or
  (i) —NR$^3$CO—O—(C$_1$–C$_4$)-alkyl; and
n is: 0 to 2; and
J is: (a) —C(=M)—, (b) J and L are connected together to form a 6-membered aromatic ring substituted with R$^{5a}$, R$^{5b}$, R$^{6a}$ and R$^{6b}$ or (c) J and L are connected together to form a 6-membered aromatic ring containing one nitrogen atom, substituted with R$^{5a}$, R$^{5b}$ and R$^{6b}$; and
K is: (a) —C(=M)—, (b) K and L are connected together to form a 6-membered aromatic ring substituted with R$^{5a}$, R$^{5b}$, R$^{6a}$ and R$^{6b}$, or (c) K and L are connected together to form a 6-membered aromatic ring containing one nitrogen atom, substituted on the carbon atoms with R$^{5a}$, R$^{5b}$ and R$^{6b}$; and
one of a or b is a double bond in Formula I provided that when J is —C(=M)— then b is a double bond and when K is —C(=M)— then a is a double bond;
L is the point of attachment of the 6-membered fused aromatic ring optionally containing one nitrogen atom; and
M is: O, S or NR$^{11}$; and
R$^2$ is:
  (a) H, or
  (b) (C$_1$–C$_6$)-alkyl; and
R$^3$ is:
  (a) R$^2$,
  (b) CH$_2$-aryl,
  (c) aryl, or
  (d) (C$_3$–C$_7$)-cycloalkyl; and
R$^4$ groups are independently:
  (a) H,
  (b) (C$_1$–C$_6$)-alkyl or (C$_2$–C$_6$)-alkenyl each of which is unsubstituted or substituted with one of the following substituents,
    i) —OH,
    ii) —O—(C$_1$–C$_4$)-alkyl,
    iii) —S(O)$_n$—(C$_1$–C$_4$)-alkyl,
    iv) —NR$^3$—(C$_1$–C$_4$)-alkyl,
    v) —NHR$^3$,
    vi) —COOR$^3$,
    vii) —CONHR$^3$,
    ix) —CONR$^3$R$^{11}$, or
    x) (C$_3$–C$_7$)-cycloalkyl,
  (c) (C$_3$–C$_7$)-cycloalkyl,
  (d) F, Cl, Br, I,
  (e) CF$_3$,
  (f) —COOR$^3$,
  (g) —CONR$^3$R$^{11}$,
  (h) —NR$^3$R$^{11}$,
  (i) —NR$^3$CONR$^3$R$^{11}$,
  (j) —NR$^3$COOR$^{11}$,
  (k) —SO$_2$NR$^3$R$^{11}$,
  (l) —O—(C$_1$–C$_4$)-alkyl,
  (m) —S(O)$_n$—(C$_1$–C$_4$)-alkyl, or
  (n) —NHSO$_2$R$^{11}$; and
R$^{5a}$ and R$^{5b}$ are independently:
  (a) H,
  (b) (C$_1$–C$_6$)-alkyl, (C$_2$–C$_6$)-alkenyl or (C$_2$–C$_6$)-alkynyl,
  (c) Cl, Br, I, F,
  (d) CF$_3$, or
  (e) when R$^{5a}$ and R$^{5b}$ are bonded to adjacent carbon atoms, they can be joined to form a phenyl ring;
R$^{6a}$ and R$^{6b}$ are independently:
  (a) H,
  (b) aryl-(C$_1$–C$_4$)-alkyl,
  (c) heteroaryl-(C$_1$–C$_4$)-alkyl,
  (d) (C$_1$–C$_6$)-alkyl, which is unsubstituted or substituted with a substituent selected from the group consisting of: —CON(R$^3$)$_2$, -heteroaryl, —S(O)$_n$—R$^{15}$, -tetrazol-5-yl, —CONHSO$_2$R$^{15}$, —SO$_2$NH-heteroaryl, —SO$_2$NHCOR$^{15}$, —PO(OR$^2$)$_2$, —PO(OR$^3$)$_2$, —SO$_2$NH—CN, —NR$^2$COOR$^{15}$, —OH, —NH$_2$, guanidino, (C$_1$–C$_4$)-alkoxy, (C$_1$–C$_4$)-alkylthio, (C$_1$–C$_4$)-alkylamino, (C$_1$–C$_4$)-dialkylamino, —COOR$^3$, —CONHR$^3$, —O—COR$^3$, or aryl,
  (e) —CO-aryl,
  (f) (C$_3$–C$_7$)-cycloalkyl,
  (g) Cl, Br, I, F,
  (h) —OR$^{11}$,
  (i) —SH,
  (j) —S(O)$_n$—(C$_1$–C$_4$)-alkyl,
  (k) —COR$^3$,
  (l) —CO$_2$H,
  (m) —CO$_2$—(C$_1$–C$_4$)-alkyl,
  (n) —SO$_3$H,
  (o) —NR$^2$R$^{15}$,
  (p) —NR$^2$COR$^{15}$,
  (q) —NR$^2$COOR$^{15}$, (r) —SO$_2$NHR$^3$,
(s) —SO$_2$NR$^2$R$^3$,
(t) —NO$_2$,
(u) —NHSO$_2$CF$_3$,
(v) —CONR$^3$R$^3$,
(w) —(C$_1$–C$_4$)-perfluoroalkyl,
(x) —COOR$^2$,
(y) —SO$_3$H,
(z) —N(R$^2$)SO$_2$R$^{15}$,
(aa) —NR$^2$CONR$^3$R$^{15}$,
(bb) —OC(=O)NR$^{15}$R$^3$,
(cc) -aryl,
(dd) —NHSO$_2$CF$_3$,
(ee) —SO$_2$NH-heteroaryl,
(ff) —SO$_2$NHCOR$^{15}$,
(gg) —CONHSO$_2$R$^{15}$,
(hh) —PO(OR$^2$)$_2$,
(ii) -tetrazol-5-yl,
(jj) —CONH(tetrazol-5-yl), or
(kk) —SO$_2$NHCN; and R$^7$ is:
(a) H,
(b) (C$_1$–C$_6$)-alkyl, unsubstituted or substituted with:
  (i) -aryl,
  (ii) —(C$_3$–C$_7$)-cycloalkyl,
  (iii) —NR$^3$R$^{11}$,
  (iv) -morpholin-4-yl,
  (v) —OH,
  (vi) —CO$_2$R$^3$, or
  (vii) —CON(R$^3$)$_2$,
(c) aryl, unsubstituted as defined below or substituted with a substituent selected from the group consisting of:
  i) (C$_1$–C$_4$)-alkyl,
  ii) —O—(C$_1$–C$_4$)-alkyl,
  iii) —CONR$^3$R$^{11}$,
  iv) F, Cl, Br or I, or
  v) —COOR$^3$;

R$^8$ is:
(a) H,
(b) (C$_1$–C$_4$)-alkyl, wherein alkyl is unsubstituted or substituted with one or two substituents selected from the group consisting of:
  i) —OH,
  ii) —NR$^3$R$^{11}$,
  iii) —COOR$^3$,
  iv) —CONHR$^3$, or
  v) —CONR$^3$R$^{11}$;

R$^9$ and R$^{10}$ are independently:
(a) H,
(b) (C$_1$–C$_6$)-alkyl, unsubstituted or substituted with (C$_3$–C$_7$)-cycloalkyl,
(c) (C$_2$–C$_6$)-alkenyl,
(d) (C$_2$–C$_6$)-alkynyl,
(e) Cl, Br, F, I,
(f) (C$_1$–C$_6$)-alkoxy,
(g) when R$^9$ and R$^{10}$ are on adjacent carbons, they can be joined to form a phenyl ring,
(h) perfluoro-(C$_1$–C$_6$)-alkyl,
(i) (C$_3$–C$_7$)-cycloalkyl, unsubstituted or substituted with (C$_1$–C$_6$)-alkyl,
(j) aryl,
(k) (C$_1$–C$_6$)-alkyl—S(O)$_n$—(CH$_2$)$_n$—,
(l) hydroxy-(C$_1$–C$_6$)-alkyl or dihydroxy-(C$_1$–C$_6$)-alkyl,
(m) —CF$_3$,
(n) —CO$_2$R$^3$,
(o) —OH,
(p) —NR$^3$R$^{11}$,
(q) —[(C$_1$–C$_6$)-alkyl]NR$^3$R$^{11}$,
(r) —NO$_2$,
(s) —(CH$_2$)$_n$—SO$_2$—N(R$^3$)$_2$,
(t) —NR$^3$CO—(C$_1$–C$_4$)-alkyl, or
(u) —CON(R$^3$)$_2$;

R$^{11}$ is:
(a) H,
(b) (C$_1$–C$_6$)-alkyl,
(c) allyl,
(d) (C$_3$–C$_6$)-cycloalkyl,
(e) (C$_1$–C$_4$)-acyl,
(f) benzyl, or
(g) phenyl; and R$^{14a}$ and R$^{14b}$ are independently:
(a) H,
(b) F, Cl, Br, or I,
(c) —NO$_2$,
(d) —NH$_2$,
(e) —NH(C$_1$–C$_4$)-alkyl,
(f) —N[(C$_1$–C$_4$)-alkyl]$_2$,
(g) —SO$_2$NHR$^3$,
(h) —CF$_3$,
(i) (C$_1$–C$_4$)-alkyl,
(j) —OR$^3$,
(k) —S(O)$_n$—(C$_1$–C$_4$)-alkyl,
(l) —NHCO—(C$_1$–C$_4$)-alkyl,
(m) —NHCO—O(C$_1$–C$_4$)-alkyl,
(n) —CH$_2$O—(C$_1$–C$_4$)-alkyl,
(o) —O—(CH$_2$)m—OR$^3$,
(p) —CONR$^3$R$^{11}$, or
(q) —COOR$^3$ and m is 2, 3, or 4; and R$^{12}$ and R$^{13}$ are on adjacent carbon atoms are joined together to form a ring structure:

A represents:
a) —Y—C(R$^4$)=C(R$^4$)—,
b) —Y—C(R$^4$)=N—,
c) —Y—N=C(R$^4$)—,
d) —Y—[C(R$^8$)(R$^8$)]s—Y—,
e) —Y—C(R$^8$)(R$^8$)—C(R$^8$)(R$^8$)—,
f) —C(R$^4$)=C(R$^4$)—Y—,
g) —N=C(R$^4$)—Y—,
h) —C(R$^8$)(R$^8$)—C(R$^8$)(R$^8$)—Y—, or
i) —C(R$^4$)=C(R$^4$)—C(R$^4$)=C(R$^4$)—; and s is 1 or 2; and Y is —O—, —S(O)$_n$— and NR$^3$; and X is:
(a) —O—,
(b) —S(O)$_n$—,
(c) —NR$^3$—,
(d) —CH$_2$O—,
(e) —CH$_2$S(O)$_n$—,
(f) —CH$_2$NR$^3$—,
(g) —OCH$_2$—,
(h) —NR$^3$CH$_2$—,
(i) —S(O)$_n$CH$_2$—, or
(j) single bond; and R$^{15}$ is:
(a) aryl, or (b) (C₁–C₄)-alkyl, is unsubstituted or substituted with:
 i) NH₂,
 ii) NH[(C₁–C₄)-alkyl],
 iii) N[(C₁–C₄)-alkyl]₂,
 iv) CO₂H,
 v) CO₂(C₁–C₄)-alkyl,
 vi) OH,
 vii) SO₃H, or
 viii) SO₂NH₂; and Z is:
 (a) —CO₂H,
 (b) —CO₂R¹⁶,
 (c) -tetrazol-5-yl,
 (d) —CONH(tetrazol-5-yl)
 (e) —CONHSO₂-aryl,
 (f) —CONHSO₂-(C₁–C₈)-alkyl, wherein the alkyl group is unsubstituted or substituted with a substituent selected from the group consisting of: —OH, —SH, —O(C₁–C₄)-alkyl, —S—(C₁–C₄)-alkyl, —CF₃, Cl, Br, F, I, —NO₂, —CO₂H, —CO₂—(C₁–C₄)-alkyl, —NH₂, —NH[(C₁–C₄)-alkyl], —N[(C₁–C₄)-alkyl]₂; and
 (g) —CONHSO₂—(C₁–C₄)-perfluoroalkyl,
 (h) —CONHSO₂-heteroaryl,
 (i) —CONHSO₂NR³R³,
 (j) —SO₂NHCO-aryl,
 (k) —SO₂NHCO-(C₁–C₈)-alkyl, wherein the alkyl group is unsubstituted or substituted with a substituent selected from the group consisting of: —OH, —SH, —O(C₁–C₄)-alkyl, —S—(C₁–C₄)-alkyl, —CF₃, Cl, Br, F, I, —NO₂, —CO₂H, —CO₂—(C₁–C₄)-alkyl, —NH₂, —NH[(C₁–C₄)-alkyl], —N[(C₁–C₄)-alkyl]₂,
 (l) —SO₂NHCO—(C₁–C₄)-perfluoroalkyl,
 (m) —SO₂NHCO-heteroaryl,
 (n) —SO₂NHCONR³R³,
 (o) —PO(OH)₂,
 (p) —PO(OR²)₂, or
 (q) —PO(OH)(OR²); and R¹⁶ is:
 (a) (C₁–C₄)-alkyl,
 (b) CHR¹⁷—O—COR¹⁸,
 (c) CH₂CH₂—N[(C₁–C₂)-alkyl]₂,
 (d) CH₂CH₂—N[CH₂CH₂]₂O,
 (e) (CH₂CH₂O)ᵧ—O—[(C₁–C₄)-alkyl], wherein y is 1 or 2,
 (f) aryl or CH₂-aryl, where aryl is unsubstituted as defined below or substituted with CO₂(C₁–C₄)-alkyl,

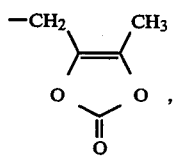 (g)

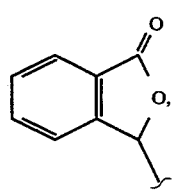 (h)

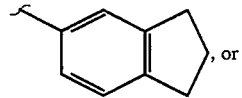 (i)

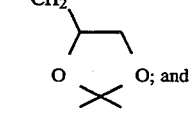 (j)

R¹⁷ and R¹⁸ independently are: (C₁–C₆)-alkyl or phenyl;

aryl is defined as phenyl or naphthyl unsubstituted or substituted with 1 or 2 substituents selected from the group consisting of:
 i) Br, I, Cl, F,
 ii) (C₁–C₄)-alkyl,
 iii) (C₁–C₄)-alkoxy,
 iv) NO₂
 v) CF₃
 vi) SO₂NR³R³,
 vii) (C₁–C₄)-alkylthio,
 viii) hydroxy,
 ix) amino,
 x) (C₃–C₇)-cycloalkyl,
 xi) (C₃–C₁₀)-alkenyl; and heteroaryl is defined as a 5- or 6-membered heteroaromatic moiety selected from the group consisting of thienyl, furanyl, thiazolyl, oxazolyl, pyridyl or pyrimidinyl, which is unsubstituted, mono- or disubstituted with substituents selected from the group consisting of:
 i) Cl, Br, I, or F,
 ii) OH,
 iii) SH,
 iv) NO₂,
 v) (C₁–C₄)-alkyl,
 vi) (C₂–C₄)-alkenyl,
 vii) (C₂–C₄)-alkynyl,
 viii) (C₁–C₄)-alkoxy, or
 ix) CF₃.

2. The compound of claim 1 or a pharmaceutically acceptable salt thereof, wherein R¹ is:
 (a) H,
 (b) (C₁–C₆)-alkyl, (C₂–C₆)-alkenyl or (C₂–C₆)-alkynyl each of which is unsubstituted or substituted with a substituent selected from the group consisting of:
  i) (C₃–C₇)-cycloalkyl,
  ii) CF₃,
  iii) (C₁–C₄)-alkylthio,
  iv) (C₁–C₄)-alkoxy,
 (c) (C₁–C₄)-perfluoroalkyl,
 (d) —O—(C₁–C₆)-alkyl,
 (e) —S(O)ₙ—(C₁–C₉)-alkyl,
 (f) —CONR³R³, or
 (g) —NR³CO—O—(C₁–C₄)-alkyl; and n is: 0, 1, or 2; and J is: (a) —C(=M)—, (b) J and L are connected together to form a 6-membered aromatic ring substituted with R⁵ᵃ, R⁵ᵇ, R⁶ᵃ and R⁶ᵇ or (c) J and L are connected together to form a 6-membered aromatic ring containing one nitrogen atom, substituted with R⁵ᵃ, R⁵ᵇ and R⁶ᵇ; and K is: (a) —C(=M)—, or (b) K and L are connected together to form a 6-membered aromatic ring substituted with $R^{5a}$, $R^{5b}$, $R^{6a}$ and $R^{6b}$, or (c) K and L are connected together to form a six-membered aromatic ring containing one nitrogen atom substituted with $R^{5a}$, $R^{5b}$ and $R^{6b}$ provided that one and only one of J and K is —C(=M)—; and one of a or b is a double bond in Formula I provided that when J is —C(=M)—, then b is a double bond and when K is —C(=M)—, then a is a double bond;

L is: the point of attachment of the 6-membered fused aromatic ring optionally containing one nitrogen atom; and M is: O, S or $NR^{11}$; and $R^2$ is:
 (a) H,
 (b) $(C_1-C_6)$-alkyl; and $R^3$ is:
 (a) $R^2$,
 (b) —$CH_2$-aryl, or
 (c) aryl; and $R^4$ groups are independently:
 (a) H,
 (b) $(C_1-C_6)$-alkyl or $(C_2-C_6)$-alkenyl each of which is unsubstituted or substituted with one of the following substituents,
  i) —OH,
  ii) —O—$(C_1-C_4)$-alkyl,
  iii) —$S(O)_n$—$(C_1-C_4)$-alkyl,
  iv) —$NR^3$—$(C_1-C_4)$-alkyl,
  v) —$NHR^3$,
  vi) —$COOR^3$,
  vii) —$CONHR^3$,
  ix) —$CONR^3R^{11}$, or
  x) $(C_3-C_7)$-cycloalkyl,
 (c) $(C_3-C_7)$-cycloalkyl,
 (d) F, Cl, Br, I,
 (e) $CF_3$,
 (f) —$COOR^3$,
 (g) —$CONR^3R^{11}$,
 (h) —$NR^3R^{11}$,
 (i) —$NR^3CONR^3R^{11}$,
 (j) —$NR^3COOR^{11}$,
 (k) —$SO_2NR^3R^{11}$,
 (l) —O—$(C_1-C_4)$-alkyl,
 (m) —$S(O)_n$—$(C_1-C_4)$-alkyl, or
 (n) —$NHSO_2R^{11}$; and $R^{5a}$ and $R^{5b}$ are independently:
 (a) H,
 (b) $(C_1-C_6)$-alkyl, $(C_2-C_6)$-alkenyl or $(C_2-C_6)$-alkynyl,
 (c) Cl, Br, I, F,
 (d) $CF_3$, or
 (e) when $R^{5a}$ and $R^{5b}$ are bonded to adjacent carbon atoms, they can be joined to form a phenyl ring;

$R^{6a}$ and $R^{6b}$ are independently:
 (a) H,
 (b) aryl-$(C_1-C_4)$-alkyl,
 (c) heteroaryl-$(C_1-C_4)$-alkyl,
 (d) $(C_1-C_6)$-alkyl, is unsubstituted or substituted with a substituent selected from the group consisting of: —$CON(R^3)_2$, -heteroaryl, —$S(O)_n$—$R^{15}$, -tetrazol-5-yl, —$CONHSO_2R^{15}$, —$SO_2NH$-heteroaryl, —$SO_2NHCOR^{15}$, —PO($OR^2)_2$, —PO($OR^3)_2$, —$SO_2NH$—CN, —$NR^2COOR^{15}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^3$, —$CONHR^3$, —O—$COR^3$, or aryl,
 (e) —CO-aryl,
 (f) $(C_3-C_7)$-cycloalkyl,
 (g) Cl, Br, I, F,
 (h) —$OR^{11}$,
 (i) —SH,
 (j) —$S(O)_n$—$(C_1-C_4)$-alkyl,
 (k) —$COR^3$,
 (l) —$CO_2H$,
 (m) —$CO_2$—$(C_1-C_4)$-alkyl,
 (n) —$SO_3H$,
 (o) —$NR^2R^{15}$,
 (p) —$NR^2COR^{15}$,
 (q) —$NR^2COOR^{15}$,
 (r) —$SO_2NHR^3$,
 (s) —$SO_2NR^2R^3$,
 (t) —$NO_2$,
 (u) —$NHSO_2CF_3$,
 (v) —$CONR^3R^3$,
 (w) —$(C_1-C_4)$-perfluoroalkyl,
 (x) —$COOR^2$,
 (y) —$SO_3H$,
 (z) —$N(R^2)SO_2R^{15}$,
 (aa) —$NR^2CONR^3R^{15}$,
 (bb) —$OC(=O)NR^{15}R^3$,
 (cc) -aryl,
 (dd) —$NHSO_2CF_3$,
 (ee) —$SO_2NH$-heteroaryl,
 (ff) —$SO_2NHCOR^{15}$,
 (gg) —$CONHSO_2R^{15}$,
 (hh) —PO($OR^2)_2$;
 (ii) -tetrazol-5-yl,
 (jj) —CONH(tetrazol-5-yl), or
 (kk) —$SO_2NHCN$; and $R^7$ is:
 (a) H,
 (b) $(C_1-C_6)$-alkyl, unsubstituted or substituted with:
  (i) -aryl,
  (ii) —$(C_3-C_7)$-cycloalkyl,
  (iii) —$NR^3R^{11}$,
  (iv) -morpholin-4-yl,
  (v) —OH,
  (vi) —$CO_2R^3$, or
  (vii) —$CON(R^3)_2$,
 (c) aryl, unsubstituted as defined below or substituted with a substituent selected from the group consisting of:
  i) $(C_1-C_4)$-alkyl,
  ii) —O—$(C_1-C_4)$-alkyl,
  iii) —$CONR^3R^{11}$,
  iv) F, Cl, Br or I, or
  v) —$COOR^3$;

$R^9$ and $R^{10}$ are independently:
 (a) H,
 (b) $(C_1-C_6)$-alkyl, unsubstituted or substituted with $(C_3-C_7)$-cycloalkyl,
 (c) $(C_2-C_6)$-alkenyl,
 (d) $(C_2-C_6)$-alkynyl,
 (e) Cl, Br, F, I,
 (f) $(C_1-C_6)$-alkoxy,
 (g) when $R^9$ and $R^{10}$ are on adjacent carbons, they can be joined to form a phenyl ring,
 (h) perfluoro-$(C_1-C_6)$-alkyl,
 (i) $(C_3-C_7)$-cycloalkyl, unsubstituted or substituted with $(C_1-C_6)$-alkyl, (j) aryl,
(k) $(C_1-C_6)$-alkyl—$S(O)_n$—$(CH_2)_n$—,
(l) hydroxy-$(C_1-C_6)$-alkyl or dihydroxy-$(C_1-C_6)$-alkyl,
(m) —$CF_3$,
(n) —$CO_2R^3$,
(o) —OH,
(p) —$NR^3R^{11}$,
(q) —$[(C_1-C_6)$-alkyl$]NR^3R^{11}$,
(r) —$NO_2$,
(s) —$(CH_2)_n$—$SO_2$—$N(R^3)_2$,
(t) —$NR^3CO$—$(C_1-C_4)$-alkyl, or
(u) —$CON(R^3)_2$;

$R^{14a}$ and $R^{14b}$ are independently:
(a) H,
(b) F, Cl, Br, or I,
(c) —$NO_2$,
(d) —$NH_2$,
(e) —$NH(C_1-C_4)$-alkyl,
(f) —$N[(C_1-C_4)$-alkyl$]_2$,
(g) —$SO_2NHR^3$,
(h) —$CF_3$,
(i) $(C_1-C_4)$-alkyl,
(j) —$OR^3$,
(k) —$S(O)_n$—$(C_1-C_4)$-alkyl,
(l) —NHCO—$(C_1-C_4)$-alkyl,
(m) —NHCO—$O(C_1-C_4)$-alkyl,
(n) —$CH_2O$—$(C_1-C_4)$-alkyl,
(o) —O—$(CH_2)m$—$OR^3$,
(p) —$CONR^3R^{11}$, or
(q) —$COOR^3$ and m is 2, 3, or 4; and $R^{12}$ and $R^{13}$ are on adjacent carbon atoms are joined together to form a ring structure:

A represents:
a) —Y—$C(R^4)$=$C(R^4)$—,
b) —Y—$C(R^4)$=N—,
c) —Y—N=$C(R^4)$—,
d) —Y—$[C(R^8)(R^8)]s$ —Y—,
e) —Y—$C(R^8)(R^8)$—$C(R^8)(R^8)$—,
f) —$C(R^4)$=$C(R^4)$—Y—,
g) —N=$C(R^4)$—Y—,
h) —$C(R^8)(R^8)$—$C(R^8)(R^8)$—Y—, or
i) —$C(R^4)$=$C(R^4)$—$C(R^4)$=$C(R^4)$—; and s is 1 or 2; and
Y is —O—, —$S(O)_n$— and $NR^3$; and
X is:
(a) —O—,
(b) —$S(O)_n$—,
(c) —$NR^3$—
(d) —$CH_2O$—,
(e) —$CH_2S(O)_n$—,
(f) —$CH_2NR^3$—,
(g) —$OCH_2$—,
(h) —$NR^3CH_2$—,
(i) —$S(O)_nCH_2$—, or
(j) single bond; and $R^{15}$ is:
(a) aryl, or
(b) $(C_1-C_4)$-alkyl, is unsubstituted or substituted with:
i) $NH_2$,
ii) $NH[(C_1-C_4)$-alkyl],
iii) $N[(C_1-C_4)$-alkyl$]_2$,
iv) $CO_2H$,
v) $CO_2(C_1-C_4)$-alkyl,
vi) OH,
vii) $SO_3H$, or
viii) $SO_2NH_2$; and Z is:
(a) —$CO_2H$,
(b) —$CO_2R^{16}$,
(c) -tetrazol-5-yl,
(d) —CONH(tetrazol-5-yl),
(e) —$CONHSO_2$-aryl,
(f) —$CONHSO_2$-$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —$NH[(C_1-C_4)$-alkyl], —$N[(C_1-C_4)$-alkyl$]_2$; and
(g) —$CONHSO_2$—$(C_1-C_4)$-perfluoroalkyl,
(h) —$CONHSO_2$-heteroaryl,
(i) —$CONHSO_2NR^3R^3$,
(j) —$SO_2NHCO$-aryl,
(k) —$SO_2NHCO$-$(C_1-C_8)$-alkyl, wherein the alkyl group is unsubstituted or substituted with a substituent selected from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —$NH[(C_1-C_4)$-alkyl], —$N[(C_1-C_4)$-alkyl$]_2$; and
(l) —$SO_2NHCO$—$(C_1-C_4)$-perfluoroalkyl,
(m) —$SO_2NHCO$-heteroaryl, or
(n) —$SO_2NHCONR^3R^3$; and $R^{16}$ is:
(a) $(C_1-C_4)$-alkyl,
(b) $CHR^{17}$—O—$COR^{18}$,
(c) $CH_2CH_2$—$N[(C_1-C_2)$-alkyl$]_2$,
(d) $CH_2CH_2$—$N[CH_2CH_2]_2O$,
(e) $(CH_2CH_2O)_y$—O—$[(C_1-C_4)$-alkyl], wherein y is 1 or 2,
(f) aryl or $CH_2$-aryl, where aryl is unsubstituted as defined below or substituted with $CO_2(C_1-C_4)$-alkyl,

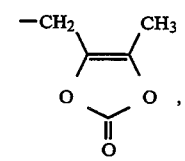

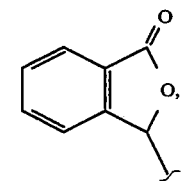

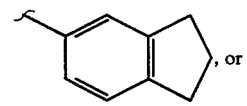

-continued

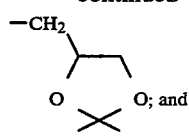
(j)

R$^{17}$ and R$^{18}$ independently are: (C$_1$–C$_6$)-alkyl or phenyl;

aryl is defined as phenyl or naphthyl unsubstituted or substituted with 1 or 2 substituents selected from the group consisting of:
i) Br, I, Cl, F,
ii) (C$_1$–C$_4$)-alkyl,
iii) (C$_1$–C$_4$)-alkoxy,
iv) NO$_2$
v) CF$_3$
vi) SO$_2$NR$^3$R$^3$,
vii) (C$_1$–C$_4$)-alkylthio,
viii) hydroxy,
ix) amino,
x) (C$_3$–C$_7$)-cycloalkyl,
xi) (C$_3$–C$_{10}$)-alkenyl; and heteroaryl is defined as a 5- or 6-membered heteroaromatic moiety selected from the group consisting of thienyl, furanyl, thiazolyl, oxazolyl, pyridyl or pyrimidinyl, which is unsubstituted, mono- or disubstituted with substituents selected from the group consisting of:
i) Cl, Br, I, or F,
ii) OH,
iii) SH,
iv) NO$_2$,
v) (C$_1$–C$_4$)-alkyl,
vi) (C$_2$–C$_4$)-alkenyl,
vii) (C$_2$–C$_4$)-alkynyl,
viii) (C$_1$–C$_4$)-alkoxy, or
ix) CF$_3$.

3. The compound of claim 2 or a pharmaceutically acceptable salt thereof, wherein:

R$^1$ is:
(a) H,
(b) (C$_1$–C$_6$)-alkyl, (C$_2$–C$_6$)-alkenyl or (C$_2$–C$_6$)-alkynyl each of which is unsubstituted or substituted with a substituent selected from the group consisting of:
i) (C$_3$–C$_7$)-cycloalkyl,
ii) CF$_3$,
iii) (C$_1$–C$_4$)-alkylthio,
iv) (C$_1$–C$_4$)-alkoxy,
(c) (C$_1$–C$_4$)-perfluoroalkyl,
(d) —CONR$^3$R$^3$, or
(e) —NR$^3$CO—O—(C$_1$–C$_4$)-alkyl; and n is: 0, 1, or 2; and J is: (a) —C(=M)—, or (b) J and L are connected together to form a 6-membered aromatic ring substituted with R$^{5a}$, R$^{5b}$, R$^{6a}$ and R$^{6b}$;

K is: (a) —C(=M)—, or (b) K and L are connected together to form a 6-membered aromatic ring substituted with R$^{5a}$, R$^{5b}$, R$^{6a}$ and R$^{6b}$, provided that one and only one of J and K is —C(=M)—; and one of a or b is a double bond in Formula I provided that when J is —C(=M)—, then b is a double bond and when K is —C(=M)—, then a is a double bond;

L is: the point of attachment of the 6-membered fused aromatic ring optionally containing one nitrogen atom; and M is: O, S or NR$^{11}$; and R$^2$ is:
(a) H,
(b) (C$_1$–C$_6$)-alkyl; and R$^3$ is:
(a) R$^2$,
(b) —CH$_2$-aryl, or
(c) aryl; and R$^4$ groups are independently:
(a) H,
(b) (C$_1$–C$_6$)-alkyl or (C$_2$–C$_6$)-alkenyl each of which is unsubstituted or substituted with one of the following substituents,
i) —OH,
ii) —O—(C$_1$–C$_4$)-alkyl,
iii) —S(O)$_n$—(C$_1$–C$_4$)-alkyl,
iv) —NR$^3$—(C$_1$–C$_4$)-alkyl,
v) —NHR$^3$,
vi) —COOR$^3$,
vii) —CONHR$^3$,
ix) —CONR$^3$R$^{11}$, or
x) (C$_3$–C$_7$)-cycloalkyl,
(c) (C$_3$–C$_7$)-cycloalkyl,
(d) F, Cl, Br, I,
(e) CF$_3$,
(f) —COOR$^3$,
(g) —CONR$^3$R$^{11}$,
(h) —NR$^3$R$^{11}$,
(i) —NR$^3$CONR$^3$R$^{11}$,
(j) —NR$^3$COOR$^{11}$,
(k) —SO$_2$NR$^3$R$^{11}$,
(l) —O—(C$_1$–C$_4$)-alkyl,
(m) —S(O)$_n$—(C$_1$–C$_4$)-alkyl, or
(n) —NHSO$_2$R$^{11}$; and R$^{5a}$ and R$^{5b}$ are independently:
(a) H,
(b) (C$_1$–C$_6$)-alkyl, (C$_2$–C$_6$)-alkenyl or (C$_2$–C$_6$)-alkynyl,
(c) Cl, Br, I, F,
(d) CF$_3$, or
(e) when R$^{5a}$ and R$^{5b}$ are bonded to adjacent carbon atoms, they can be joined to form a phenyl ring;

R$^{6a}$ and R$^{6b}$ are independently:
(a) H,
(b) aryl-(C$_1$–C$_4$)-alkyl,
(c) heteroaryl-(C$_1$–C$_4$)-alkyl,
(d) (C$_1$–C$_6$)-alkyl, is unsubstituted or substituted with a substituent selected from the group consisting of: —CON(R$^3$)$_2$, -heteroaryl, —S(O)$_n$—R$^{15}$, -tetrazol-5-yl, —CONHSO$_2$R$^{15}$, —SO$_2$NH-heteroaryl, —SO$_2$NHCOR$^{15}$, —PO(OR$^2$)$_2$, —PO(OR$^3$)$_2$, —SO$_2$NH—CN, —NR$^2$COOR$^{15}$, —OH, —NH$_2$, guanidino, (C$_1$–C$_4$)-alkoxy, (C$_1$–C$_4$)-alkylthio, (C$_1$–C$_4$)-alkylamino, (C$_1$–C$_4$)-dialkylamino, —COOR$^3$, —CONHR$^3$, —O—COR$^3$, or aryl,
(e) —CO-aryl,
(f) (C$_3$–C$_7$)-cycloalkyl,
(g) Cl, Br, I, F,
(h) —OR$^{11}$,
(i) —SH,
(j) —S(O)$_n$—(C$_1$–C$_4$)-alkyl,
(k) —COR$^3$,
(l) —CO$_2$H, (m) —CO₂—(C₁-C₄)-alkyl,
(n) —SO₃H,
(o) —NR²R¹⁵,
(p) —NR²COR¹⁵,
(q) —NR²COOR¹⁵,
(r) —SO₂NHR³,
(s) —SO₂NR²R³,
(t) —NO₂,
(u) —NHSO₂CF₃,
(v) —CONR³R³,
(w) —(C₁-C₄)-perfluoroalkyl,
(x) —COOR²,
(y) —SO₃H,
(z) —N(R²)SO₂R¹⁵,
(aa) —NR²CONR³R¹⁵,
(bb) —OC(=O)NR¹⁵R³,
(cc) -aryl,
(dd) —NHSO₂CF₃,
(ee) —SO₂NH-heteroaryl,
(ff) —SO₂NHCOR¹⁵,
(gg) —CONHSO₂R¹⁵,
(hh) —PO(OR²)₂,
(ii) -tetrazol-5-yl,
(jj) —CONH(tetrazol-5-yl), or
(kk) —SO₂NHCN; and R⁷ is:
(a) H,
(b) (C₁-C₆)-alkyl, unsubstituted or substituted with:
   (i) -aryl,
   (ii) —(C₃-C₇)-cycloalkyl,
   (iii) —NR³R¹¹,
   (iv) -morpholin-4-yl,
   (v) —OH,
   (vi) —CO₂R³, or
   (vii) —CON(R³)₂,
(c) aryl, unsubstituted as defined below or substituted with a substituent selected from the group consisting of:
   i) (C₁-C₄)-alkyl,
   ii) —O—(C₁-C₄)-alkyl,
   iii) —CONR³R¹¹,
   iv) F, Cl, Br or I, or
   v) —COOR³;

R⁹ and R¹⁰ are independently:
(a) H,
(b) (C₁-C₆)-alkyl, unsubstituted or substituted with (C₃-C₇)-cycloalkyl,
(c) Cl, Br, F, I,
(d) (C₁-C₆)-alkoxy, or
(e) hydroxy-(C₁-C₆)-alkyl or dihydroxy-(C₁-C₆)-alkyl;

R¹⁴ᵃ and R¹⁴ᵇ are independently:
(a) H,
(b) F, Cl, Br, or I,
(c) —NO₂,
(d) (C₁-C₄)-alkyl,
(e) —OR³,
(f) —S(O)ₙ—(C₁-C₄)-alkyl,
(g) —NHCO—(C₁-C₄)-alkyl,
(h) —NHCO—O(C₁-C₄)-alkyl,
(i) —O—(CH₂)m—OR³,
(j) —CONR³R¹¹, or
(k) —COOR³ and m is 2, 3, or 4; and R¹² and R¹³ are on adjacent carbon atoms are joined together to form a ring structure:

A represents:
a) —O—C(R⁴)=C(R⁴)—,
b) —O—C(R⁴)=N—,
c) —O—[C(R⁸)(R⁸)]s—O—,
d) —C(R⁴)=C(R⁴)—O—,
e) —N=C(R⁴)—O—, or
f) —C(R⁴)=C(R⁴)—C(R⁴)=C(R⁴)—; and s is 1 or 2; and X is:
(a) —O—,
(b) —S(O)ₙ—, or
(c) —NR³—; and R¹⁵ is:
(a) aryl, or
(b) (C₁-C₄)-alkyl, is unsubstituted or substituted with:
   i) NH₂,
   ii) NH[(C₁-C₄)-alkyl],
   iii) N[(C₁-C₄)-alkyl]₂,
   iv) CO₂H,
   v) CO₂(C₁-C₄)-alkyl,
   vi) OH,
   vii) SO₃H, or
   viii) SO₂NH₂; and Z is:
(a) —CO₂H,
(b) -tetrazol-5-yl,
(c) —CONH(tetrazol-5-yl),
(d) —CONHSO₂-phenyl or —CONHSO₂-naphthyl, or
(e) —CONHSO₂-heteroaryl;

aryl is defined as phenyl or naphthyl unsubstituted or substituted with 1 or 2 substituents selected from the group consisting of:
i) Br, I, Cl, F,
ii) (C₁-C₄)-alkyl,
iii) (C₁-C₄)-alkoxy,
iv) NO₂
v) CF₃
vi) SO₂NR³R³,
vii) (C₁-C₄)-alkylthio,
viii) hydroxy,
ix) amino,
x) (C₃-C₇)-cycloalkyl,
xi) (C₃-C₁₀)-alkenyl; and heteroaryl is defined as a 5- or 6-membered heteroaromatic moiety selected from the group consisting of thienyl, furanyl, thiazolyl, oxazolyl, pyridyl or pyrimidinyl, which is unsubstituted, mono- or disubstituted with substituents selected from the group consisting of:
i) Cl, Br, I, or F,
ii) OH,
iii) SH,
iv) NO₂,
v) (C₁-C₄)-alkyl,
vi) (C₂-C₄)-alkenyl,
vii) (C₂-C₄)-alkynyl,
viii) (C₁-C₄)-alkoxy, or
ix) CF₃.

4. A pharmaceutical formulation for the treatment of hypertension which comprises a pharmaceutically acceptable carrier and a therapeutically effective amount of the compound of claim 1.

5. A method of treating cardiovascular disorders by administering to a person in need of such treatment a therapeutically effective amount of a compound of Formula I as recited in claim 1.

6. A method of treating hypertension which comprises administering to a mammal in need of such treatment a therapeutically effective amount of a compound of structural formula I as recited in claim 1.

7. The method as recited in claim 6, wherein the mammal is human.

8. A compound of structural formula II

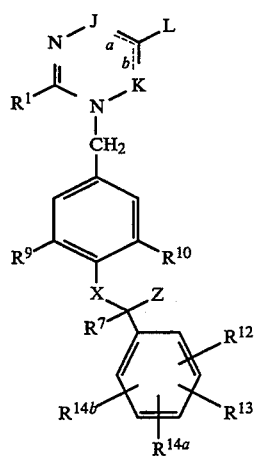

or a pharmaceutically acceptable salt thereof, wherein:
$R^1$ is:
(a) H,
(b) $(C_1-C_6)$-alkyl, $(C_2-C_6)$-alkenyl or $(C_2-C_6)$-alkynyl each of which is unsubstituted or substituted with a substituent selected from the group consisting of:
  i) $(C_3-C_7)$-cycloalkyl,
  ii) $CF_3$,
  iii) $(C_1-C_4)$-alkylthio,
  iv) $(C_1-C_4)$-alkoxy,
(c) $(C_1-C_4)$-perfluoroalkyl,
(d) —$CONR^3R^3$, or
(e) —$NR^3CO$—O—$(C_1-C_4)$-alkyl; and
n is: 0, 1, or 2; and
J is: (a) —C(=M)—, or (b) J and L are connected together to form a 6-membered aromatic ring substituted with $R^{5a}$, $R^{5b}$, $R^{6a}$ and $R^{6b}$;
K is: (a) —C(=M)—, or (b) K and L are connected together to form a 6-membered aromatic ring substituted with $R^{5a}$, $R^{5b}$, $R^{6a}$ and $R^{6b}$, provided that one and only one of J and K is —C(=M)—; and
one of a or b is a double bond in Formula I provided that when J is —C(=M)—, then b is a double bond and when K is —C(=M)—, then a is a double bond;
L is: the point of attachment of the 6-membered fused aromatic ring; and
M is: O, S or $NR^{11}$; and
$R^2$ is:
(a) H,
(b) $(C_1-C_6)$-alkyl; and
$R^3$ is:
(a) $R^2$,
(b) —$CH_2$-aryl, or
(c) aryl; and
$R^4$ groups are independently:
(a) H,
(b) $(C_1-C_6)$-alkyl or $(C_2-C_6)$-alkenyl each of which is unsubstituted or substituted with one of the following substituents,
  i) —OH,
  ii) —O—$(C_1-C_4)$-alkyl,
  iii) —$S(O)_n$—$(C_1-C_4)$-alkyl,
  iv) —$NR^3$—$(C_1-C_4)$-alkyl,
  v) —$NHR^3$,
  vi) —$COOR^3$,
  vii) —$CONHR^3$,
  ix) —$CONR^3R^{11}$, or
  x) $(C_3-C_7)$-cycloalkyl,
(c) $(C_3-C_7)$-cycloalkyl,
(d) F, Cl, Br, I,
(e) $CF_3$,
(f) —$COOR^3$,
(g) —$CONR^3R^{11}$,
(h) —$NR^3R^{11}$,
(i) —$NR^3CONR^3R^{11}$,
(j) —$NR^3COOR^{11}$,
(k) —$SO_2NR^3R^{11}$,
(l) —O—$(C_1-C_4)$-alkyl,
(m) —$S(O)_n$—$(C_1-C_4)$-alkyl, or
(n) —$NHSO_2R^{11}$; and
$R^{5a}$ and $R^{5b}$ are independently:
(a) H,
(b) $(C_1-C_6)$-alkyl, $(C_2-C_6)$-alkenyl or $(C_2-C_6)$-alkynyl,
(c) Cl, Br, I, F,
(d) $CF_3$, or
(e) when $R^{5a}$ and $R^{5b}$ are bonded to adjacent carbon atoms, they can be joined to form a phenyl ring;
$R^{6a}$ and $R^{6b}$ are independently:
(a) H,
(b) aryl-$(C_1-C_4)$-alkyl,
(c) heteroaryl-$(C_1-C_4)$-alkyl,
(d) $(C_1-C_6)$-alkyl, is unsubstituted or substituted with a substituent selected from the group consisting of: —$CON(R^3)_2$, -heteroaryl, —$S(O)_n$—$R^{15}$, -tetrazol-5-yl, —$CONHSO_2R^{15}$, —$SO_2NH$-heteroaryl, —$SO_2NHCOR^{15}$, —$PO(OR^2)_2$, —$PO(OR^3)_2$, —$SO_2NH$—CN, —$NR^2COOR^{15}$, —OH, —$NH_2$, guanidino, $(C_1-C_4)$-alkoxy, $(C_1-C_4)$-alkylthio, $(C_1-C_4)$-alkylamino, $(C_1-C_4)$-dialkylamino, —$COOR^3$, —$CONHR^3$, —O—$COR^3$, or aryl,
(e) —CO-aryl,
(f) $(C_3-C_7)$-cycloalkyl,
(g) Cl, Br, I, F,
(h) —$OR^{11}$,
(i) —SH,
(j) —$S(O)_n$—$(C_1-C_4)$-alkyl,
(k) —$COR^3$,
(l) —$CO_2H$,
(m) —$CO_2$—$(C_1-C_4)$-alkyl,
(n) —$SO_3H$,
(o) —$NR^2R^{15}$,
(p) —$NR^2COR^{15}$,
(q) —$NR^2COOR^{15}$,
(r) —$SO_2NHR^3$,
(s) —$SO_2NR^2R^3$,
(t) —$NO_2$,
(u) —$NHSO_2CF_3$,
(v) —$CONR^3R^3$, (w) —(C$_1$-C$_4$)-perfluoroalkyl,
(x) —COOR$^2$,
(y) —SO$_3$H,
(z) —N(R$^2$)SO$_2$R$^{15}$,
(aa) —NR$^2$CONR$^3$R$^{15}$,
(bb) —OC(=O)NR$^{15}$R$^3$,
(cc) -aryl,
(dd) —NHSO$_2$CF$_3$,
(ee) —SO$_2$NH-heteroaryl,
(ff) —SO$_2$NHCOR$^{15}$,
(gg) —CONHSO$_2$R$^{15}$,
(hh) —PO(OR$^2$)$_2$,
(ii) -tetrazol-5-yl,
(jj) —CONH(tetrazol-5-yl), or
(kk) —SO$_2$NHCN; and R$^7$ is:
(a) H,
(b) (C$_1$-C$_6$)-alkyl, unsubstituted or substituted with:
  (i) -aryl,
  (ii) —(C$_3$-C$_7$)-cycloalkyl,
  (iii) —NR$^3$R$^{11}$,
  (iv) -morpholin-4-yl,
  (v) —OH,
  (vi) —CO$_2$R$^3$, or
  (vii) —CON(R$^3$)$_2$,
(c) aryl, unsubstituted as defined below or substituted with a substituent selected from the group consisting of:
  i) (C$_1$-C$_4$)-alkyl,
  ii) —O—(C$_1$-C$_4$)-alkyl,
  iii) —CONR$^3$R$^{11}$,
  iv) F, Cl, Br or I, or
  v) —COOR$^3$;

R$^9$ and R$^{10}$ are independently:
(a) H,
(b) (C$_1$-C$_6$)-alkyl, unsubstituted or substituted with (C$_3$-C$_7$)-cycloalkyl,
(c) Cl, Br, F, I,
(d) (C$_1$-C$_6$)-alkoxy, or
(e) hydroxy-(C$_1$-C$_6$)-alkyl or dihydroxy-(C$_1$-C$_6$)-alkyl;

R$^{14a}$ and R$^{14b}$ are independently:
(a) H,
(b) F, Cl, Br, or I,
(c) —NO$_2$,
(d) (C$_1$-C$_4$)-alkyl,
(e) —OR$^3$,
(f) —S(O)$_n$—(C$_1$-C$_4$)-alkyl,
(g) —NHCO—(C$_1$-C$_4$)-alkyl,
(h) —NHCO—O(C$_1$-C$_4$)-alkyl,
(i) —O—(CH$_2$)m—OR$^3$,
(j) —CONR$^3$R$^{11}$, or
(k) —COOR$^3$ and
m is 2, 3, or 4; and
R$^{12}$ and R$^{13}$ are on adjacent carbon atoms are joined together to form a ring structure:

;

A represents:
a) —O—C(R$^4$)=C(R$^4$)—,
b) —O—C(R$^4$)=N—,
c) —O—[C(R$^8$)(R$^8$)]s—O—,
d) —C(R$^4$)=C(R$^4$)—O—,
e) —N=C(R$^4$)—O—, or
f) —C(R$^4$)=C(R$^4$)—C(R$^4$)=C(R$^4$)—; and
s is 1 or 2; and X is:
(a) —O—,
(b) —S(O)$_n$—, or
(c) —NR$^3$—; and R$^{15}$ is:
(a) aryl, or
(b) (C$_1$-C$_4$)-alkyl, is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H,
  v) CO$_2$(C$_1$-C$_4$)-alkyl,
  vi) OH,
  vii) SO$_3$H, or
  viii) SO$_2$NH$_2$; and Z is:
(a) —CO$_2$H,
(b) -tetrazol-5-yl,
(c) —CONH(tetrazol-5-yl),
(d) —CONHSO$_2$-aryl, or
(e) —CONHSO$_2$-heteroaryl;

aryl is defined as phenyl or naphthyl unsubstituted or substituted with 1 or 2 substituents selected from the group consisting of:
  i) Br, I, Cl, F,
  ii) (C$_1$-C$_4$)-alkyl,
  iii) (C$_1$-C$_4$)-alkoxy,
  iv) NO$_2$
  v) CF$_3$
  vi) SO$_2$NR$^3$R$^3$,
  vii) (C$_1$-C$_4$)-alkylthio,
  viii) hydroxy,
  ix) amino,
  x) (C$_3$-C$_7$)-cycloalkyl,
  xi) (C$_3$-C$_{10}$)-alkenyl; and heteroaryl is defined as a 5- or 6-membered heteroaromatic moiety selected from the group consisting of thienyl, furanyl, thiazolyl, oxazolyl, pyridyl or pyrimidinyl, which is unsubstituted, mono- or disubstituted with substituents selected from the group consisting of:
  i) Cl, Br, I, or F,
  ii) OH,
  iii) SH,
  iv) NO$_2$,
  v) (C$_1$-C$_4$)-alkyl,
  vi) (C$_2$-C$_4$)-alkenyl,
  vii) (C$_2$-C$_4$)-alkynyl,
  viii) (C$_1$-C$_4$)-alkoxy, or
  ix) CF$_3$.

9. The compound as recited in claim 1 wherein the structural formula is:

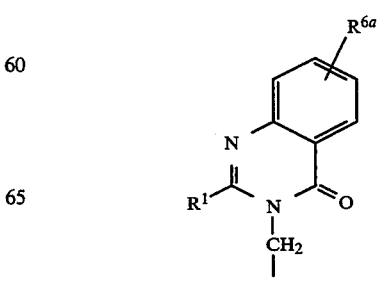

-continued

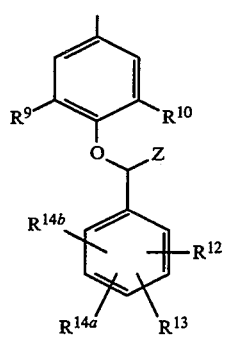

and the substituents are as defined in the table below:

| R¹ | R⁶ᵃ | R⁹ | R¹⁰ | R¹²,R¹³ | R¹⁴ᵃ,R¹⁴ᵇ | Z |
|---|---|---|---|---|---|---|
| H | 8-Me | H | Pr | 3,4-methylenedioxy | H,H | COOH |
| H | 8-Me | Pr | Pr | 3,4-methylenedioxy | H,H | COOH |
| H | 8-Me | H | Pr | 3,4-methylenedioxy | H,H | CONHSO₂Ph |
| H | 8-Me | Pr | Pr | 3,4-methylenedioxy | H,H | CONHSO₂Me |
| i-Pr | 8-Me | Pr | Pr | 3,4-methylenedioxy | H,H | COOH |
| i-Pr | 8-Br | Pr | Pr | 3,4-methylenedioxy | H,H | COOH |
| Ph | 8-Me | Pr | Pr | 3,4-methylenedioxy | H,H | COOH |
| (2-Et)Pr | 8-Me | Pr | Pr | 3,4-methylenedioxy | H,H | COOH |
| H | 8-Me | H | Pr | 3,4-methylenedioxy | H,H | CONHSO₂Ph(4-iPr) |
| i-Pr | 8-Br | H | Pr | 3,4-methylenedioxy | H,H | CONHSO₂Ph(4-iPr) |
| H | 6-PhCONH | Bu | H | 3,4-methylenedioxy | H,H | COOH |
| Me | 8-Me | Pr | H | 3,4-methylenedioxy | H,H | COOH |
| me | 8-Me | Pr | H | 3,4-methylenedioxy | H,H | CONHSo₂Ph(4-iPr) |
| Me | 8-Me | Pr | Pr | 3,4-methylenedioxy | H,H | COOH |
| H | 8-Me | Cl | Cl | 3,4-methylenedioxy | H,H | COOH |
| Me | 8-Me | Br | Br | 3,4-methylenedioxy | H,H | COOH |
| H | 8-Me | H | Pr | 3,4-methylenedioxy | H, 5-Br | COOH |
| H | 8-Me | Pr | Pr | 3,4-methylenedioxy | H, 5-Br | COOH |
| H | 8-Me | H | Pr | 3,4-methylenedioxy | H, 5-Br | CONHSO₂Ph(4-iPr). |

10. A compound of structural formula III:

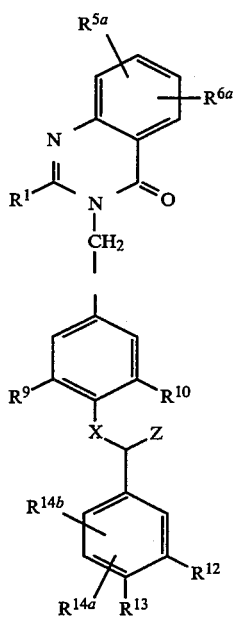

or a pharmaceutically acceptable salt thereof, wherein:
R¹ is:
(a) H,
(b) (C₁-C₆)-alkyl, (C₂-C₆)-alkenyl or (C₂-C₆)-alkynyl each of which is unsubstituted or substituted with a substituent selected from the group consisting of:
i) (C₃-C₇)-cycloalkyl,
ii) CF₃,
iii) (C₁-C₄)-alkylthio,
iv) (C₁-C₄)-alkoxy,
(c) (C₁-C₄)-perfluoroalkyl,
(d) —CONR³R³, or
(e) —NR³CO—O—(C₁-C₄)-alkyl; and
n is: 0, 1, or 2; and
R² is:
(a) H,
(b) (C₁-C₆)-alkyl; and
R³ is:
(a) R²,
(b) —CH₂-aryl, wherein aryl is defined as phenyl or naphthyl unsubstituted or substituted with 1 or 2 substituents selected from the group consisting of:
i) Br, I, Cl, F,
ii) (C₁-C₄)-alkyl,
iii) (C₁-C₄)-alkoxy,
iv) NO₂
v) CF₃
vi) SO₂NR³R³,
vii) (C₁-C₄)-alkylthio,
viii) hydroxy,
ix) amino,
x) (C₃-C₇)-cycloalkyl,
xi) (C₃-C₁₀)-alkenyl; and
(c) aryl, wherein aryl is as defined in R³(b); and
R⁴ groups are independently:
(a) H,
(b) (C₁-C₆)-alkyl or (C₂-C₆)-alkenyl each of which is unsubstituted or substituted with one of the following substituents,
i) —OH,
ii) —O—(C₁-C₄)-alkyl,
iii) —S(O)ₙ—(C₁-C₄)-alkyl,
iv) —NR³—(C₁-C₄)-alkyl,
v) —NHR³,
vi) —COOR³,
vii) —CONHR³,
ix) —CONR³R¹¹, or
x) (C₃-C₇)-cycloalkyl,
(c) (C₃-C₇)-cycloalkyl,
(d) F, Cl, Br, I,
(e) CF₃, (f) —COOR$^3$,
(g) —CONR$^3$R$^{11}$,
(h) —NR$^3$R$^{11}$,
(i) —NR$^3$CONR$^3$R$^{11}$,
(j) —NR$^3$COOR$^{11}$,
(k) —SO$_2$NR$^3$R$^{11}$,
(l) —O—(C$_1$-C$_4$)-alkyl,
(m) —S(O)$_n$—(C$_1$-C$_4$)-alkyl, or
(n) —NHSO$_2$R$^{11}$; and R$^{5a}$ is:
(a) H,
(b) (C$_1$-C$_6$)-alkyl, (C$_2$-C$_6$)-alkenyl or (C$_2$-C$_6$)-alkynyl,
(c) Cl, Br, I, F,
(d) CF$_3$, or
(e) when R$^{5a}$ and R$^{5b}$ are bonded to adjacent carbon atoms, they can be joined to form a phenyl ring;

R$^{6a}$ is:
(a) H,
(b) aryl-(C$_1$-C$_4$)-alkyl, wherein aryl is as defined in R$^3$(b),
(c) heteroaryl-(C$_1$-C$_4$)-alkyl, wherein heteroaryl is defined as a 5- or 6-membered heteroaromatic moiety selected from the group consisting of thiophene, furan, thiazole, oxazole, pyridine or pyrimidine, which is unsubstituted, mono- or disubstituted with substituents selected from the group consisting of:
  i) Cl, Br, I, or F,
  ii) OH,
  iii) SH,
  iv) NO$_2$,
  v) (C$_1$-C$_4$)-alkyl,
  vi) (C$_2$-C$_4$)-alkenyl,
  vii) (C$_2$-C$_4$)-alkynyl,
  viii) (C$_1$-C$_4$)-alkoxy, or
  ix) CF$_3$,
(d) (C$_1$-C$_6$)-alkyl, is unsubstituted or substituted with a substituent selected from the group consisting of: —CON(R$^3$)$_2$, -heteroaryl, wherein heteroaryl is as defined in R$^{6a}$(c), —S(O)$_n$—R$^{15}$, -tetrazol-5-yl, —CONHSO$_2$R$^{15}$, —SO$_2$NH-heteroaryl, wherein heteroaryl is as defined in R$^{6a}$(c), —SO$_2$NHCOR$^{15}$, —PO(OR$^2$)$_2$, —PO(OR$^3$)$_2$, —SO$_2$NH—CN, —NR$^2$COOR$^{15}$, —OH, —NH$_2$, guanidino, (C$_1$-C$_4$)-alkoxy, (C$_1$-C$_4$)-alkylthio, (C$_1$-C$_4$)-alkylamino, (C$_1$-C$_4$)-dialkylamino, —COOR$^3$, —CONHR$^3$, —O—COR$^3$, or aryl, wherein aryl is as defined in R$^3$(b),
(e) —CO-aryl, wherein aryl is as defined in R$^3$(b),
(f) (C$_3$-C$_7$)-cycloalkyl,
(g) Cl, Br, I, F,
(h) —OR$^{11}$,
(i) —SH,
(j) —S(O)$_n$—(C$_1$-C$_4$)-alkyl,
(k) —COR$^3$,
(l) —CO$_2$H,
(m) —CO$_2$—(C$_1$-C$_4$)-alkyl,
(n) —SO$_3$H,
(o) —NR$^2$R$^{15}$,
(p) —NR$^2$COR$^{15}$,
(q) —NR$^2$COOR$^{15}$,
(r) —SO$_2$NHR$^3$,
(s) —SO$_2$NR$^2$R$^3$,
(t) —NO$_2$,
(u) —NHSO$_2$CF$_3$,
(v) —CONR$^3$R$^3$,
(w) —(C$_1$-C$_4$)-perfluoroalkyl,
(x) —COOR$^2$,
(y) —SO$_3$H,
(z) —N(R$^2$)SO$_2$R$^{15}$,
(aa) —NR$^2$CONR$^3$R$^{15}$,
(bb) —OC(=O)NR$^{15}$R$^3$,
(cc) -aryl, wherein aryl is phenyl or naphthyl, which is unsubstituted or substituted as defined in R$^3$(b),
(dd) —NHSO$_2$CF$_3$,
(ee) —SO$_2$NH-heteroaryl, wherein heteroaryl is unsubstituted or substituted as defined in R$^{6a}$(c),
(ff) —SO$_2$NHCOR$^{15}$,
(gg) —CONHSO$_2$R$^{15}$,
(hh) —PO(OR$^2$)$_2$,
(ii) -tetrazol-5-yl,
(jj) —CONH(tetrazol-5-yl), or
(kk) —SO$_2$NHCN; and R$^9$ and R$^{10}$ are independently:
(a) H,
(b) (C$_1$-C$_6$)-alkyl, unsubstituted or substituted with (C$_3$-C$_7$)-cycloalkyl,
(c) Cl, Br, F, I,
(d) (C$_1$-C$_6$)-alkoxy, or
(e) hydroxy-(C$_1$-C$_6$)-alkyl or dihydroxy-(C$_1$-C$_6$)-alkyl;

R$^{14a}$ and R$^{14b}$ are independently:
(a) H,
(b) F, Cl, Br, or I,
(c) —NO$_2$,
(d) (C$_1$-C$_4$)-alkyl,
(e) —OR$^3$,
(f) —S(O)$_n$—(C$_1$-C$_4$)-alkyl,
(g) —NHCO—(C$_1$-C$_4$)-alkyl,
(h) —NHCO—O(C$_1$-C$_4$)-alkyl,
(i) —O—(CH$_2$)m—OR$^3$,
(j) —CONR$^3$R$^{11}$, or
(k) —COOR$^3$; and m is 2, 3, or 4; and R$^{12}$ and R$^{13}$ are on adjacent carbon atoms are joined together to form a ring structure:

A represents:
 a) —O—C(R$^4$)=C(R$^4$)—,
 b) —O—C(R$^4$)=N—,
 c) —O—[C(R$^8$)(R$^8$)]s —O—,
 d) —C(R$^4$)=C(R$^4$)—O—,
 e) —N=C(R$^4$)—O—, or
 f) —C(R$^4$)=C(R$^4$)—C(R$^4$)=C(R$^4$)—; and s is 1 or 2; and X is:
 (a) —O—,
 (b) —S(O)$_n$—, or
 (c) —NR$^3$—; and R$^{15}$ is:
 (a) aryl, wherein aryl is as defined in R$^3$(b), or
 (b) (C$_1$-C$_4$)-alkyl, is unsubstituted or substituted with:
  i) NH$_2$,
  ii) NH[(C$_1$-C$_4$)-alkyl],
  iii) N[(C$_1$-C$_4$)-alkyl]$_2$,
  iv) CO$_2$H, v) $CO_2(C_1$–$C_4)$-alkyl,
vi) OH,
vii) $SO_3H$, or
viii) $SO_2NH_2$; and Z is:
(a) —$CO_2H$,
(b) -tetrazol-5-yl,
(c) —CONH(tetrazol-5-yl),
(d) —$CONHSO_2$-phenyl or —$CONHSO_2$-naphthyl, wherein phenyl or naphthyl is unsubstituted or substituted as defined in $R^3$(b), or
(e) —$CONHSO_2$-heteroaryl, wherein heteroaryl is as defined in $R^{6a}$(c).

* * * * *